(12) United States Patent
Barta et al.

(10) Patent No.: US 8,063,240 B2
(45) Date of Patent: Nov. 22, 2011

(54) PROSTAGLANDIN E1 AND E2 ANALOGS FOR THE TREATMENT OF VARIOUS MEDICAL CONDITIONS

(75) Inventors: Nancy S. Barta, Brighton, MI (US); Stephen D. Barrett, Hartland, MI (US); Gregory W. Endres, Saline, MI (US); Andriy M. Kornilov, Ypsilanti, MI (US); Kirk M. Maxey, Ann Arbor, MI (US); Adam Uzieblo, Farmington Hills, MI (US)

(73) Assignee: Cayman Chemical Company, Incorporated, Ann Arbor, MI (US)

( * ) Notice: Subject to any disclaimer, the term of this patent is extended or adjusted under 35 U.S.C. 154(b) by 491 days.

(21) Appl. No.: 12/271,764

(22) Filed: Nov. 14, 2008

(65) Prior Publication Data

US 2009/0221654 A1 Sep. 3, 2009

Related U.S. Application Data

(60) Provisional application No. 60/987,859, filed on Nov. 14, 2007, provisional application No. 61/037,493, filed on Mar. 18, 2008.

(51) Int. Cl.
*C07C 69/74* (2006.01)
*C07C 61/06* (2006.01)
*A01N 37/08* (2006.01)

(52) U.S. Cl. ........ 560/121; 560/122; 562/503; 562/504; 514/573

(58) Field of Classification Search ................ None
See application file for complete search history.

(56) References Cited

U.S. PATENT DOCUMENTS

| | | | |
|---|---|---|---|
| 3,886,206 | A | 5/1975 | Crabbe et al. |
| 4,138,590 | A | 2/1979 | Kao |
| 5,576,347 | A | 11/1996 | Sredni et al. |
| 6,426,359 | B1 | 7/2002 | Cameron et al. |
| 6,476,064 | B1 * | 11/2002 | Old et al. ........ 514/438 |
| 6,562,868 | B1 | 5/2003 | Stjernschantz et al. |
| 6,894,175 | B1 | 5/2005 | DeLong |
| 7,326,732 | B2 | 2/2008 | Oxford et al. |
| 2002/0177620 | A1 | 11/2002 | Burk et al. |
| 2007/0112067 | A1 * | 5/2007 | Garvey et al. ........ 514/509 |

FOREIGN PATENT DOCUMENTS

| | | |
|---|---|---|
| WO | 98/34916 A1 | 8/1998 |
| WO | 00/31084 A1 | 6/2000 |
| WO | 00/40248 A1 | 7/2000 |
| WO | 01/46140 A1 | 6/2001 |
| WO | 03/037433 A1 | 5/2003 |
| WO | 03/040126 A1 | 5/2003 |
| WO | 2007/027468 A1 | 3/2007 |
| WO | 2008/073748 A1 | 6/2008 |

OTHER PUBLICATIONS

"Crystallization" in Kirk-Othmer Encyclopedia of Chemical Technology Copyright © 2002 by John Wiley & Sons, Inc., pp. 95-147, Article Online Posting Date: Aug. 16, 2002.*
Rouhi, "The Right Stuff, from research and development to the clinic, getting drug crystals right is full of pitfalls", Chemical & Engineering News, Feb. 24, 2003, pp. 32-35.*
Ullmann's Encyclopedia of Industrial Chemistry, Copyright © 2002 by Wiley-VCH Verlag GmbH & Co. KGaA, pp. 1-51.*
Breyer et al., "Structure-Function Analyses of Eicosanoid Receptors", Annals of New York Academy of Sciences, 905, (2000), pp. 221-231.
Klimko et al., "15-Fluoro Prostaglandin FP Agonists: A New Class of Topical Ocular Hypotensives", Bioorganic & Medicinal Chemistry 12 (2004), pp. 3451-3469.
Matsumara et al., "Novel Fluoroprostacyclin Analogs with Modified Cycloalkylenyl Chains. Highly Potent and Orally Active Anti-Aging Agents", Chem. Pharm. Bull 43(2), (1995), pp. 353-355U.
Waterbury et al., "EP3 But Not EP2, FP, or TP Prostanoid-Receptor Stimulation May Reduce Intraocular Pressure", Investigative Opthalmology & Visual Science, vol. 31, No. 12, Dec. 1990, pp. 2560-2567.
Li et al., "A Novel, Non-Prostanoid EP2 Receptor-Selective Prostaglandin E2 Agonist Stimulates Local Bone Formation and Enhances Fracture Healing", Journal of Bone and Mineral Research, vol. 18, No. 11, 2003, pp. 2033-2042.
Grieco et al., "Fluoroprostaglandins: Total Synthesis of (+)-13-Fluoroprostaglandin F2alpha Methyl Ester", Journal of Organic Chemistry, 50, (1985), pp. 3111-3115.
North et al., "Prostaglandin E2 Regulates Vertebrate Haematopoietic Stem Cell Homeostasis," Nature, vol. 447, Jun. 21, 2007, pp. 1007-1011.
Paralkar et al., "An EP2 Receptor-Selective Prostaglandin E2 Agonist Induces Bone Healing," Proceedings of the National Academy of Sciences, vol. 100, No. 11, May 27, 2003, pp. 6736-6740.
Asai et al., "Synthesis of New Stable Fluoroprostacyclin Analogs with Potent Anti-Anginal Activity", Tetrahedron Letters, vol. 36, No. 2, (1995), pp. 273-276.
Matsumura et al., "Synthesis of the Highly Potent Prostanoid FP Receptor Agonist, AFP-168: a novel 15-deoxy-15, 15-difluoroprostaglandin F2alpha Derivative", Tetrahedron Letters 45 (2004), pp. 1527-1529.
Matsumura et al., "Synthesis of 7-Fluoro-2, 4-methylene-17, 20-dimethylprostacyclins. Novel Stable Prostacyclin Analogs as Potent Anti-anginal Agents", Tetrahedron, vol. 51, No. 32, (1995), pp. 8771-8782.

* cited by examiner

*Primary Examiner* — Karl J Puttlitz
(74) *Attorney, Agent, or Firm* — Steven W. Hays, Esq.; Pietragallo Gordon Alfano Bosick & Raspanti, LLP

(57) ABSTRACT

A prostaglandin analog with selectivity to EP receptors and demonstrating EP agonist activity that may be used to expand hematopoietic stem cell populations or to treat or prevent influenza, bone fracture, bone disease, glaucoma, ocular hypertension, dysmenorrhoea, pre-term labor, immune disorders, osteoporosis, asthma, allergy, male sexual dysfunction, female sexual dysfunction, periodontal disease, gastric ulcer, renal disease, or other EP receptor-mediated conditions.

14 Claims, No Drawings

PROSTAGLANDIN E1 AND E2 ANALOGS FOR THE TREATMENT OF VARIOUS MEDICAL CONDITIONS

CROSS REFERENCE TO RELATED APPLICATIONS

The present invention claims priority from U.S. Provisional Application No. 60/987,859 filed Nov. 14, 2007, and U.S. Provisional Application No. 61/037,493 filed Mar. 18, 2008.

FIELD OF THE INVENTION

The present invention relates to pharmaceutically active compounds and more particularly to prostaglandin analogs with selectivity for prostaglandin E (EP) receptors and demonstrating EP agonist activity, and the use of such compounds and compositions thereof for the treatment of various medical conditions.

BACKGROUND OF THE INVENTION

Prostanoids are ubiquitous lipid mediator biomolecules involved in numerous physiological processes, such as the contraction and relaxation of smooth muscle, vasodilation, vasoconstriction, pain, regulation of blood pressure, and modulation of inflammation. Prostanoids are a family of eicosanoids that comprise prostaglandins (PGs), prostacyclins (PGIs), and thromboxanes (Txs). Their receptors belong to the G-protein coupled receptor (GPCR) superfamily of receptors and may be grouped into five classes, namely, prostaglandin D (DP), prostaglandin E (EP), prostaglandin F (FP), prostaglandin I (IP), and Thromboxane A (TP) based on their sensitivity to five naturally occurring prostanoids, $PGD_2$, $PGE_2$, $PGF_{2\alpha}$, $PGI_2$, and $TxA_2$, respectively (Coleman, R. A., Prostanoid Receptors. *IUPHAR Compendium of Receptor Characterization and Classification*, 2$^{nd}$ Edition, 338-353, 2000). EP receptors have been characterized into four subtypes $EP_1$, $EP_2$, $EP_3$, and $EP_4$. Each subtype has been cloned and is distinct at both a molecular and pharmacological level.

Prostanoids are synthesized from essential fatty acids comprising twenty carbon atoms, such as arachidonic acid and 8,11,14-eicosatrienoic acid. Prostanoids are synthesized in response to both extracellular and intracellular stimuli and are then rapidly released from the cells. In general, the short half-lives of most prostanoids ensure they act near the sites of their biosynthesis.

Prostaglandin $E_2$ ($PGE_2$) is a potent endogenous EP receptor agonist derived from arachidonic acid and possesses two carbon-carbon double bonds, one in each the α-chain and ω-chain, and is thus called a "Series 2" prostaglandin.

Prostaglandin $E_1$ ($PGE_1$) is derived from 8,11,14-eicosatrienoic acid and possesses only one carbon-carbon double bond, located in the co-chain, and is thus called a "Series 1" prostaglandin.

Both prostanoid and non-prostanoid EP receptor agonists are known. EP receptor agonists may have a number of utilities. These include, but are not limited to treatment of influenza (WO 2008/058766), bone fracture healing (Li, M., et al., *J. Bone Miner. Res.*, 18(11), 2003, 2033-2042; Paralkar, V. M., *PNAS*, 100(11), 2003, 6736-6740; WO 2002/24647; WO 1998/27976), bone disease (WO 2002/24647), glaucoma (WO 2008/015517; WO 2007/027468; WO 2003/040126), ocular hypertension (WO 2003/040126), dysmenorrhoea (WO 2003/037433), pre-term labor (GB 2 293 101), immune disorders (WO 2003/037433), osteoporosis (WO 1998/27976; WO 2001/46140), asthma (WO 2003/037433), allergy (WO 2003/037433), fertility (Breyer, R. M., et al., *Ann. N.Y. Acad. Sci.*, 905, 2000, 221-231), male sexual dysfunction (WO 2000/40248), female sexual dysfunction (U.S. Pat. No. 6,562,868), periodontal disease (WO 2000/31084), gastric ulcer (U.S. Pat. No. 5,576,347), and renal disease (WO 1998/34916). EP receptor agonists may also be useful for expansion of hematopoietic stem cell populations (WO 2008/073748; North, T. E., et al., *Nature*, 447, 2007, 1007-1011).

SUMMARY OF THE INVENTION

The exemplary embodiments may be directed to compounds of structural formula (I) that may be used to expand hematopoietic stem cell populations or to treat or prevent influenza, bone fracture, bone disease, glaucoma, ocular hypertension, dysmenorrhoea, pre-term labor, immune disorders, osteoporosis, asthma, allergy, male sexual dysfunction, female sexual dysfunction, periodontal disease, gastric ulcer, renal disease, or other EP receptor-mediated conditions wherein C9, $C^{11}$, $R^1$, $R^2$, $Z^1$, $Z^2$, $Z^3$, $Z^4$, $Z^5$, $Z^6$, m and n are defined herein:

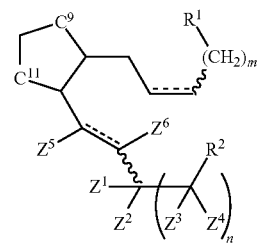

I

Another aspect of the embodiment may be a pharmaceutical composition comprising a pharmaceutically effective amount of a compound according to formula (I), any stereoisomer or geometric isomer thereof, or a prodrug thereof, or a hydrate or solvate thereof, or a pharmaceutically acceptable salt thereof, in admixture with a pharmaceutically acceptable carrier.

Another aspect of the embodiment may be directed to a method of expanding hematopoietic stem cell populations in a culture or patient in need thereof by administering to the culture or patient a compound according to formula (I), any stereoisomer or geometric isomer thereof, or a prodrug thereof, or a hydrate or solvate thereof, or a pharmaceutically acceptable salt thereof.

Another aspect of the embodiment may be directed to a method of treating or preventing influenza, bone fracture, bone disease, glaucoma, ocular hypertension, dysmenorrhoea, pre-term labor, immune disorders, osteoporosis, asthma, allergy, male sexual dysfunction, female sexual dysfunction, periodontal disease, gastric ulcer, renal disease, or other EP receptor-mediated conditions in a patient in need thereof by administering to the patient a compound according to formula (I), any stereoisomer or geometric isomer thereof, or a prodrug thereof, or a hydrate or solvate thereof, or a pharmaceutically acceptable salt thereof.

Other exemplary embodiments of the invention will become apparent from the detailed description provided hereinafter. It should be understood that the detailed description and specific examples, while disclosing exemplary embodiments of the invention, are intended for purposes of illustration only and are not intended to limit the scope of the invention.

DETAILED DESCRIPTION OF THE INVENTION

The exemplary embodiments may be directed to a compound of formula (I), their preparation, pharmaceutical compositions comprising these compounds, and their pharmaceutical use in the prevention and treatment of EP receptor-mediated diseases or conditions. The compounds of formula (I) are shown below:

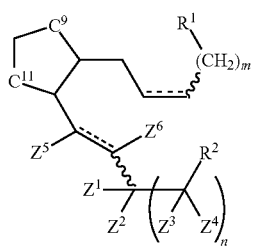

I wherein:
dashed bonds may each independently represent a second carbon-carbon bond in order to give a carbon-carbon double bond with either (E) or (Z) geometry or may be ignored in order to give a carbon-carbon single bond;

$C^9$ and $C^{11}$ each is independently $C=CH_2$, $C=O$, $CF_2$, CHF (any stereoisomer), or C(H)OH (any stereoisomer) with the proviso that $C^9$ does not equal $C^{11}$ and also with the proviso that when one of either C9 or $C^{11}$ is CHF, the other is not C(H)OH;

$R^1$ is $CO_2R^3$, $CH_2OR^3$, $CONR^4R^5$, $COCH_2OH$, $CONR^4SO_2R^5$, $P(O)(OR^4)_2$, or

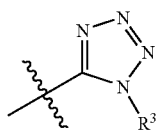

wherein $R^3$ is hydrogen or $(C_1-C_6)$-alkyl, and
wherein $R^4$ and $R^5$ each is independently hydrogen or $(C_1-C_6)$-alkyl;

m is 0, 1, 2, or 3;

$Z^1$ and $Z^2$ each is independently hydrogen, fluorine, hydroxy, or methyl, or together are an oxygen atom that form a carbonyl group with the adjoining carbon atom of the ω chain; $Z^3$ and $Z^4$ each is independently hydrogen, fluorine, hydroxy, or methyl;

n is 0 or 1;

$Z^5$ and $Z^6$ each is independently hydrogen or fluorine;

$R^2$ is

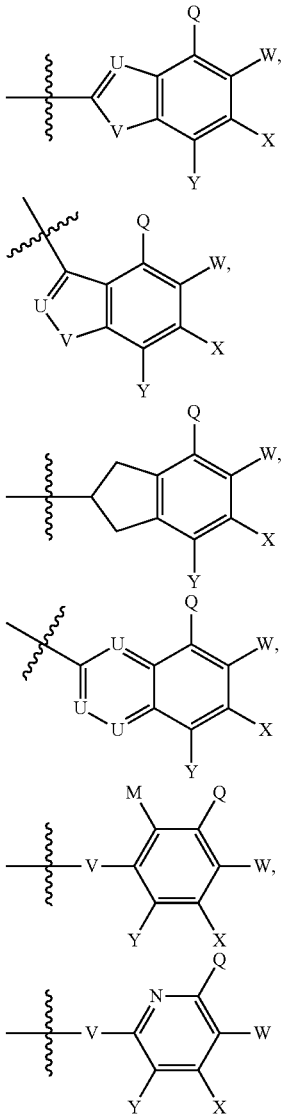

wherein V, if present, is O, S, or $NR^6$,
wherein any U is CH or N.
wherein M, Q, W, X, and Y are independently hydrogen, fluorine, chlorine, bromine, iodine, hydroxy, methoxy, trifluoromethoxy, cyano, trifluoromethyl, $(C_1-C_6)$-alkyl, $(C_3-C_6)$-cycloalkyl, $(C_2-C_6)$-alkenyl, or $(C_2-C_6)$-alkynyl wherein any alkyl, cycloalkyl, alkenyl, or alkynyl is optionally substituted with one or more fluorine atoms, and
wherein $R^6$ is hydrogen, $(C_1-C_6)$-alkyl, $(C_3-C_6)$-cycloalkyl, $(C_2-C_6)$-alkenyl, $(C_2-C_6)$-alkynyl, phenyl, benzyl, three- to six-membered heterocycle, or five- to six-membered heteroaryl.

The exemplary embodiment above may also include any stereoisomer or geometric isomer thereof, or an equivalent thereof, or a prodrug thereof, or a hydrate or solvate thereof, or a pharmaceutically acceptable salt thereof.

Another exemplary embodiment may be directed to a compound of formula (I) wherein $C^9$ is C=O and $C^{11}$ is C(H)OH.

Another exemplary embodiment may be directed to a compound of formula (I) wherein $C^9$ is C(H)OH and $C^{11}$ is C=O.

Another exemplary embodiment may be directed to a compound of formula (I) wherein $C^9$ is C=O and $C^{11}$ is C=CH$_2$.

Another exemplary embodiment may be directed to a compound of formula (I) wherein $C^9$ is C(H)OH and $C^{11}$ is C=CH$_2$.

Another exemplary embodiment may be directed to a compound of formula (I) wherein $C^9$ is C=CH$_2$ and $C^{11}$ is C=O.

Another exemplary embodiment may be directed to a compound of formula (I) wherein $C^9$ is C=CH$_2$ and $C^{11}$ is C(H)OH.

Another exemplary embodiment may be directed to a compound of formula (I) wherein $C^9$ is C=O and $C^{11}$ is CF$_2$.

Another exemplary embodiment may be directed to a compound of formula (I) wherein $C^9$ is C(H)OH and $C^{11}$ is CF$_2$.

Another exemplary embodiment may be directed to a compound of formula (I) wherein $C^9$ is CF$_2$ and $C^{11}$ is C=O.

Another exemplary embodiment may be directed to a compound of formula (I) wherein $C^9$ is CF$_2$ and $C^{11}$ is C(H)OH.

Another exemplary embodiment may be directed to a compound of formula (I) wherein $C^9$ is C=O and $C^{11}$ is CHF.

Another exemplary embodiment may be directed to a compound of formula (I) wherein $C^9$ is CHF and $C^{11}$ is C=O.

Another exemplary embodiment may be directed to a compound of formula (I) wherein $R^1$ is CO$_2$H.

Another exemplary embodiment may be directed to a compound of formula (I) wherein $R^1$ is CO$_2{}^i$Pr.

Another exemplary embodiment may be directed to a compound of formula (I) wherein $R^1$ is CON(H)Et.

Another exemplary embodiment may be directed to a compound of formula (I) wherein $R^1$ is CON(H)SO$_2$Me.

Another exemplary embodiment may be directed to a compound of formula (I) wherein $R^1$ is CH$_2$OH.

Another exemplary embodiment may be directed to a compound of formula (I) wherein $R^1$ is

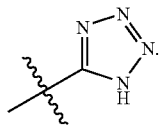

Another exemplary embodiment may be directed to a compound of formula (I) wherein m is 3.

Another exemplary embodiment may be directed to a compound of formula (I) wherein $Z^1$ is hydroxy and $Z^2$ is hydrogen.

Another exemplary embodiment may be directed to a compound of formula (I) wherein $Z^1$ is hydroxy and $Z^2$ is methyl.

Another exemplary embodiment may be directed to a compound of formula (I) wherein $Z^1$ is fluorine and $Z^2$ is hydrogen.

Another exemplary embodiment may be directed to a compound of formula (I) wherein each $Z^1$ and $Z^2$ is hydrogen.

Another exemplary embodiment may be directed to a compound of formula (I) wherein each $Z^1$ and $Z^2$ is fluorine.

Another exemplary embodiment may be directed to a compound of formula (I) wherein each $Z^1$ and $Z^2$ is methyl.

Another exemplary embodiment may be directed to a compound of formula (I) wherein $Z^1$ and $Z^2$ together is an oxygen atom that form a carbonyl with the adjoining carbon atom.

Another exemplary embodiment may be directed to a compound of formula (I) wherein each $Z^3$ and $Z^4$ is hydrogen.

Another exemplary embodiment may be directed to a compound of formula (I) wherein each $Z^3$ and $Z^4$ is fluorine.

Another exemplary embodiment may be directed to a compound of formula (I) wherein each $Z^3$ and $Z^4$ is methyl.

Another exemplary embodiment may be directed to a compound of formula (I) wherein $Z^3$ is hydroxy and $Z^4$ is hydrogen.

Another exemplary embodiment may be directed to a compound of formula (I) wherein $Z^3$ is hydroxy and $Z^4$ is methyl.

Another exemplary embodiment may be directed to a compound of formula (I) wherein $Z^3$ is methyl and $Z^4$ is hydrogen.

Another exemplary embodiment may be directed to a compound of formula (I) wherein $Z^3$ and $Z^4$ together is an oxygen atom that form a carbonyl with the adjoining carbon atom.

Another exemplary embodiment may be directed to a compound of formula (I) wherein n is 0.

Another exemplary embodiment may be directed to a compound of formula (I) wherein n is 1.

Another exemplary embodiment may be directed to a compound of formula (I) wherein $Z^5$ and $Z^6$ are hydrogen.

Another exemplary embodiment may be directed to a compound of formula (I) wherein $Z^5$ is hydrogen and $Z^6$ is fluorine.

Another exemplary embodiment may be directed to a compound of formula (I) wherein $Z^5$ is fluorine and $Z^6$ is hydrogen.

Another exemplary embodiment may be directed to a compound of formula (I) wherein $R^2$ is phenyl.

Another exemplary embodiment may be directed to a compound of formula (I) wherein $R^2$ is —OPh.

Another exemplary embodiment may be directed to a compound of formula (I) wherein $R^2$ is

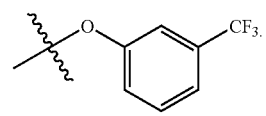

Another exemplary embodiment may be directed to a compound of formula (I) wherein $R^2$ is

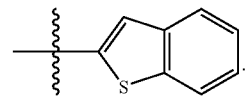

Another exemplary embodiment may be directed to a compound of formula (I) wherein $R^2$ is

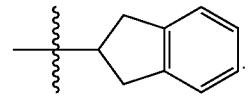

Another exemplary embodiment may be directed to a compound of formula (I) wherein $R^2$ is

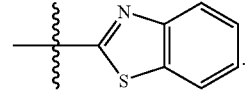

Another exemplary embodiment may be directed to a compound of formula (I) wherein $R^2$ is

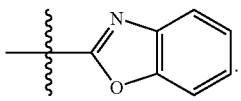

Another exemplary embodiment may be directed to a compound of formula (I) wherein $R^2$ is

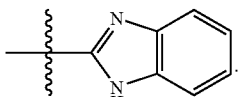

Another exemplary embodiment may be directed to a compound of formula (I) wherein $R^2$ is

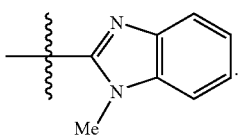

Another exemplary embodiment may be directed to a more specific version of the compound of formula (I), namely to a compound of formula (II):

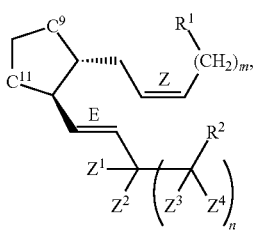

or an equivalent thereof, or a hydrate, solvate, or a pharmaceutically acceptable salt thereof.

Another exemplary embodiment may be directed to a more specific version of the compound of formula (I), namely to a compound of formula (III):

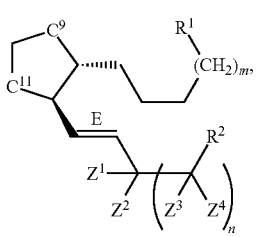

or an equivalent thereof, or a hydrate, solvate, or a pharmaceutically acceptable salt thereof.

Another exemplary embodiment may be directed to a more specific version of the compound of formula (I), namely to a compound of formula (IV):

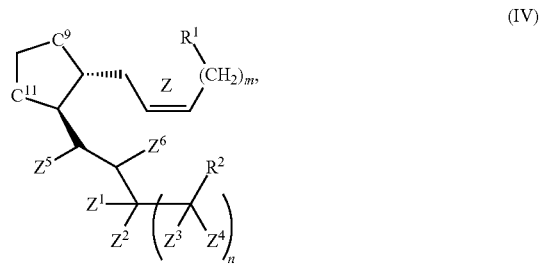

or an equivalent thereof, or a hydrate, solvate, or a pharmaceutically acceptable salt thereof.

Another exemplary embodiment may be directed to a more specific version of the compound of formula (I), namely to a compound of formula (V):

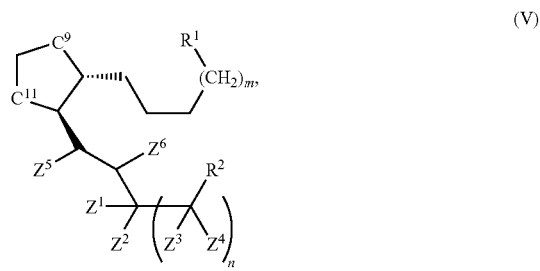

or an equivalent thereof, or a hydrate, solvate, or a pharmaceutically acceptable salt thereof.

Another exemplary embodiment may be a more specific compound of formula (I) selected from the group consisting of: (Z)-7-((1R,2R,3R)-2-((E)-3-(benzo[b]thiophen-2-yl)-3,3-difluoroprop-1-enyl)-3-hydroxy-5-oxocyclopentyl)hept-5-enoic acid; (Z)-7-((1R,2R,3R)-2-((E)-3-(benzo[b]thiophen-2-yl)-3-methylbut-1-enyl)-3-hydroxy-5-oxocyclopentyl)hept-5-enoic acid; (Z)-7-((1R,2R,3R)-2-((E)-3-(benzo[b]thiophen-2-yl)-3-oxoprop-1-enyl)-3-hydroxy-5-oxocyclopentyl)hept-5-enoic acid; (Z)-7-((1R,2R,3R)-2-((R)-3-(benzo[b]thiophen-2-yl)-3-hydroxypropyl)-3-hydroxy-5-oxocyclopentyl)hept-5-enoic acid; (Z)-7-((1R,2R,3R)-2-((R,E)-3-(1H-benzo[d]imidazol-2-yl)-3-hydroxyprop-1-enyl)-3-hydroxy-5-oxocyclopentyl)hept-5-enoic acid; (Z)-7-((1R,2R,3R)-2-((R,E)-3-(benzo[b]thiophen-2-yl)-3-hydroxybut-1-enyl)-3-hydroxy-5-oxocyclopentyl)hept-5-enoic acid; (Z)-7-((1R,2R,3R)-2-((R,E)-3-(benzo[b]thiophen-2-yl)-3-hydroxyprop-1-enyl)-3-hydroxy-5-oxocyclopentyl)hept-5-enoic acid; (Z)-7-((1R,2R,3R)-2-((R,E)-3-(benzo[d]oxazol-2-yl)-3-hydroxyprop-1-enyl)-3-hydroxy-5-oxocyclopentyl)hept-5-enoic acid; (Z)-7-((1R,2R,3R)-2-((R,E)-3-(benzo[d]thiazol-2-yl)-3-hydroxyprop-1-enyl)-3-hydroxy-5-oxocyclopentyl)hept-5-enoic acid; (Z)-7-((1R,2R,3R)-2-((S,E)-5-(2,3-dihydro-1H-inden-2-yl)-3-hydroxypent-1-enyl)-3-hydroxy-5-oxocyclopentyl)hept-5-enoic acid; (Z)-7-((1R,2R,3R)-2-((S,E)-6-(2,3-dihydro-1H-inden-2-yl)-3-hydroxyhex-1-enyl)-3-hydroxy-5-oxocyclopentyl)hept-5-enoic acid; (Z)-7-((1R,2R,3R)-2-((S,E)-6-(benzo[b]thiophen-2-yl)-3-hydroxyhex-1-enyl)-3-hydroxy-5-oxocyclopentyl)hept-5-enoic acid; (Z)-7-((1R,2R,3R)-3-hydroxy-2-((R,E)-3-hydroxy-3-(1-methyl- 1H-benzo[d]imidazol-2-yl)prop-1-enyl)-5-oxocyclopentyl) hept-5-enoic acid; (Z)-7-((1R,2R,3R)-3-hydroxy-2-((R,E)-3-hydroxy-3-(pyridin-2-yl)prop-1-enyl)-5-oxocyclopentyl) hept-5-enoic acid; 7-((1R,2R,3R)-2-((S,E)-3-(2,3-dihydro-1H-inden-2-yl)-3-hydroxyprop-1-enyl)-3-hydroxy-5-oxocyclopentyl)heptanoic acid; 7-((1R,2R,3R)-2-((R,E)-3-(benzo[b]thiophen-2-yl)-3-hydroxyprop-1-enyl)-3-hydroxy-5-oxocyclopentyl)heptanoic acid; 7-((1R,2R,3R)-2-((R)-3-(Benzo[b]thiophen-2-yl)-3-hydroxypropyl)-3-hydroxy-5-oxocyclopentyl)heptanoic acid; and 7-((1R,2R,3R)-2-((R)-5-(benzo[b]thiophen-2-yl)-3-hydroxypentyl)-3-hydroxy-5-oxocyclopentyl)heptanoic acid; (Z)-7-((1R,2R,3R)-2-(3,3-difluoro-4-phenoxybutyl)-3-hydroxy-5-oxocyclopentyl)hept-5-enoic acid; (Z)-7-((1R,2R,3R)-2-((E)-3-(benzo[b]thiophen-2-yl)-3-hydroxybut-1-enyl)-3-hydroxy-5-oxocyclopentyl)hept-5-enoic acid; or an equivalent thereof, or a ($C_1$-$C_6$)-alkyl ester thereof, or an N—($C_1$-$C_6$)-alkyl amide thereof, or an N-methylsulfonyl amide thereof, or a hydrate, solvate, or a pharmaceutically acceptable salt thereof.

Another exemplary embodiment may be a more specific compound of formula (I) selected from the group consisting of: (Z)-7-((1R,2R,5S)-2-((E)-3-(benzo[b]thiophen-2-yl)-3,3-difluoroprop-1-enyl)-5-hydroxy-3-oxocyclopentyl)hept-5-enoic acid; (Z)-7-((1R,2R,5S)-2-((E)-3-(benzo[b]thiophen-2-yl)-3-methylbut-1-enyl)-5-hydroxy-3-oxocyclopentyl)hept-5-enoic acid; (Z)-7-((1R,2R,5S)-2-((E)-3-(benzo[b]thiophen-2-yl)-3-oxoprop-1-enyl)-5-hydroxy-3-oxocyclopentyl)hept-5-enoic acid; (Z)-7-((1R,2R,5S)-2-((R)-3-(benzo[b]thiophen-2-yl)-3-hydroxypropyl)-5-hydroxy-3-oxocyclopentyl)hept-5-enoic acid; (Z)-7-((1R,2R,5S)-2-((R,E)-3-(1H-benzo[d]imidazol-2-yl)-3-hydroxyprop-1-enyl)-5-hydroxy-3-oxocyclopentyl)hept-5-enoic acid; (Z)-7-((1R,2R,5S)-2-((R,E)-3-(benzo[b]thiophen-2-yl)-3-hydroxybut-1-enyl)-5-hydroxy-3-oxocyclopentyl)hept-5-enoic acid; (Z)-7-((1R,2R,5S)-2-((R,E)-3-(benzo[b]thiophen-2-yl)-3-hydroxyprop-1-enyl)-5-hydroxy-3-oxocyclopentyl)hept-5-enoic acid; (Z)-7-((1R,2R,5S)-2-((R,E)-3-(benzo[d]oxazol-2-yl)-3-hydroxyprop-1-enyl)-5-hydroxy-3-oxocyclopentyl)hept-5-enoic acid; (Z)-7-((1R,2R,5S)-2-((R,E)-3-(benzo[d]thiazol-2-yl)-3-hydroxyprop-1-enyl)-5-hydroxy-3-oxocyclopentyl)hept-5-enoic acid; (Z)-7-((1R,2R,5S)-2-((S,E)-5-(2,3-dihydro-1H-inden-2-yl)-3-hydroxypent-1-enyl)-5-hydroxy-3-oxocyclopentyl)hept-5-enoic acid; (Z)-7-((1R,2R,5S)-2-((S,E)-6-(2,3-dihydro-1H-inden-2-yl)-3-hydroxyhex-1-enyl)-5-hydroxy-3-oxocyclopentyl)hept-5-enoic acid; (Z)-7-((1R,2R,5S)-2-((S,E)-6-(benzo[b]thiophen-2-yl)-3-hydroxyhex-1-enyl)-5-hydroxy-3-oxocyclopentyl)hept-5-enoic acid; (Z)-7-((1R,2R,5S)-5-hydroxy-2-((R,E)-3-hydroxy-3-(1-methyl-1H-benzo[d]imidazol-2-yl)prop-1-enyl)-3-oxocyclopentyl)hept-5-enoic acid; (Z)-7-((1R,2R,5S)-5-hydroxy-2-((R,E)-3-hydroxy-3-(pyridin-2-yl)prop-1-enyl)-3-oxocyclopentyl)hept-5-enoic acid; 7-((1R,2R,5S)-2-((S,E)-3-(2,3-dihydro-1H-inden-2-yl)-3-hydroxyprop-1-enyl)-5-hydroxy-3-oxocyclopentyl)heptanoic acid, and 7-((1R,2R,5S)-2-((R)-5-(benzo[b]thiophen-2-yl)-3-hydroxypentyl)-5-hydroxy-3-oxocyclopentyl)heptanoic acid; or an equivalent thereof, or a ($C_1$-$C_6$)-alkyl ester thereof, or an N—($C_1$-$C_6$)-alkyl amide thereof, or an N-methylsulfonyl amide thereof, or a hydrate, solvate, or a pharmaceutically acceptable salt thereof.

Another exemplary embodiment may be a more specific compound of formula (I) selected from the group consisting of: (Z)-7-((1R,2R)-2-((E)-3-(benzo[b]thiophen-2-yl)-3,3-difluoroprop-1-enyl)-3-methylene-5-oxocyclopentyl)hept-5-enoic acid and its tautomer (Z)-7-((1R,2R)-2-((E)-3-(benzo[b]thiophen-2-yl)-3,3-difluoroprop-1-enyl)-3-methyl-5-oxocyclopent-3-enyl)hept-5-enoic acid; (Z)-7-((1R,2R)-2-((E)-3-(benzo[b]thiophen-2-yl)-3-methylbut-1-enyl)-3-methylene-5-oxocyclopentyl)hept-5-enoic acid and its tautomer (Z)-7-((1R,2R)-2-((E)-3-(benzo[b]thiophen-2-yl)-3-methylbut-1-enyl)-3-methyl-5-oxocyclopent-3-enyl)hept-5-enoic acid; (Z)-7-((1R,2R)-2-((E)-3-(benzo[b]thiophen-2-yl)-3-oxoprop-1-enyl)-3-methylene-5-oxocyclopentyl)hept-5-enoic acid and its tautomer (Z)-7-((1R,2R)-2-((E)-3-(benzo[b]thiophen-2-yl)-3-oxoprop-1-enyl)-3-methyl-5-oxocyclopent-3-enyl)hept-5-enoic acid; (Z)-7-((1R,2R)-2-((R)-3-(benzo[b]thiophen-2-yl)-3-hydroxypropyl)-3-methylene-5-oxocyclopentyl)hept-5-enoic acid and its tautomer (Z)-7-((1R,2R)-2-((R)-3-(benzo[b]thiophen-2-yl)-3-hydroxypropyl)-3-methyl-5-oxocyclopent-3-enyl)hept-5-enoic acid; (Z)-7-((1R,2R)-2-((R,E)-3-(1H-benzo[d]imidazol-2-yl)-3-hydroxyprop-1-enyl)-3-methylene-5-oxocyclopentyl)hept-5-enoic acid and its tautomer (Z)-7-((1R,2R)-2-((R,E)-3-(1H-benzo[d]imidazol-2-yl)-3-hydroxyprop-1-enyl)-3-methyl-5-oxocyclopent-3-enyl) hept-5-enoic acid; (Z)-7-((1R,2R)-2-((R,E)-3-(benzo[b]thiophen-2-yl)-3-hydroxybut-1-enyl)-3-methylene-5-oxocyclopentyl)hept-5-enoic acid and its tautomer (Z)-7-((1R,2R)-2-((R,E)-3-(benzo[b]thiophen-2-yl)-3-hydroxybut-1-enyl)-3-methyl-5-oxocyclopent-3-enyl)hept-5-enoic acid; (Z)-7-((1R,2R)-2-((R,E)-3-(benzo[b]thiophen-2-yl)-3-hydroxyprop-1-enyl)-3-methylene-5-oxocyclopentyl)hept-5-enoic acid and its tautomer (Z)-7-((1R,2R)-2-((R,E)-3-(benzo[b]thiophen-2-yl)-3-hydroxyprop-1-enyl)-3-methyl-5-oxocyclopent-3-enyl) hept-5-enoic acid; (Z)-7-((1R,2R)-2-((R,E)-3-(benzo[d]oxazol-2-yl)-3-hydroxyprop-1-enyl)-3-methylene-5-oxocyclopentyl)hept-5-enoic acid and its tautomer (Z)-7-((1R,2R)-2-((R,E)-3-(benzo[d]oxazol-2-yl)-3-hydroxyprop-1-enyl)-3-methyl-5-oxocyclopent-3-enyl)hept-5-enoic acid; (Z)-7-((1R,2R)-2-((R,E)-3-(benzo[d]thiazol-2-yl)-3-hydroxyprop-1-enyl)-3-methylene-5-oxocyclopentyl)hept-5-enoic acid and its tautomer (Z)-7-((1R,2R)-2-((R,E)-3-(benzo[d]thiazol-2-yl)-3-hydroxyprop-1-enyl)-3-methyl-5-oxocyclopent-3-enyl)hept-5-enoic acid; (Z)-7-((1R,2R)-2-((R,E)-3-hydroxy-3-(1-methyl-1H-benzo[d]imidazol-2-yl)prop-1-enyl)-3-methylene-5-oxocyclopentyl)hept-5-enoic acid and its tautomer (Z)-7-((1R,2R)-2-((R,E)-3-hydroxy-3-(1-methyl-1H-benzo[d]imidazol-2-yl)prop-1-enyl)-3-methyl-5-oxocyclopent-3-enyl)hept-5-enoic acid; (Z)-7-((1R,2R)-2-((R,E)-3-hydroxy-4-(3-(trifluoromethyl)phenoxy)but-1-enyl)-3-methylene-5-oxocyclopentyl)hept-5-enoic acid and its tautomer (Z)-7-((1R,2R)-2-((R,E)-3-hydroxy-4-(3-(trifluoromethyl)phenoxy)but-1-enyl)-3-methyl-5-oxocyclopent-3-enyl)hept-5-enoic acid; (Z)-7-((1R,2R)-2-((S,E)-5-(2,3-dihydro-1H-inden-2-yl)-3-hydroxypent-1-enyl)-3-methylene-5-oxocyclopentyl)hept-5-enoic acid and its tautomer (Z)-7-((1R,2R)-2-((S,E)-5-(2,3-dihydro-1H-inden-2-yl)-3-hydroxypent-1-enyl)-3-methyl-5-oxocyclopent-3-enyl)hept-5-enoic acid; (Z)-7-((1R,2R)-2-((S,E)-6-(2,3-dihydro-1H-inden-2-yl)-3-hydroxyhex-1-enyl)-3-methylene-5-oxocyclopentyl)hept-5-enoic acid and its tautomer (Z)-7-((1R,2R)-2-((S,E)-6-(2,3-dihydro-1H-inden-2-yl)-3-hydroxyhex-1-enyl)-3-methyl-5-oxocyclopent-3-enyl)hept-5-enoic acid; (Z)-7-((1R,2R)-2-((S,E)-6-(benzo[b]thiophen-2-yl)-3-hydroxyhex-1-enyl)-3-methylene-5-oxocyclopentyl)hept-5-enoic acid and its tautomer (Z)-7-((1R,2R)-2-((S,E)-6-(benzo[b]thiophen-2-yl)-3-hydroxyhex-1-enyl)-3-methyl-5-oxocyclopent-3-enyl)hept-5-enoic acid; 7-((1R,2R)-2-((S,E)-3-(2,3-dihydro-1H-inden-2-yl)-3-hydroxyprop-1-enyl)-3-methylene-5-oxocyclopentyl)heptanoic acid and its tautomer 7-((1R,2R)-2-((S,E)-3-(2,3-dihydro-1H-inden-2-yl)-3-hydroxyprop-1- enyl)-3-methyl-5-oxocyclopent-3-enyl)heptanoic acid; and 7-((1R,2R)-2-((R)-3-(benzo[b]thiophen-2-yl)-3-hydroxypropyl)-3-methylene-5-oxocyclopentyl)heptanoic acid and its tautomer 7-((1R,2R)-2-((R)-3-(benzo[b]thiophen-2-yl)-3-hydroxypropyl)-3-methyl-5-oxocyclopent-3-enyl)heptanoic acid; or an equivalent thereof, or a ($C_1$-$C_6$)-alkyl ester thereof, or an N—($C_1$-$C_6$)-alkyl amide thereof, or an N-methylsulfonyl amide thereof, or a hydrate, solvate, or a pharmaceutically acceptable salt thereof.

Another exemplary embodiment may be a more specific compound of formula (I) selected from the group consisting of: (Z)-7-((1R,2R)-2-((R,E)-3-(benzo[b]thiophen-2-yl)-3-hydroxyprop-1-enyl)-3,3-difluoro-5-oxocyclopentyl)hept-5-enoic acid and its tautomer (Z)-7-((1R,5R)-5-((R,E)-3-(benzo[b]thiophen-2-yl)-3-hydroxyprop-1-enyl)-2-methyl-4-oxocyclopent-2-enyl)hept-5-enoic acid; (Z)-7-((1R,2R)-2-((R,E)-3-(benzo[b]thiophen-2-yl)-3-hydroxyprop-1-enyl)-5-methylene-3-oxocyclopentyl)hept-5-enoic acid; (Z)-7-((1R,2R,3R)-2-((R,E)-3-(benzo[b]thiophen-2-yl)-3-hydroxyprop-1-enyl)-3-fluoro-5-oxocyclopentyl)hept-5-enoic acid; (Z)-7-((1R,2R,3R)-2-((R,E)-3-(benzo[b]thiophen-2-yl)-3-hydroxyprop-1-enyl)-3-hydroxy-5-methylenecyclopentyl)hept-5-enoic acid; (Z)-7-((1R,2R,3S)-2-((R,E)-3-(benzo[b]thiophen-2-yl)-3-hydroxyprop-1-enyl)-3-fluoro-5-oxocyclopentyl)hept-5-enoic acid; (Z)-7-((1R,2R,5R)-2-((R,E)-3-(benzo[b]thiophen-2-yl)-3-hydroxyprop-1-enyl)-5-fluoro-3-oxocyclopentyl)hept-5-enoic acid; (Z)-7-((1R,2R,5S)-2-((R,E)-3-(benzo[b]thiophen-2-yl)-3-hydroxyprop-1-enyl)-3,3-difluoro-5-hydroxycyclopentyl)hept-5-enoic acid; (Z)-7-((1R,2R,5S)-2-((R,E)-3-(benzo[b]thiophen-2-yl)-3-hydroxyprop-1-enyl)-5-fluoro-3-oxocyclopentyl)hept-5-enoic acid; (Z)-7-((1R,2R,5S)-2-((R,E)-3-(benzo[b]thiophen-2-yl)-3-hydroxyprop-1-enyl)-5-hydroxy-3-methylenecyclopentyl)hept-5-enoic acid; (Z)-7-((1R,4R,5R)-5-((R,E)-3-(benzo[b]thiophen-2-yl)-3-hydroxyprop-1-enyl)-2,2-difluoro-4-hydroxycyclopentyl)hept-5-enoic acid, and (Z)-7-((1R,5R)-5-((R,E)-3-(benzo[b]thiophen-2-yl)-3-hydroxyprop-1-enyl)-2,2-difluoro-4-oxocyclopentyl)hept-5-enoic acid; or an equivalent thereof, or a ($C_1$-$C_6$)-alkyl ester thereof, or an N—($C_1$-$C_6$)-alkyl amide thereof, or an N-methylsulfonyl amide thereof, or a hydrate, solvate, or a pharmaceutically acceptable salt thereof.

Another exemplary embodiment may be a more specific compound of formula (I) selected from the group consisting of: 7-((1R,2R)-2-((R,E)-3-(benzo[b]thiophen-2-yl)-3-hydroxyprop-1-enyl)-3,3-difluoro-5-oxocyclopentyl)heptanoic acid and its tautomer 7-((1R,5R)-5-((R,E)-3-(benzo[b]thiophen-2-yl)-3-hydroxyprop-1-enyl)-2-methyl-4-oxocyclopent-2-enyl)heptanoic acid; 7-((1R,2R)-2-((R,E)-3-(benzo[b]thiophen-2-yl)-3-hydroxyprop-1-enyl)-5-methylene-3-oxocyclopentyl)heptanoic acid; 7-((1R,2R,3R)-2-((R,E)-3-(benzo[b]thiophen-2-yl)-3-hydroxyprop-1-enyl)-3-fluoro-5-oxocyclopentyl)heptanoic acid; 7-((1R,2R,3R)-2-((R,E)-3-(benzo[b]thiophen-2-yl)-3-hydroxyprop-1-enyl)-3-hydroxy-5-methylenecyclopentyl)heptanoic acid; 7-((1R,2R,3S)-2-((R,E)-3-(benzo[b]thiophen-2-yl)-3-hydroxyprop-1-enyl)-3-fluoro-5-oxocyclopentyl)heptanoic acid; 7-((1R,2R,5R)-2-((R,E)-3-(benzo[b]thiophen-2-yl)-3-hydroxyprop-1-enyl)-5-fluoro-3-oxocyclopentyl)heptanoic acid; 7-((1R,2R,5S)-2-((R,E)-3-(benzo[b]thiophen-2-yl)-3-hydroxyprop-1-enyl)-3,3-difluoro-5-hydroxycyclopentyl)heptanoic acid; 7-((1R,2R,5S)-2-((R,E)-3-(benzo[b]thiophen-2-yl)-3-hydroxyprop-1-enyl)-5-fluoro-3-oxocyclopentyl)heptanoic acid; 7-((1R,2R,5S)-2-((R,E)-3-(benzo[b]thiophen-2-yl)-3-hydroxyprop-1-enyl)-5-hydroxy-3-methylenecyclopentyl)heptanoic acid; 7-((1R,4R,5R)-5-((R,E)-3-(benzo[b]thiophen-2-yl)-3-hydroxyprop-1-enyl)-2,2-difluoro-4-hydroxycyclopentyl)heptanoic acid, and 7-((1R,5R)-5-((R,E)-3-(benzo[b]thiophen-2-yl)-3-hydroxyprop-1-enyl)-2,2-difluoro-4-oxocyclopentyl)heptanoic acid; or an equivalent thereof, or a ($C_1$-$C_6$)-alkyl ester thereof, or an N—($C_1$-$C_6$)-alkyl amide thereof, or an N-methylsulfonyl amide thereof, or a hydrate, solvate, or a pharmaceutically acceptable salt thereof.

Another exemplary embodiment may be a more specific compound of formula (I) selected from the group consisting of: (Z)-7-((1R,2R)-2-((R)-3-(benzo[b]thiophen-2-yl)-3-hydroxypropyl)-3,3-difluoro-5-oxocyclopentyl)hept-5-enoic acid; (Z)-7-((1R,2R)-2-((R)-3-(benzo[b]thiophen-2-yl)-3-hydroxypropyl)-5-methylene-3-oxocyclopentyl)hept-5-enoic acid and its tautomer (Z)-7-((1R,5R)-5-((R)-3-(benzo[b]thiophen-2-yl)-3-hydroxypropyl)-2-methyl-4-oxocyclopent-2-enyl)hept-5-enoic acid; (Z)-7-((1R,2R,3R)-2-((R)-3-(benzo[b]thiophen-2-yl)-3-hydroxypropyl)-3-fluoro-5-oxocyclopentyl)hept-5-enoic acid; (Z)-7-((1R,2R,3R)-2-((R)-3-(benzo[b]thiophen-2-yl)-3-hydroxypropyl)-3-hydroxy-5-methylenecyclopentyl)hept-5-enoic acid; (Z)-7-((1R,2R,3S)-2-((R)-3-(benzo[b]thiophen-2-yl)-3-hydroxypropyl)-3-fluoro-5-oxocyclopentyl)hept-5-enoic acid; (Z)-7-((1R,2R,5R)-2-((R)-3-(benzo[b]thiophen-2-yl)-3-hydroxypropyl)-5-fluoro-3-oxocyclopentyl)hept-5-enoic acid; (Z)-7-((1R,2R,5S)-2-((R)-3-(benzo[b]thiophen-2-yl)-3-hydroxypropyl)-3,3-difluoro-5-hydroxycyclopentyl)hept-5-enoic acid; (Z)-7-((1R,2R,5S)-2-((R)-3-(benzo[b]thiophen-2-yl)-3-hydroxypropyl)-5-fluoro-3-oxocyclopentyl)hept-5-enoic acid; (Z)-7-((1R,2R,5S)-2-((R)-3-(benzo[b]thiophen-2-yl)-3-hydroxypropyl)-5-hydroxy-3-methylenecyclopentyl)hept-5-enoic acid; (Z)-7-((1R,4R,5R)-5-((R)-3-(benzo[b]thiophen-2-yl)-3-hydroxypropyl)-2,2-difluoro-4-hydroxycyclopentyl)hept-5-enoic acid, and (Z)-7-((1R,5R)-5-((R)-3-(benzo[b]thiophen-2-yl)-3-hydroxypropyl)-2,2-difluoro-4-oxocyclopentyl)hept-5-enoic acid; or an equivalent thereof, or a ($C_1$-$C_6$)-alkyl ester thereof, or an N—($C_1$-$C_6$)-alkyl amide thereof, or an N-methylsulfonyl amide thereof, or a hydrate, solvate, or a pharmaceutically acceptable salt thereof.

Another exemplary embodiment may be a more specific compound of formula (I) selected from the group consisting of: 7-((1R,2R)-2-((R)-3-(benzo[b]thiophen-2-yl)-3-hydroxypropyl)-3,3-difluoro-5-oxocyclopentyl)heptanoic acid; 7-((1R,2R)-2-((R)-3-(benzo[b]thiophen-2-yl)-3-hydroxypropyl)-5-methylene-3-oxocyclopentyl)heptanoic acid and its tautomer 7-((1R,5R)-5-((R)-3-(benzo[b]thiophen-2-yl)-3-hydroxypropyl)-2-methyl-4-oxocyclopent-2-enyl)heptanoic acid; 7-((1R,2R,3R)-2-((R)-3-(benzo[b]thiophen-2-yl)-3-hydroxypropyl)-3-fluoro-5-oxocyclopentyl)heptanoic acid; 7-((1R,2R,3R)-2-((R)-3-(benzo[b]thiophen-2-yl)-3-hydroxypropyl)-3-hydroxy-5-methylenecyclopentyl)heptanoic acid; 7-((1R,2R,3S)-2-((R)-3-(benzo[b]thiophen-2-yl)-3-hydroxypropyl)-3-fluoro-5-oxocyclopentyl)heptanoic acid; 7-((1R,2R,5R)-2-((R)-3-(benzo[b]thiophen-2-yl)-3-hydroxypropyl)-5-fluoro-3-oxocyclopentyl)heptanoic acid; 7-((1R,2R,5S)-2-((R)-3-(benzo[b]thiophen-2-yl)-3-hydroxypropyl)-3,3-difluoro-5-hydroxycyclopentyl)heptanoic acid; 7-((1R,2R,5S)-2-((R)-3-(benzo[b]thiophen-2-yl)-3-hydroxypropyl)-5-fluoro-3-oxocyclopentyl)heptanoic acid; 7-((1R,2R,5S)-2-((R)-3-(benzo[b]thiophen-2-yl)-3-hydroxypropyl)-5-hydroxy-3-methylenecyclopentyl)heptanoic acid; 7-((1R,4R,5R)-5-((R)-3-(benzo[b]thiophen-2-yl)-3-hydroxypropyl)-2,2-difluoro-4-hydroxycyclopentyl)heptanoic acid, and 7-((1R,5R)-5-((R)-3-(benzo[b]thiophen-2-yl)-3-hydroxypropyl)-2,2-difluoro-4-oxocyclopentyl)heptanoic acid; or an equivalent thereof, or a ($C_1$-$C_6$)-alkyl ester thereof, or an N—($C_1$-$C_6$)-alkyl amide thereof, or an N-methylsulfonyl amide thereof, or a hydrate, solvate, or a pharmaceutically acceptable salt thereof.

The exemplary embodiments may also be directed to a method of preventing or treating a disease or condition mediated at least in part by agonism of an EP receptor, in a subject in need of such treatment, comprising administering to the subject a therapeutically effective amount of a compound of any of the exemplary embodiments formula (I), or a pharmaceutically acceptable salt, hydrate, or solvate thereof; the use of a compound of any of the exemplary embodiments of formula (I), or a pharmaceutically acceptable salt, hydrate, or solvate thereof, for the manufacture of a medicament for preventing or treating a disease or condition mediated at least in part by agonism of an EP receptor; a compound of any of the exemplary embodiments of formula (I), or a pharmaceutically acceptable salt, hydrate, or solvate thereof, for use as a medicament; a compound of any of the exemplary embodiments of formula (I), or a pharmaceutically acceptable salt, hydrate, or solvate thereof, for use in the prevention or treatment of a disease or condition mediated at least in part by agonism of an EP receptor; a pharmaceutical composition comprising a compound of any of the exemplary embodiments of formula (I), or a pharmaceutically acceptable salt, hydrate, or solvate thereof, and a pharmaceutically acceptable excipient; a pharmaceutical composition for the prevention and treatment of a disease or condition mediated at least in part by agonism of an EP receptor comprising a compound of any of the exemplary embodiments formula (I), or a pharmaceutically acceptable salt, hydrate, or solvate thereof.

The diseases and conditions mediated at least in part by agonism of an EP receptor may include allergy and allergic inflammation. Diseases and conditions of this kind may be allergic respiratory conditions such as allergic rhinitis, nasal congestion, rhinorrhea, perennial rhinitis, nasal inflammation, asthma of all types, chronic obstructive pulmonary disease (COPD), chronic or acute bronchoconstriction, chronic bronchitis, small airways obstruction, emphysema, chronic eosinophilic pneumonia, adult respiratory distress syndrome, exacerbation of airways hyper-reactivity consequent to other drug therapy, airways disease that may be associated with pulmonary hypertension, acute lung injury, bronchiectasis, sinusitis, allergic conjunctivitis, or atopic dermatitis, particularly asthma or chronic obstructive pulmonary disease.

Types of asthma may include atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, bronchitic asthma, emphysematous asthma, exercise-induced asthma, exertion asthma, allergen-induced asthma, cold air induced asthma, occupational asthma, infective asthma caused by bacterial, fungal, protozoal, or viral infection, non-allergic asthma, incipient asthma, wheezy infant syndrome, and bronchiolytis.

Included in the use of the compounds of any of the exemplary embodiments of formula (I) for the treatment of asthma, may be palliative treatment for the symptoms and conditions of asthma such as wheezing, coughing, shortness of breath, tightness in the chest, shallow or fast breathing, nasal flaring (nostril size increases with breathing), retractions (neck area and between or below the ribs moves inward with breathing), cyanosis (gray or bluish tint to skin, beginning around the mouth), runny or stuffy nose, and headache.

The exemplary embodiments may also be directed to any of the uses, methods, or compositions as defined above wherein the compound of any of the exemplary embodiments of formula (I), or a pharmaceutically acceptable salt, hydrate, or solvate thereof, may be used in combination with another pharmacologically active compound. Specific combinations useful for the treatment of allergy or asthma may include combinations comprising a compound of any of the exemplary embodiments of formula (I), or a pharmaceutically acceptable salt, hydrate, or solvate thereof, and (i) a glucocorticosteroid or DAGR (dissociated agonist of the corticoid receptor); (ii) a $\beta_2$ agonist, an example of which is a long-acting $\beta_2$ agonist; (iii) a muscarinic M3 receptor antagonist or anticholinergic agent; (iv) a histamine receptor antagonist or inverse agonist, which may be an H1 or an H3 antagonist or inverse agonist; (v) a 5-lipoxygenase inhibitor; (vi) a thromboxane inhibitor; (vii) an $LTD_4$ inhibitor; (viii) a kinase inhibitor; or (ix) a vaccine. Generally, the compounds of the combination may be administered together as a formulation in association with one or more pharmaceutically acceptable excipients.

Other diseases and conditions that may be mediated, at least in part, by agonism of an EP receptor are influenza, bone fracture healing, bone disease, glaucoma, ocular hypertension, dysmenorrhoea, pre-term labor, immune disorders, osteoporosis, asthma, allergy, fertility, male sexual dysfunction female sexual dysfunction, periodontal disease, gastric ulcer, and renal disease. EP receptor agonists may also be useful for expansion of hematopoietic stem cell populations.

Besides being useful for human treatment, compounds of formula (I) may also be useful for veterinary treatment of companion animals, exotic animals, and farm animals.

When used in the present application, the following abbreviations have the meaning set out below: Ac is acetyl; ACN is acetonitrile; $BBr_3$ is boron tribromide; Bn is benzyl; $BnNH_2$ is benzylamine; BSA is bovine serum albumin; $CH_2Cl_2$ is dichloromethane; $CHCl_3$ is chloroform; $CDCl_3$ is deuterochloroform; DAST is diethylaminosulfur trifluoride; DCC is N,N'-dicyclohexylcarbodiimide; DCM is dichloromethane; DIBAL-His diisobutylaluminum hydride; DME is 1,2-dimethoxyethane; DMEM is Dulbecco's minimal essential medium; DMF is N,N-dimethylformamide; DMSO is dimethyl sulfoxide; DBU is 1,8-diazabicyclo[5.4.0]undec-7-ene; EDC/EDAC is N-(3-dimethylaminopropyl)-N'-ethylcarbodiimide hydrochloride; EDTA is ethylenediaminetetraacetic acid; EIA is enzyme immunoassay; Et is ethyl; $Et_3N$ is triethylamine; HOBt is 1-hydroxybenzotriazole; HBSS is Hank's balanced salt solution; IBMX is isobutylmethylxanthine; $^iPr$ is isopropyl; MCS is multiple cloning site; Me is methyl; MES is 2-(N-morpholino)ethanesulfonic acid; NaHMDS is sodium hexamethyldisilazane, also known as sodium bis(trimethylsilyl)amide; NMP is 1-methyl-2-pyrrolidinone; PCR is polymerase chain reaction; Ph is phenyl; $Pd(PPh_3)_4$ is tetrakis(triphenylphosphine)palladium; $PhB(OH)_2$ is benzeneboronic acid, also known as phenylboronic acid; PhMe is toluene; rt is room temperature; TBAF is tetrabutylammonium fluoride; TBDMS is tert-butyldimethylsilyl; TBDPS is tert-butyldiphenylsilyl; t-Bu is tert-butyl; TCA is trichloroacetic acid; THF is tetrahydrofuran; TMS is trimethylsilyl; and Tris-HCl is 2-amino-2-(hydroxymethyl)-1,3-propanediol hydrochloride.

Unless otherwise defined herein, scientific and technical terms used in connection with the exemplary embodiments shall have the meanings that are commonly understood by those of ordinary skill in the art.

Further, unless otherwise required by context, singular terms shall include pluralities and plural terms shall include the singular. Generally, nomenclature used in connection with, and techniques of chemistry and molecular biology described herein are those well known and commonly used in the art.

The phrase "therapeutically effective" is intended to qualify the amount of compound or pharmaceutical composition, or the combined amount of active ingredients in the case of combination therapy. This amount or combined amount may achieve the goal of treating the relevant condition.

The term "treatment," as used herein to describe the exemplary embodiments and unless otherwise qualified, means administration of the compound, pharmaceutical composition, or combination to effect preventative, palliative, supportive, restorative, or curative treatment. The term treatment encompasses any objective or subjective improvement in a subject with respect to a relevant condition or disease.

The term "preventative treatment," as used herein to describe the exemplary embodiments, means that the compound, pharmaceutical composition, or combination may be administered to a subject to inhibit or stop the relevant condition from occurring in a subject, particularly in a subject or member of a population that may be significantly predisposed to the relevant condition.

The term "palliative treatment," as used herein to describe the exemplary embodiments, means that the compound, pharmaceutical composition, or combination may be administered to a subject to remedy signs and/or symptoms of a condition, without necessarily modifying the progression of, or underlying etiology of, the relevant condition.

The term "supportive treatment," as used herein to describe the exemplary embodiments, means that the compound, pharmaceutical composition, or combination may be administered to a subject as part of a regimen of therapy, but that such therapy is not limited to administration of the compound, pharmaceutical composition, or combination. Unless otherwise expressly stated, supportive treatment may embrace preventative, palliative, restorative, or curative treatment, particularly when the compounds or pharmaceutical compositions are combined with another component of supportive therapy.

The term "restorative treatment," as used herein to describe the exemplary embodiments, means that the compound, pharmaceutical composition, or combination may be administered to a subject to modify the underlying progression or etiology of a condition. Non-limiting examples include an increase in forced expiratory volume in one second (FEV 1) for lung disorders, inhibition of progressive nerve destruction, reduction of biomarkers associated and correlated with diseases or disorders, a reduction in relapses, improvement in quality of life, and the like.

The term "curative treatment," as used herein to describe the exemplary embodiments, means that the compound, pharmaceutical composition, or combination may be administered to a subject for the purpose of bringing the disease or disorder into complete remission, or that the disease or disorder in undetectable after such treatment.

The term "alkyl," alone or in combination, means an acyclic radical, linear or branched, preferably containing from 1 to about 6 carbon atoms. Examples of such radicals include methyl, ethyl, n-propyl, isopropyl, n-butyl, isobutyl, sec-butyl, tert-butyl, pentyl, iso-amyl, hexyl, heptyl, octyl, and the like. Where no specific substitution is specified, alkyl radicals may be optionally substituted with groups consisting of hydroxy, sulfhydryl, methoxy, ethoxy, amino, cyano, chloro, and fluoro.

The carbon atom content of various hydrocarbon-containing moieties is indicated by a prefix designating a lower and upper number of carbon atoms in the moiety, that is, the prefix $C_i$-$C_j$ indicates a moiety of the integer "i" to the integer "j" carbon atoms, inclusive. Thus, for example, '($C_1$-$C_8$)-alkyl' refers to alkyl of one to eight carbon atoms, inclusive.

The terms "hydroxy" and "hydroxyl," as used herein, mean an OH radical.

The term "sulfhydryl," as used herein, means an SH radical.

The term "oxo" means a doubly bonded oxygen.

The term "alkoxy" means a radical comprising an alkyl radical that is bonded to an oxygen atom, such as a methoxy radical.

The term "aryl" means a fully unsaturated mono- or multi-ring cycloalkyl having a cyclic array of p-orbitals containing 4n+2 electrons, including, but not limited to, substituted or unsubstituted phenyl, naphthyl, or anthracenyl optionally fused to a carbocyclic radical wherein aryl may be optionally substituted with one or more substituents from the group consisting of halo, methoxy, ethoxy, ($C_1$-$C_6$)-alkyl, phenyl, O-phenyl, cyano, nitro, hydroxyl, sulfhydryl, or trifluoromethyl.

The term "halo," as used herein, means one of the following group consisting of fluoro, chloro, bromo, or iodo.

The terms "heterocycle", "heterocyclic ring system," and "heterocyclyl" refer to a saturated or unsaturated mono- or multi-ring cycloalkyl wherein one or more carbon atoms is replaced by N, S, or O. The terms "heterocycle", "heterocyclic ring system," and "heterocyclyl" include fully saturated ring structures such as piperazinyl, dioxanyl, tetrahydrofuranyl, oxiranyl, aziridinyl, morpholinyl, pyrrolidinyl, piperidinyl, thiazolidinyl, and others. The terms "heterocycle", "heterocyclic ring system," and "heterocyclyl" also include partially unsaturated ring structures such as dihydrofuranyl, pyrazolinyl, imidazolinyl, pyrrolinyl, chromanyl, dihydrothiphenyl, and others.

The term "heteroaryl" refers to an aromatic heterocyclic group. Heteroaryl is preferably: (a) a five-membered aromatic heterocyclic group containing either (i) 1-4 nitrogen atoms or (ii) 0-3 nitrogen atoms and 1 oxygen or 1 sulfur atom; (b) a six-membered aromatic heterocyclic group containing 1-3 nitrogen atoms; (c) a nine-membered bicyclic heterocyclic group containing either (i) 1-5 nitrogen atoms or (ii) 0-4 nitrogen atoms and 1 oxygen or 1 sulfur atom; or (d) a ten-membered bicyclic aromatic heterocyclic group containing 1-6 nitrogen atoms; each of said groups (a)-(d) being optionally substituted by one or more of ($C_1$-$C_6$)-alkyl, ($C_1$-$C_6$)-fluoroalkyl, ($C_3$-$C_6$)-cycloalkyl, hydroxy($C_3$-$C_6$)-cycloalkyl, ($C_2$-$C_6$)-alkenyl, ($C_2$-$C_6$)-alkynyl, halo, oxo, hydroxyl, ($C_1$-$C_6$)-alkoxy, sulfhydryl, —SMe, or cyano. Examples of "heteroaryl" include pyridyl, pyrimidinyl, pyridazinyl, pyrazinyl, thionyl, furanyl, pyrrolyl, pyrazolyl, imidazolyl, oxazolyl, isoxazolyl, thiazolyl, isothiazolyl, triazolyl, oxadiazolyl, thiadiazolyl, and tetrazolyl, optionally substituted as specified above.

In "heterocycle" or "heteroaryl," the point of attachment to the molecule of interest may be at a heteroatom or elsewhere within the ring.

The term "cycloalkyl" means a mono- or multi-ringed cycloalkyl wherein each ring contains three to ten carbon atoms, preferably three to six carbon atoms. "Cycloalkyl" is preferably a monocyclic cycloalkyl containing from three to six carbon atoms. Examples include cyclopropyl, cyclobutyl, cyclopentyl, and cyclohexyl.

The term "excipient" is used herein to describe any ingredient other than a compound of any of the exemplary embodiments of formula (I). The choice of excipient will to a large extent depend on factors such as the particular mode of administration, the effect of the excipient on solubility and stability, and the nature of the dosage form. The term "excipient" encompasses diluents, carrier, or adjuvant.

Pharmaceutically acceptable salts of the compounds of any of the exemplary embodiments of formula (I) include the acid addition and base salts thereof.

Suitable acid addition salts are formed by acids which form non-toxic salts. Examples include the acetate, adipate, aspartate, benzoate, besylate, bicarbonate/carbonate, bisulfate/sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, propionate, pyroglutamate, saccharate, stearate, succinate, tannate, tartrate, tosylate, trifluoroacetate, naphthalene-1,5-disulfonic acid, and xinofoate salts.

Suitable base salts are formed from bases which form non-toxic salts. Examples include the aluminum, arginine, benzathine, calcium, choline, diethylamine, diolamine, glycine, lysine, magnesium, meglumine, olamine, potassium, sodium, tromethamine, and zinc salts.

Hemisalts of acids and bases may also be formed, for example, hemisulfate and hemicalcium salts. For a review on suitable salts, see Handbook of Pharmaceutical Salts: Properties, Selection, and Use, by Stahl and Wermuth (Wiley-VCH, 2002).

The compounds of any of the exemplary embodiments of formula (I) may also exist in unsolvated and solvated forms. The term "solvate" is used herein to describe a molecular complex comprising the compound of any of the exemplary embodiments of formula (I), or a pharmaceutically acceptable salt thereof, and one or more pharmaceutically acceptable solvent molecules, for example, ethanol. The term "hydrate" is employed when said solvent is water.

Also included herein are multi-component complexes other than salts and solvates wherein the compound of any of the exemplary embodiments of formula (I) and at least one other component are present in stoichiometric or non-stoichiometric amounts.

The compounds of any exemplary embodiment of formula (I) may exist in a continuum of solid states ranging from fully amorphous to fully crystalline.

The compounds of any exemplary embodiment of formula (I) may also exist in a mesomorphic state (mesophase or liquid crystal) when subjected to suitable conditions. The mesomorphic state is intermediate between the true crystalline state and the true liquid state (either melt or solution).

Hereinafter all references to compounds of any exemplary embodiments of formula (I) include references to salts, solvates, multi-component complexes, and liquid crystals thereof and to solvates, multi-component complexes, and liquid crystals of salts thereof.

Also included herein are all polymorphs and crystal habits of compounds of any of the exemplary embodiments of formula (I), prodrugs, and isomers thereof (including optical, geometric, and tautomeric isomers) and isotopically-labeled forms thereof.

Compounds of any of the exemplary embodiments of formula (I) may be administered orally, topically, transdermally, intranasally, by inhalation, directly into the bloodstream, into muscle, into an internal organ, into the eye, into the ear, into the rectum, or by other means.

The compounds herein, their methods or preparation and their biological activity will appear more clearly from the examination of the following examples that are presented as an illustration only and are not to be considered as limiting the invention in its scope. Compounds herein are identified, for example, by the following analytical methods.

Mass spectra (MS) methods include positive electrospray ionization (ESI$^+$), negative electrospray ionization (ESI$^-$), positive atmospheric pressure chemical ionization (APCI$^+$), or negative atmospheric pressure chemical ionization (APCI$^-$).

300 MHz proton nuclear magnetic resonance spectra ($^1$H NMR) are recorded at ambient temperature using a Bruker (300 MHz) spectrometer. In the $^1$H NMR chemical shifts (δ) are indicated in parts per million (ppm) with reference to tetramethylsilane (TMS) as the internal standard.

EXAMPLES

Example 1

Preparation of (Z)-7-((1R,2R,3R)-2-(3,3-difluoro-4-phenoxybutyl)-3-hydroxy-5-oxocyclopentyl)hept-5-enoic acid

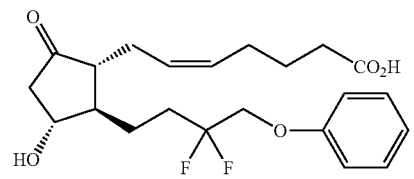

Step A: Preparation of (3aR,4R,5R,6aS)-2-oxo-4-((E)-3-oxo-4-phenoxybut-1-enyl)hexahydro-2H-cyclopent[b]furan-5-yl benzoate

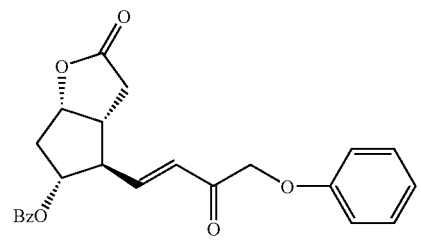

A 4-L reactor equipped with a mechanical stirrer, under nitrogen, was charged with (3aR,4R,5R,6aS)-4-formyl-2-oxohexahydro-2H-cyclopenta[b]furan-5-yl benzoate (Cayman Chemical Catalog #70030, 99.2 g, 0.362 mol) in dichloromethane and lithium chloride (16.7 g, 0.398 mol) dissolved in tetrahydrofuran. Dimethyl 2-oxo-3-phenoxypropylphosphonate (102.7 g, 0.398 mol) is added neat and rinsed with dichloromethane (50 mL). Some lithium chloride precipitated from solution when the THF and DCM solutions were mixed. The mixture was stirred under nitrogen and cooled to −20° C. After adding the phosphonate and subsequent stirring and cooling, the precipitated lithium chloride dissolved. After stirring for 2.5 hours, triethylamine (40.2 g, 0.398 mol) was added neat via addition funnel and the temperature was held at −5° C. and stirred at this temperature for 19 hours. The temperature was adjusted to 0° C. and treated with 5% aqueous citric acid and the layers were separated. The organic layer was dried over magnesium sulfate and filtered. The crude product was purified on silica gel, eluted with ethyl acetate-hexanes (1:1). The desired product precipitated from the product-rich fractions as a white fluffy solid. After further purification of mixed fractions, all the purified product crystallized from MTBE to afford the title intermediate (74.4 g, 50.6%) as a white solid.

Step B: Preparation of (3aR,4R,5R,6aS)-2-oxo-4-(3-oxo-4-phenoxybutyl)hexahydro-2H-cyclopenta[b]furan-5-yl benzoate

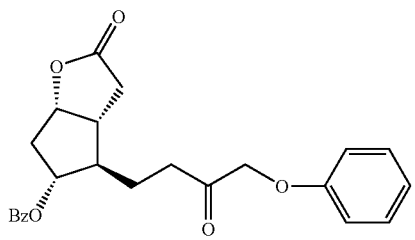

(3aR,4R,5R,6aS)-2-Oxo-4-((E)-3-oxo-4-phenoxybut-1-enyl)hexahydro-2H-cyclopenta[b]furan-5-yl benzoate, prepared in Step A, is dissolved in ethyl acetate and 10% Pd/C is added to the solution under a nitrogen atmosphere. The solution is flushed with hydrogen gas and subsequently stirred under a hydrogen atmosphere until starting material is consumed as judged by TLC. The crude reaction mixture is filtered through Celite and the solvent is removed under reduced pressure. The crude product is purified by flash chromatography on regular silica gel eluted with ethyl acetate-hexanes to afford the title intermediate.

Step C: Preparation of (3aR,4R,5R,6aS)-4-(3,3-difluoro-4-phenoxybutyl)-2-oxohexahydro-2H-cyclopenta[b]furan-5-yl benzoate

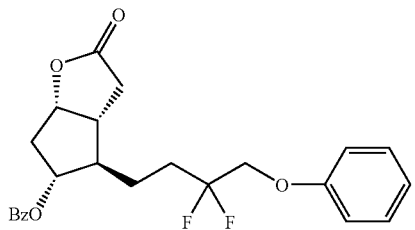

(3aR,4R,5R,6aS)-2-Oxo-4-(3-oxo-4-phenoxybutyl)hexahydro-2H-cyclopenta[b]furan-5-yl benzoate (limiting reagent, prepared in Step B) is dissolved in DCM (0.1 M) under a nitrogen atmosphere. The solution is cooled to 0° C. and DAST (2 molar equivalents) are added dropwise. The reaction mixture is allowed to slowly warm to room temperature. Stirring is continued until reaction progress ceases. The crude reaction mixture is transferred to a separatory funnel and saturated aqueous sodium bicarbonate is added in portions. The product is extracted with ethyl acetate and the aqueous layer is back-extracted with ethyl acetate. The combined organic layers are dried over sodium sulfate, filtered, and evaporated. The product is purified by flash chromatography on regular silica gel, eluted with ethyl acetate-hexanes (35:75). The pure fractions are combined and concentrated under reduced pressure to afford the title intermediate.

Step D: Preparation of (3aR,4R,5R,6aS)-4-(3,3-difluoro-4-phenoxybutyl)-5-hydroxyhexahydro-2H-cyclopenta[b]furan-2-one

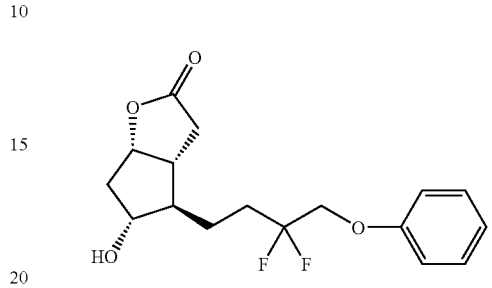

(3aR,4R,5R,6aS)-4-(3,3-Difluoro-4-phenoxybutyl)-2-oxohexahydro-2H-cyclopenta[b]furan-5-yl benzoate (prepared in Step C, 1.0 g, 2.4 mmol) is dissolved in methanol (0.2 M) and potassium carbonate (194 mg, 1.41 mmol) is added. The reaction mixture is stirred at room temperature and the progress is monitored by TLC every 30 minutes. After complete consumption of starting material, the reaction mixture is acidified with 5% KHSO$_4$ and diluted with brine. The product is extracted with ethyl acetate twice. The combined organic layers are dried over sodium sulfate, filtered and evaporated. The crude product is purified by flash chromatography on regular silica gel eluted with ethyl acetate-hexanes (1:1) to afford the title intermediate.

Step E: Preparation of (3aR,4R,5R,6aS)-4-(3,3-difluoro-4-phenoxybutyl)-5-(tetrahydro-2H-pyran-2-yloxy)hexahydro-2H-cyclopenta[b]furan-2-one

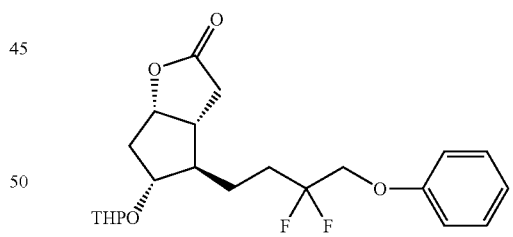

(3aR,4R,5R,6aS)-4-(3,3-Difluoro-4-phenoxybutyl)-5-hydroxyhexahydro-2H-cyclopenta[b]furan-2-one, prepared in Step D, is dissolved in DCM (0.1 M) under a nitrogen atmosphere. Dihydropyran (1.1 molar equivalents) is added, followed by a catalytic amount of p-toluenesulfonic acid. The reaction is stirred at room temperature under a nitrogen atmosphere and the reaction progress is monitored by TLC. Upon completion, brine is added to the reaction mixture and the layers are separated. The organic phase is dried over sodium sulfate, filtered, and the solvent is evaporated. The crude product is purified by flash chromatography on regular silica gel eluted with ethyl acetate-hexanes to afford the title intermediate.

Step F: Preparation of (3aR,4R,5R,6aS)-4-(3,3-difluoro-4-phenoxybutyl)-5-(tetrahydro-2H-pyran-2-yloxy)hexahydro-2H-cyclopenta[b]furan-2-ol

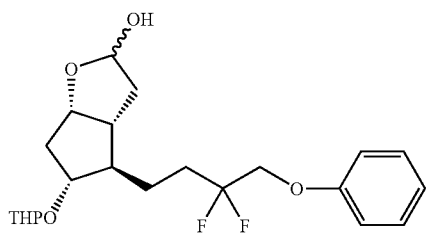

(3aR,4R,5R,6aS)-4-(3,3-Difluoro-4-phenoxybutyl)-5-(tetrahydro-2H-pyran-2-yloxy)hexahydro-2H-cyclopenta[b]furan-2-one, prepared in Step E, was dissolved in anhydrous THF (0.5 M) under nitrogen atmosphere and cooled to −78° C. A solution consisting of DIBAL-H (2 molar equivalents, 1 M in toluene) is added to the reaction mixture dropwise and stirred for 3 hours. Ethyl acetate (20 mL) is added and the mixture is stirred for an additional 5 minutes. The mixture is subsequently treated with 30% aqueous K, Na tartrate and stirred vigorously overnight. The layers are separated and the organic phase is filtered and concentrated under reduced pressure. The crude product is purified by flash chromatography on regular silica gel eluted with ethyl acetate-hexanes to afford the title intermediate.

Step G: Preparation of (Z)-7-((1R,2R,3R,5S)-2-(3,3-difluoro-4-phenoxybutyl)-5-hydroxy-3-(tetrahydro-2H-pyran-2-yloxy)cyclopentyl)hept-5-enoic Acid

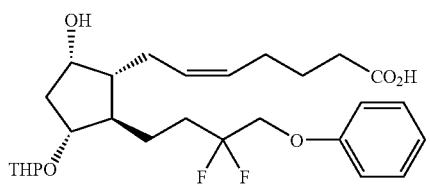

4-Carboxybutyltriphenylphosphonium bromide (3.5 molar equivalents) is suspended in anhydrous THF under a nitrogen atmosphere. Potassium tert-butoxide in THF (1 M, 7 molar equivalents) is added dropwise to the white suspension. The reaction mixture becomes bright red over the course of the addition. The mixture continues stirring for 30 minutes at room temperature and is subsequently cooled to −15° C. in an ice/NaCl bath. The lactol ((3aR,4R,5R,6aS)-4-(3,3-difluoro-4-phenoxybutyl)-5-(tetrahydro-2H-pyran-2-yloxy)hexahydro-2H-cyclopenta[b]furan-2-ol) (limiting reagent, prepared in Step F) is dissolved in THF and added dropwise to the ylide. The reaction mixture becomes lighter orange in color. The mixture continues stirring for 2 hours at −15° C. and is subsequently allowed to warm to room temperature and stir overnight as the reaction mixture becomes dark red. The reaction mixture is acidified with 5% KHSO₄, diluted with brine (250 mL) and extracted with ethyl acetate (200 mL). The aqueous layer is extracted with another portion of ethyl acetate (50 mL) and the combined organic extracts are washed twice with brine (250 mL), dried over sodium sulfate and evaporated to yield crude product. The crude product is purified by flash chromatography on regular silica gel using ethyl acetate-hexane-acetic acid as eluent to afford the title intermediate.

Step H: Preparation of (Z)-7-((1R,2R,3R)-2-(3,3-difluoro-4-phenoxybutyl)-5-oxo-3-(tetrahydro-2H-pyran-2-yloxy)cyclopentyl)hept-5-enoic acid

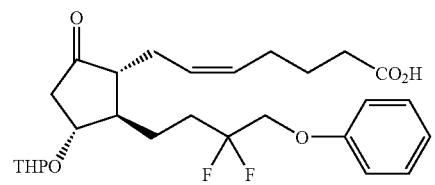

(Z)-7-((1R,2R,3R,5S)-2-(3,3-Difluoro-4-phenoxybutyl)-5-hydroxy-3-(tetrahydro-2H-pyran-2-yloxy)cyclopentyl)hept-5-enoic acid (limiting reagent, prepared in Step G) is dissolved in DCM (0.05 M) and cooled to 0° C. PCC (2 equivalents) is added and the reaction mixture is allowed to warm to room temperature with stirring. Upon completion by as indicated by TLC, the crude product is purified by flash chromatography on regular silica gel using ethyl acetate-hexane-acetic acid as eluent to afford the title intermediate.

Step I: Preparation of (Z)-7-((1R,2R,3R)-2-(3,3-difluoro-4-phenoxybutyl)-3-hydroxy-5-oxocyclopentyl)hept-5-enoic acid

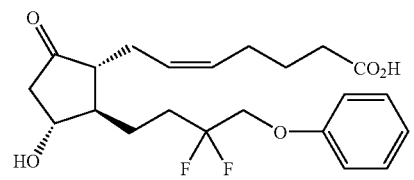

(Z)-7-((1R,2R,3R)-2-(3,3-Difluoro-4-phenoxybutyl)-5-oxo-3-(tetrahydro-2H-pyran-2-yloxy)cyclopentyl)hept-5-enoic acid, prepared in Step H, is dissolved in a (4:2:1) solution of acetic acid-water-THF (0.5 M). The solution is stirred for several days at room temperature until the reaction is complete, as judged by TLC. The crude product is purified by flash chromatography on regular silica gel using ethyl acetate-hexane-acetic acid as eluent to afford the title compound.

Scheme 1

Scheme 1 illustrates a synthetic route that may be utilized to prepare compounds of general structure 13-14, 21-22, and 25-26.

Scheme 1
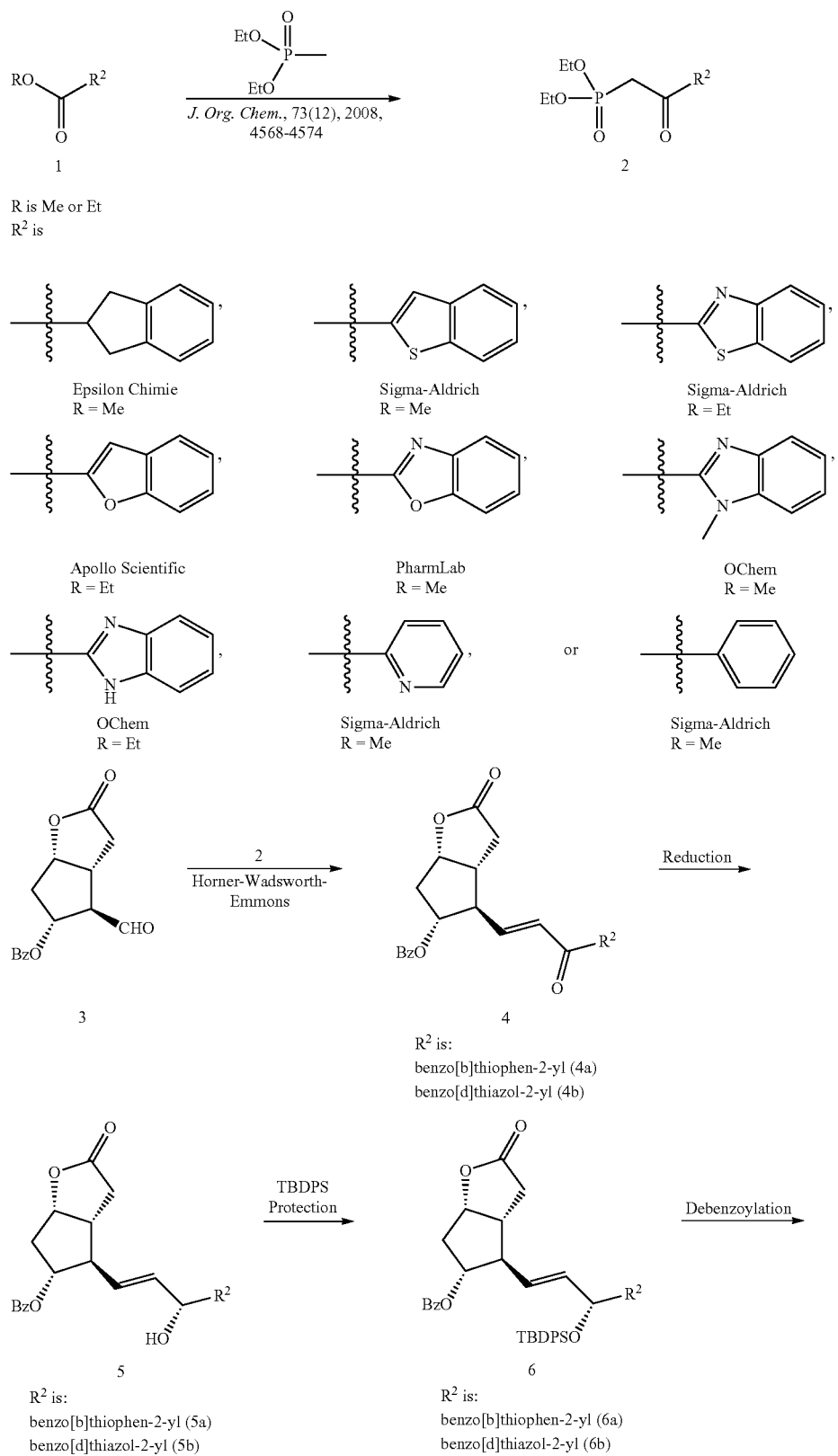

-continued

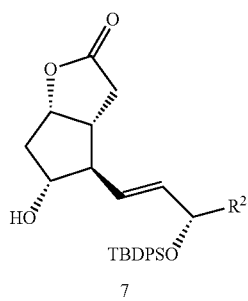

7

R² is:
benzo[b]thiophen-2-yl (6a)
benzo[d]thiazol-2-yl (6b)

→ Reduction →

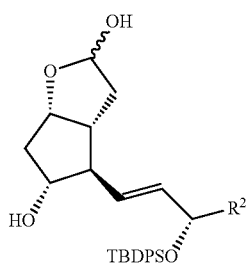

8

R² is:
benzo[b]thiophen-2-yl (8a)
benzo[d]thiazol-2-yl (8b)

→ Wittig →

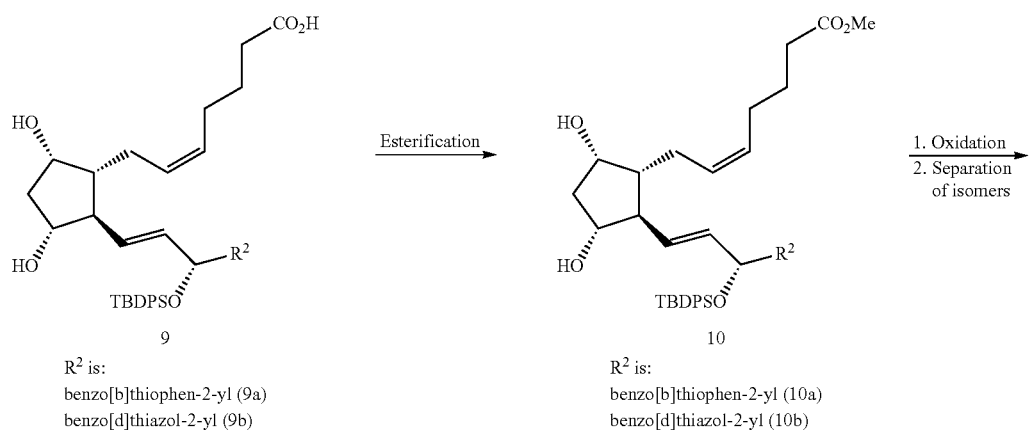

9

R² is:
benzo[b]thiophen-2-yl (9a)
benzo[d]thiazol-2-yl (9b)

→ Esterification →

10

R² is:
benzo[b]thiophen-2-yl (10a)
benzo[d]thiazol-2-yl (10b)

→ 1. Oxidation
2. Separation of isomers →

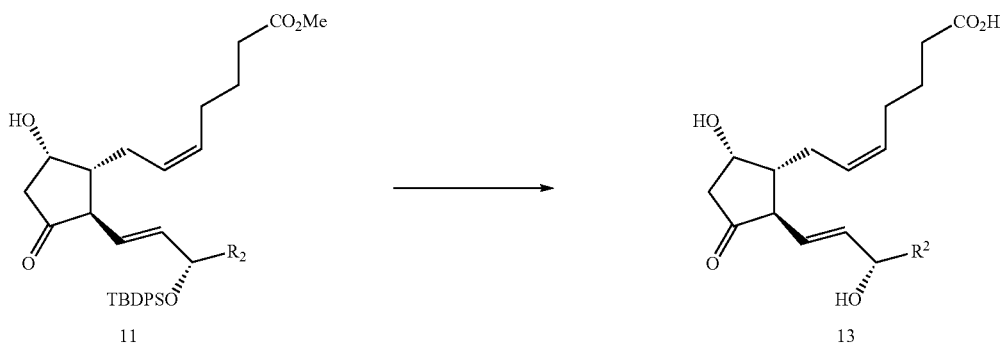

11

R² is:
benzo[b]thiophen-2-yl (11a)
benzo[d]thiazol-2-yl (11b)

+

1. Ester hydrolysis
2. Desilylation

→

13

R² is:
benzo[b]thiophen-2-yl (13a)
benzo[d]thiazol-2-yl (13b)

27 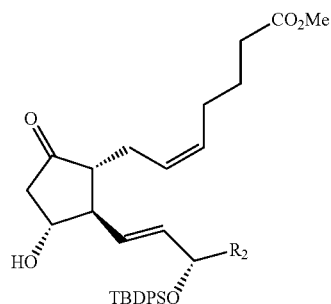
28 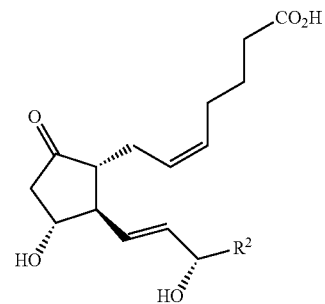
-continued
12
$R^2$ is:
benzo[b]thiophen-2-yl (12a)
benzo[d]thiazol-2-yl (12b)
14
$R^2$ is:
benzo[b]thiophen-2-yl (14a)
benzo[d]thiazol-2-yl (14b)
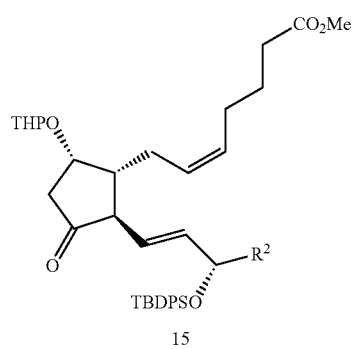
15
$R^2$ is:
benzo[b]thiophen-2-yl (15a)
benzo[d]thiazol-2-yl (15b)
11 or 12 →(THP Protection)→ or →(Methylene incorporation)→
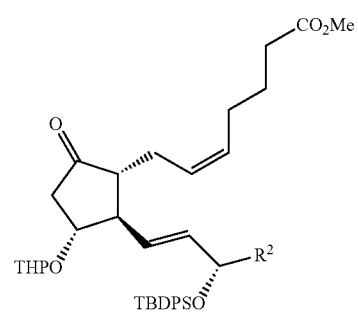
16
$R^2$ is:
benzo[b]thiophen-2-yl (16a)
benzo[d]thiazol-2-yl (16b)

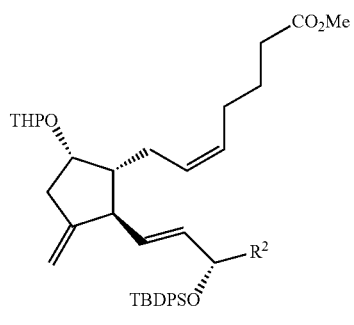
17
R² is:
benzo[b]thiophen-2-yl (17a)
benzo[d]thiazol-2-yl (17b)
or
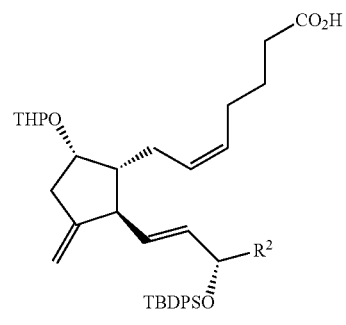
19
R² is:
benzo[b]thiophen-2-yl (19a)
benzo[d]thiazol-2-yl (19b)
Saponification ⟹
or
1. Desilylation
2. THP Deprotection ⟹
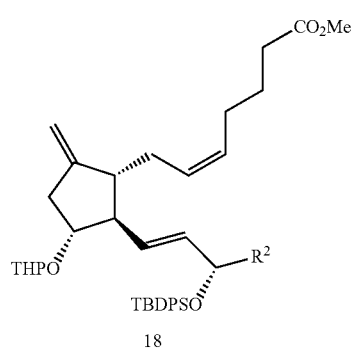
18
R² is:
benzo[b]thiophen-2-yl (18a)
benzo[d]thiazol-2-yl (18b)
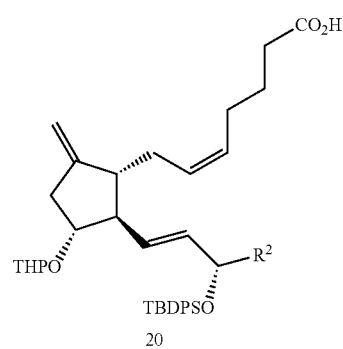
20
R² is:
benzo[b]thiophen-2-yl (20a)
benzo[d]thiazol-2-yl (20b)
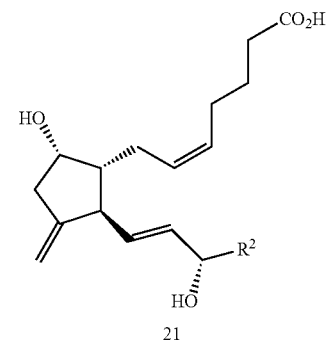
21
R² is:
benzo[b]thiophen-2-yl (21a)
benzo[d]thiazol-2-yl (21b)
or
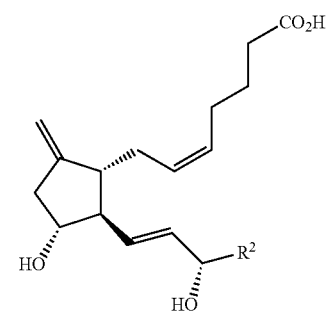
22
R² is:
benzo[b]thiophen-2-yl (22a)
benzo[d]thiazol-2-yl (22b)

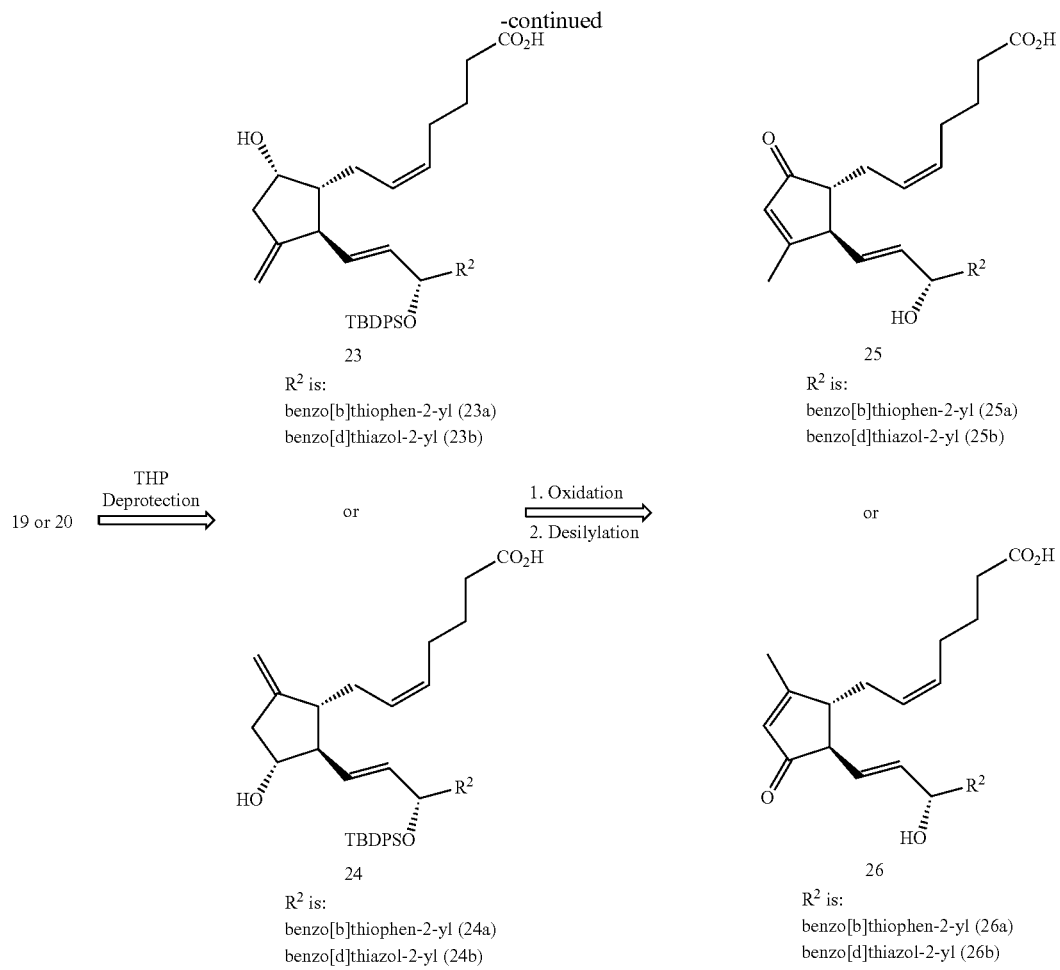

23
R² is:
benzo[b]thiophen-2-yl (23a)
benzo[d]thiazol-2-yl (23b)

25
R² is:
benzo[b]thiophen-2-yl (25a)
benzo[d]thiazol-2-yl (25b)

24
R² is:
benzo[b]thiophen-2-yl (24a)
benzo[d]thiazol-2-yl (24b)

26
R² is:
benzo[b]thiophen-2-yl (26a)
benzo[d]thiazol-2-yl (26b)

Examples 2, 3, 4, and 5 describe the preparation of exemplary embodiment compounds 21a, 25a, 22a, and 26a, respectively, as illustrated in Scheme 1. Examples 6 and 9 describe the preparation of exemplary embodiment compounds 13a and 13b, respectively, as illustrated in Scheme 1. Examples 7 and 8 describe the preparation of exemplary embodiment compounds 14a and 14 b, respectively, as illustrated in Scheme 1.

Example 2

Preparation of (Z)-7-((1R,2R,5S)-2-((R,E)-3-(benzo[b]thiophen-2-yl)-3-hydroxyprop-1-enyl)-5-hydroxy-3-methylenecyclopentyl)hept-5-enoic Acid (21a)

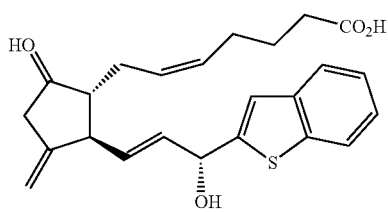

Step A: Preparation of (3aR,4R,5R,6aS)-4-((E)-3-(benzo[b]thiophen-2-yl)-3-oxoprop-1-enyl)-2-oxo-hexahydro-2H-cyclopenta[b]furan-5-yl benzoate (4a)

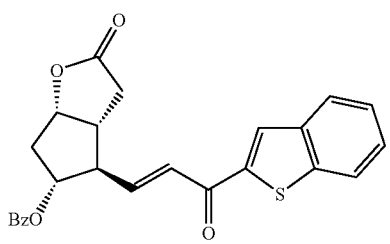

A reactor equipped with a mechanical stirrer, under nitrogen, is charged with (3aR,4R,5R,6aS)-4-formyl-2-oxo-hexahydro-2H-cyclopenta[b]furan-5-yl benzoate (99.2 g, 0.362 mol) in DCM and lithium chloride (1 molar equivalent) dissolved in THF. Diethyl 2-(benzo[b]thiophen-2-yl)-2-oxo-ethylphosphonate (1 molar equivalent) is added neat and rinsed with DCM. Some lithium chloride precipitates from solution when the THF and DCM solutions are mixed. The mixture is stirred under nitrogen and cooled to −20° C. After adding the phosphonate and subsequent stirring and cooling, the lithium chloride dissolved. After stirring for 2.5 hours, triethylamine (1 molar equivalent) is added neat via addition funnel and the temperature is held at −5° C. and stirred at this temperature for 19 hours. The temperature is adjusted to 0° C. and treated with 5% aqueous citric acid and the layers are separated. The organic layer is dried over magnesium sulfate and filtered. The crude product is purified on silica gel, eluted with ethyl acetate-hexanes (1:1) to afford the title intermediate 4a.

Step B: Preparation of (3aR,4R,5R,6aS)-4-((R,E)-3-(benzo[b]thiophen-2-yl)-3-hydroxyprop-1-enyl)-2-oxohexahydro-2H-cyclopenta[b]furan-5-yl benzoate (5a)

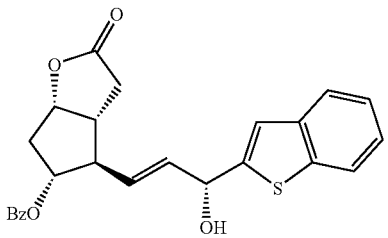

To a stirring solution consisting of (3aR,4R,5R,6aS)-4-((E)-3-(benzo[b]thiophen-2-yl)-3-oxoprop-1-enyl)-2-oxohexahydro-2H-cyclopenta[b]furan-5-yl benzoate (4a, limiting reagent) in 2:1 THF-methanol (0.1 M) cooled to −40° C. is added CeCl$_3$ heptahydrate. The reaction mixture is subsequently cooled to −78° C. and sodium borohydride (2 molar equivalents) is added and the solution is stirred for 1.5 hours. The reaction is quenched by the addition of acetone at −60° C. followed by the addition of a saturated aqueous ammonium chloride solution as the reaction mixture slowly warms to room temperature. The reaction mixture is diluted with brine and acidified with a small amount of 5% aqueous KHSO$_4$. The product is extracted with ethyl acetate twice and the combined organic layers are dried over sodium sulfate, filtered, and evaporated under reduced pressure. The crude product is purified by flash chromatography on regular silica gel eluted with hexanes-ethyl acetate to afford the title intermediate 5a.

Step C: Preparation of (3aR,4R,5R,6aS)-4-((R,E)-3-(benzo[b]thiophen-2-yl)-3-(tert-butyldiphenylsilyloxy)prop-1-enyl)-2-oxohexahydro-2H-cyclopenta[b]furan-5-yl benzoate (6a)

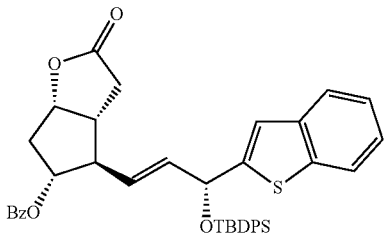

A stirring mixture consisting of (3aR,4R,5R,6aS)-4-((R,E)-3-(benzo[b]thiophen-2-yl)-3-hydroxyprop-1-enyl)-2-oxohexahydro-2H-cyclopenta[b]furan-5-yl benzoate (5a, limiting reagent) and imidazole (1.1 molar equivalents) in DMF (5 M in 5a) is cooled to 0° C. under a nitrogen atmosphere. A solution consisting of TBDPSCl (1.1 molar equivalents) in DMF is added slowly. Upon completion of the reaction, as judged by TLC, the reaction mixture is diluted with ethyl acetate and is washed with water and brine. The organic layer is dried over sodium sulfate, filtered, and evaporated under reduced pressure. The crude product is purified by flash chromatography on regular silica gel eluted with hexanes-ethyl acetate to afford the title intermediate 6a.

Step D: Preparation of (3aR,4R,5R,6aS)-4-((R,E)-3-(benzo[b]thiophen-2-yl)-3-(tert-butyldiphenylsilyloxy)prop-1-enyl)-5-hydroxyhexahydro-2H-cyclopenta[b]furan-2-one (7a)

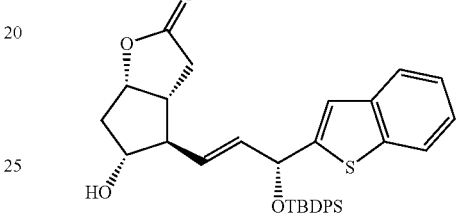

A mixture consisting of (3aR,4R,5R,6aS)-4-((R,E)-3-(benzo[b]thiophen-2-yl)-3-(tert-butyldiphenylsilyloxy)prop-1-enyl)-2-oxohexahydro-2H-cyclopenta[b]furan-5-yl benzoate (6a, limiting reagent) in methanol (0.2 M) and potassium carbonate (0.6 molar equivalent) is stirred at room temperature and the reaction progress is monitored by TLC every 30 minutes. After complete consumption of starting material, the reaction mixture is acidified with 5% aqueous KHSO$_4$ and diluted with brine. The product is extracted with ethyl acetate twice. The combined organic layers are dried over sodium sulfate, filtered, and evaporated under reduced pressure. The crude product is purified by flash chromatography on regular silica gel eluted with hexanes-ethyl acetate (1:1) to afford the title intermediate 7a.

Step E: Preparation of (3aR,4R,5R,6aS)-4-((R,E)-3-(benzo[b]thiophen-2-yl)-3-(tert-butyldiphenylsilyloxy)prop-1-enyl)hexahydro-2H-cyclopenta[b]furan-2,5-diol (8a)

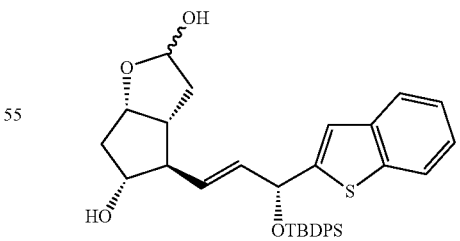

(3aR,4R,5R,6aS)-4-((R,E)-3-(Benzo[b]thiophen-2-yl)-3-(tert-butyldiphenylsilyloxy)prop-1-enyl)-5-hydroxyhexahydro-2H-cyclopenta[b]furan-2-one (7a, limiting reagent) is dissolved in anhydrous THF (0.5 M) under a nitrogen atmosphere and cooled to −78° C. A solution consisting of DIBAL-H (1 M in toluene, 2 molar equivalents) is added to the reaction mixture dropwise and stirred for 3 hours. Ethyl acetate (20 mL) is added and the mixture is stirred for an additional 5 minutes. The mixture is then treated with 30% aqueous K, Na tartrate and stirred vigorously overnight. The layers are separated and the organic phase is filtered and concentrated under reduced pressure. The crude product is purified by flash chromatography on regular silica gel eluted with hexanes-ethyl acetate to afford the title intermediate 8a.

Step F: Preparation of (Z)-7-((1R,2R,3R,5S)-2-((R, E)-3-(benzo[b]thiophen-2-yl)-3-(tert-butyldiphenyl-silyloxy)prop-1-enyl)-3,5-dihydroxycyclopentyl) hept-5-enoic Acid (9a)

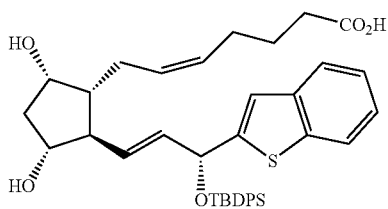

4-Carboxybutyltriphenylphosphonium bromide (3.5 molar equivalents) is suspended in anhydrous THF under a nitrogen atmosphere. Potassium tert-butoxide (1 M in THF, 7 molar equivalents) is added dropwise to the white suspension. The reaction mixture becomes bright red over the course of the addition and is subsequently stirred for 30 minutes at room temperature, then cooled to −15° C. in an ice/NaCl bath. The lactol (3aR,4R,5R,6aS)-4-((R,E)-3-(benzo[b]thiophen-2-yl)-3-(tert-butyldiphenylsilyloxy)prop-1-enyl)hexahydro-2H-cyclopenta[b]furan-2,5-diol (8a, limiting reagent) is dissolved in THF and added dropwise to the ylide. The reaction mixture becomes lighter orange in color and is additionally stirred for 2 hours at −15° C. and is then allowed to warm to room temperature and stir overnight. The reaction mixture becomes dark red. The reaction mixture is acidified with 5% aqueous KHSO$_4$, diluted with brine (250 mL) and extracted with ethyl acetate (200 mL). The aqueous layer is extracted with another portion of ethyl acetate (50 mL) and the combined organic extracts are washed twice with brine (250 mL), dried over sodium sulfate, and evaporated to yield crude product. The crude product is purified by flash chromatography on regular silica gel using hexanes-ethyl acetate with 0.4% acetic acid as eluent to afford the title intermediate 9a.

Step G: Preparation of (Z)-methyl 7-((1R,2R,3R,5S)-2-((R,E)-3-(benzo[b]thiophen-2-yl)-3-(tert-butyl-diphenylsilyloxy)prop-1-enyl)-3,5-dihydroxycyclo-pentyl)hept-5-enoate (10a)

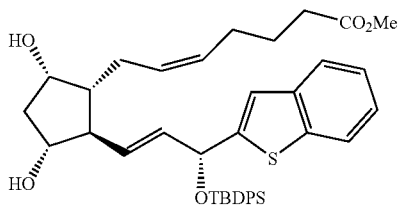

(Z)-7-((1R,2R,3R,5S)-2-((R,E)-3-(Benzo[b]thiophen-2-yl)-3-(tert-butyldiphenylsilyloxy)prop-1-enyl)-3,5-dihydroxycyclopentyl)hept-5-enoic acid, 9a, is dissolved in diethyl ether (0.1 M) and cooled to 0° C. under a nitrogen atmosphere. Diazomethane (freshly prepared solution in diethyl ether) is added to the solution with stirring under a light yellow color persisting. The completion of the reaction is confirmed by the absence of starting material as judged by TLC. Upon completion, the solvents are evaporated and the product is purified by flash chromatography using hexanes-ethyl acetate as eluent to afford the title intermediate 10a.

Step H: Preparation, separation, and isolation of (Z)-methyl 7-((1R,2R,5S)-2-((R,E)-3-(benzo[b]thiophen-2-yl)-3-(tert-butyldiphenylsilyloxy)prop-1-enyl)-5-hydroxy-3-oxocyclopentyl)hept-5-enoate (11a) and (Z)-methyl 7-((1R,2R,3R)-2-((R,E)-3-(benzo[b]thiophen-2-yl)-3-(tert-butyldiphenylsilyloxy)prop-1-enyl)-3-hydroxy-5-oxocyclopentyl)hept-5-enoate (12a)

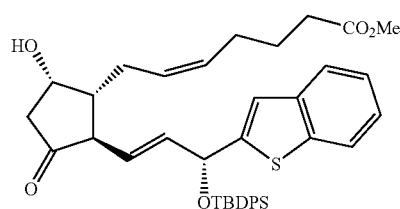

11a

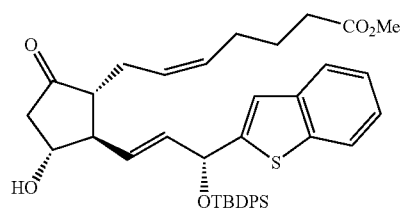

12a (Z)-Methyl 7-((1R,2R,3R,5S)-2-((R,E)-3-(benzo[b]thiophen-2-yl)-3-(tert-butyldiphenylsilyloxy)prop-1-enyl)-3,5-dihydroxycyclopentyl)hept-5-enoate, 10a, is dissolved in acetone (0.1 M) and cooled to −25° C. Jones reagent (1 molar equivalent) is added dropwise with stirring. Upon completion, as judged by TLC, the reaction is quenched with isopropyl alcohol and the crude reaction mixture is diluted with ethyl acetate, washed three times with brine, and dried over magnesium sulfate. After filtration and solvent evaporation, the product is purified by flash chromatography using hexanes-ethyl acetate as eluent to afford both (Z)-methyl 7-((1R, 2R,5S)-2-((R,E)-3-(benzo[b]thiophen-2-yl)-3-(tert-butyldiphenylsilyloxy)prop-1-enyl)-5-hydroxy-3-oxocyclopentyl) hept-5-enoate (11a, first to elute) and (Z)-methyl 7-((1R,2R, 3R)-2-((R,E)-3-(benzo[b]thiophen-2-yl)-3-(tert-butyldiphenylsilyloxy)prop-1-enyl)-3-hydroxy-5-oxocyclopentyl) hept-5-enoate (12a).

Step I: Preparation of (Z)-methyl 7-((1R,2R,5S)-2-((R,E)-3-(benzo[b]thiophen-2-yl)-3-(tert-butyldiphenylsilyloxy)prop-1-enyl)-3-oxo-5-(tetrahydro-2H-pyran-2-yloxy)cyclopentyl)hept-5-enoate (15a)

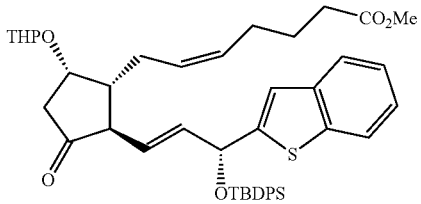

(Z)-Methyl 7-((1R,2R,5S)-2-((R,E)-3-(benzo[b]thiophen-2-yl)-3-(tert-butyldiphenylsilyloxy)prop-1-enyl)-5-hydroxy-3-oxocyclopentyl)hept-5-enoate (11a, limiting reagent) is dissolved in DCM (0.1 M) under a nitrogen atmosphere. Dihydropyran (1.1 molar equivalent) is added, followed by a catalytic amount of p-toluenesulfonic acid. The reaction is stirred at room temperature under a nitrogen atmosphere and the reaction progress is monitored by TLC. Upon completion, brine is added to the reaction mixture and the layers are separated. The organic phase is dried over sodium sulfate, filtered, and the solvent is evaporated. The crude product is purified by flash chromatography on regular silica gel eluted with hexanes-ethyl acetate to afford the title intermediate 15a.

Step J: Preparation of (Z)-methyl 7-((1R,2R,5S)-2-((R,E)-3-(benzo[b]thiophen-2-yl)-3-(tert-butyldiphenylsilyloxy)prop-1-enyl)-3-methylene-5-(tetrahydro-2H-pyran-2-yloxy)cyclopentyl)hept-5-enoate (17a)

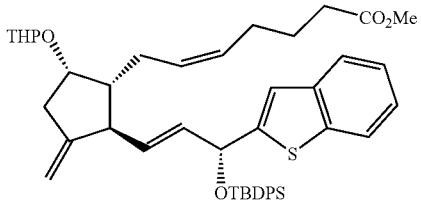

(Z)-Methyl 7-((1R,2R,5S)-2-((R,E)-3-(benzo[b]thiophen-2-yl)-3-(tert-butyldiphenylsilyloxy)prop-1-enyl)-3-oxo-5-(tetrahydro-2H-pyran-2-yloxy)cyclopentyl)hept-5-enoate (15a, limiting reagent) is dissolved in DCM (0.05 M) under a nitrogen atmosphere and cooled to 0° C. A solution consisting of zinc methylene dibromide titanium tetrachloride is prepared by combining zinc dust (2.3 g) in THF (40 mL) with methylene dibromide (0.81 mL) at −40° C. under a nitrogen atmosphere. To the suspension is slowly added TiCl$_4$ (0.92 mL). Portions (2 mL) of the zinc methylene dibromide titanium tetrachloride solution are added until the reaction is complete as judged by TLC. Upon completion, the reaction mixture is diluted with ethyl acetate and filtered twice through a bed of Celite. The filtrate is washed with a saturated aqueous solution of sodium bicarbonate, then with a 50% aqueous solution of brine. The organic phase is dried over sodium sulfate, filtered, and the solvent is evaporated. The crude product is purified by flash chromatography on regular silica gel eluted with hexanes-ethyl acetate to afford the title intermediate 17a.

Step K: Preparation of (Z)-7-((1R,2R,5S)-2-((R,E)-3-(benzo[b]thiophen-2-yl)-3-(tert-butyldiphenylsilyloxy)prop-1-enyl)-3-methylene-5-(tetrahydro-2H-pyran-2-yloxy)cyclopentyl)hept-5-enoic Acid (19a)

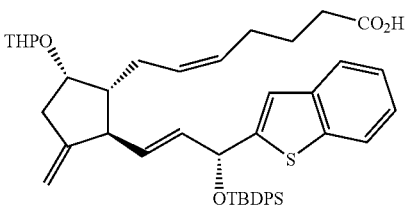

(Z)-Methyl 7-((1R,2R,5S)-2-((R,E)-3-(benzo[b]thiophen-2-yl)-3-(tert-butyldiphenylsilyloxy)prop-1-enyl)-3-methylene-5-(tetrahydro-2H-pyran-2-yloxy)cyclopentyl)hept-5-enoate (17a, limiting reagent) is dissolved in a 3:1 methanol and 1 N LiOH solution (0.01 M) and stirred at 4° C. Upon completion of the reaction, as judged by TLC, the reaction mixture is diluted with ethyl acetate, washed with 5% aqueous KHSO$_4$ and brine. The organic phase is dried over sodium sulfate, filtered, and the solvent is evaporated. The crude product is purified by flash chromatography on regular silica gel eluted with hexanes-ethyl acetate to afford the title intermediate 19a.

Step L: Preparation of (Z)-7-((1R,2R,5S)-2-((R,E)-3-(benzo[b]thiophen-2-yl)-3-hydroxyprop-1-enyl)-3-methylene-5-(tetrahydro-2H-pyran-2-yloxy)cyclopentyl)hept-5-enoic acid

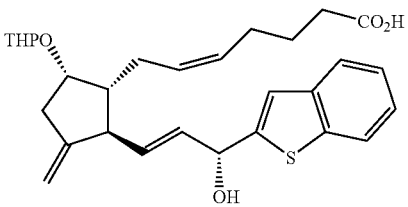

(Z)-7-((1R,2R,5S)-2-((R,E)-3-(Benzo[b]thiophen-2-yl)-3-(tert-butyldiphenylsilyloxy)prop-1-enyl)-3-methylene-5-(tetrahydro-2H-pyran-2-yloxy)cyclopentyl)hept-5-enoic acid (19a, limiting reagent) is dissolved in THF (0.3 M) under a nitrogen atmosphere. A solution consisting of TBAF in THF (1.2 molar equivalents, 1 M) is added and the reaction mixture is stirred at room temperature. Upon completion, as judged by TLC, water is added and most of the THF is removed under reduced pressure. The remaining aqueous solution is extracted with ethyl acetate and is washed with water and brine. The organic phase is dried over sodium sulfate, filtered, and the solvent is evaporated. The crude product is purified by flash chromatography on regular silica gel eluted with hexanes-ethyl acetate (+0.4% acetic acid) to afford the title intermediate.

Step M: Preparation of (Z)-7-((1R,2R,5S)-2-((R,E)-3-(benzo[b]thiophen-2-yl)-3-hydroxyprop-1-enyl)-5-hydroxy-3-methylenecyclopentyl)hept-5-enoic Acid (21a)

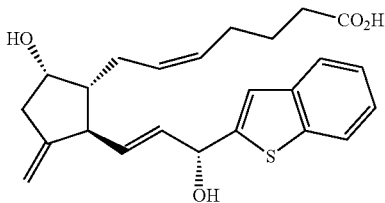

(Z)-7-((1R,2R,5S)-2-((R,E)-3-(Benzo[b]thiophen-2-yl)-3-hydroxyprop-1-enyl)-3-methylene-5-(tetrahydro-2H-pyran-2-yloxy)cyclopentyl)hept-5-enoic acid, prepared in Step L, is dissolved in a (4:2:1) solution of acetic acid-water-THF (0.5 M). The solution is stirred for several days at room temperature until the reaction is complete, as judged by TLC. The crude product is purified by flash chromatography on regular silica gel using ethyl acetate-hexane-acetic acid as eluent to afford the title compound 21a.

Example 3

Preparation of (Z)-7-((1R,2R)-2-((R,E)-3-(benzo[b]thiophen-2-yl)-3-hydroxyprop-1-enyl)-3-methyl-5-oxocyclopent-3-enyl)hept-5-enoic Acid (25a)

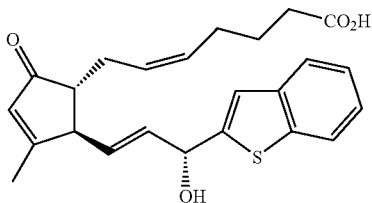

Step A: Preparation of (Z)-7-((1R,2R,5S)-2-((R,E)-3-(benzo[b]thiophen-2-yl)-3-(tert-butyldiphenylsilyloxy)prop-1-enyl)-5-hydroxy-3-methylenecyclopentyl)hept-5-enoic acid (23a)

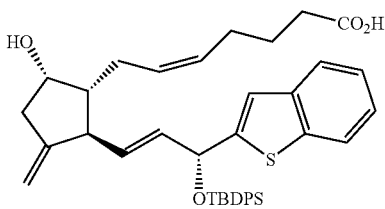

The title intermediate 23a is prepared from (Z)-7-((1R,2R,5S)-2-((R,E)-3-(benzo[b]thiophen-2-yl)-3-(tert-butyldiphenylsilyloxy)prop-1-enyl)-3-methylene-5-(tetrahydro-2H-pyran-2-yloxy)cyclopentyl)hept-5-enoic acid (prepared in Example 2, Step K) in a THP-deprotection procedure similar to that which is described in Example 2, Step M.

Step B: Preparation of (Z)-7-((1R,2R)-2-((R,E)-3-(benzo[b]thiophen-2-yl)-3-(tert-butyldiphenylsilyloxy)prop-1-enyl)-3-methyl-5-oxocyclopent-3-enyl)hept-5-enoic acid

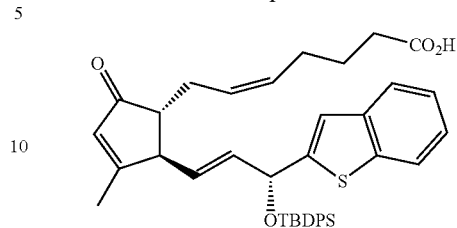

(Z)-7-((1R,2R,5S)-2-((R,E)-3-(Benzo[b]thiophen-2-yl)-3-(tert-butyldiphenylsilyloxy)prop-1-enyl)-5-hydroxy-3-methylenecyclopentyl)hept-5-enoic acid (23a) is dissolved in acetone (0.1 M) and cooled to −25° C. Jones reagent (1 molar equivalent) is added dropwise with stirring. Upon completion, as judged by TLC, the reaction is quenched with isopropyl alcohol and the crude reaction mixture is diluted with ethyl acetate, washed three times with brine, and dried over magnesium sulfate. After filtration and solvent evaporation, the product is purified by flash chromatography using hexanes-ethyl acetate as eluent to afford the title intermediate.

Step C: Preparation of (Z)-7-((1R,2R)-2-((R,E)-3-(benzo[b]thiophen-2-yl)-3-hydroxyprop-1-enyl)-3-methyl-5-oxocyclopent-3-enyl)hept-5-enoic Acid (25a)

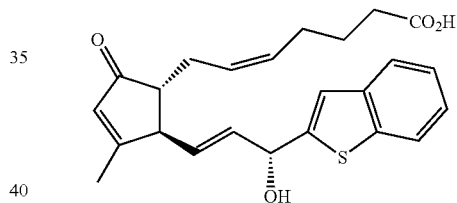

The title compound 25a is prepared from (Z)-7-((1R,2R)-2-((R,E)-3-(benzo[b]thiophen-2-yl)-3-(tert-butyldiphenylsilyloxy)prop-1-enyl)-3-methyl-5-oxocyclopent-3-enyl)hept-5-enoic acid (prepared in Step B) with a procedure similar to that which is described in Example 2, Step L.

Example 4

Preparation of (Z)-7-((1R,2R,3R)-2-((R,E)-3-(Benzo[b]thiophen-2-yl)-3-hydroxyprop-1-enyl)-3-hydroxy-5-methylenecyclopentyl)hept-5-enoic Acid (22a)

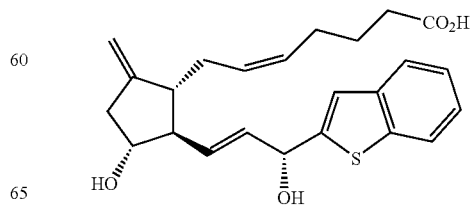

Step A: Preparation of (Z)-methyl 7-((1R,2R,3R)-2-((R,E)-3-(benzo[b]thiophen-2-yl)-3-(tert-butyldiphenylsilyloxy)prop-1-enyl)-5-oxo-3-(tetrahydro-2H-pyran-2-yloxy)cyclopentyl)hept-5-enoate (16a)

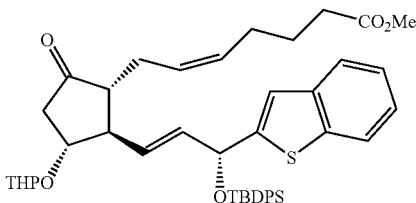

The title intermediate 16a is prepared from (Z)-methyl 7-((1R,2R,3R)-2-((R,E)-3-(benzo[b]thiophen-2-yl)-3-(tert-butyldiphenylsilyloxy)prop-1-enyl)-3-hydroxy-5-oxocyclopentyl)hept-5-enoate (intermediate 12a prepared in Example 2, Step H) with a procedure similar to that which is described in Example 2, Step I.

Step B: Preparation of (Z)-methyl 7-((1R,2R,3R)-2-((R,E)-3-(benzo[b]thiophen-2-yl)-3-(tert-butyldiphenylsilyloxy)prop-1-enyl)-5-methylene-3-(tetrahydro-2H-pyran-2-yloxy)cyclopentyl)hept-5-enoate (18a)

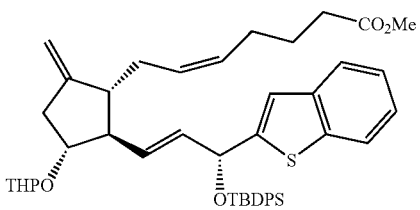

The title intermediate 18a is prepared from (Z)-methyl 7-((1R,2R,3R)-2-((R,E)-3-(benzo[b]thiophen-2-yl)-3-(tert-butyldiphenylsilyloxy)prop-1-enyl)-5-oxo-3-(tetrahydro-2H-pyran-2-yloxy)cyclopentyl)hept-5-enoate (16a) with a procedure similar to that which is described in Example 2, Step J.

Step C: Preparation of (Z)-7-((1R,2R,3R)-2-((R,E)-3-(benzo[b]thiophen-2-yl)-3-(tert-butyldiphenylsilyloxy)prop-1-enyl)-5-methylene-3-(tetrahydro-2H-pyran-2-yloxy)cyclopentyl)hept-5-enoic Acid (20a)

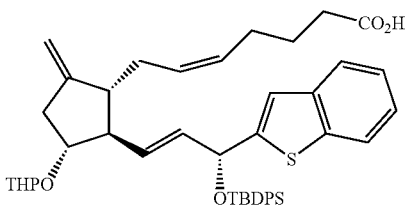

The title intermediate 20a is prepared from (Z)-methyl 7-((1R,2R,3R)-2-((R,E)-3-(benzo[b]thiophen-2-yl)-3-(tert-butyldiphenylsilyloxy)prop-1-enyl)-5-methylene-3-(tetrahydro-2H-pyran-2-yloxy)cyclopentyl)hept-5-enoate (18a) with a procedure similar to that which is described in Example 2, Step K.

Step D: Preparation of (Z)-7-((1R,2R,3R)-2-((R,E)-3-(benzo[b]thiophen-2-yl)-3-hydroxyprop-1-enyl)-5-methylene-3-(tetrahydro-2H-pyran-2-yloxy)cyclopentyl)hept-5-enoic acid

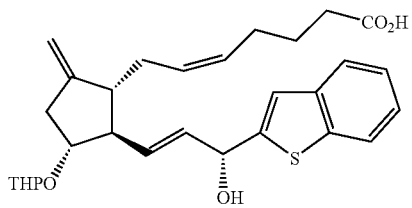

The title intermediate is prepared from (Z)-7-((1R,2R,3R)-2-((R,E)-3-(benzo[b]thiophen-2-yl)-3-(tert-butyldiphenylsilyloxy)prop-1-enyl)-5-methylene-3-(tetrahydro-2H-pyran-2-yloxy)cyclopentyl)hept-5-enoic acid (20a) with a procedure similar to that which is described in Example 2, Step L.

Step E: Preparation of (Z)-7-((1R,2R,3R)-2-((R,E)-3-(benzo[b]thiophen-2-yl)-3-hydroxyprop-1-enyl)-3-hydroxy-5-methylenecyclopentyl)hept-5-enoic Acid (22a)

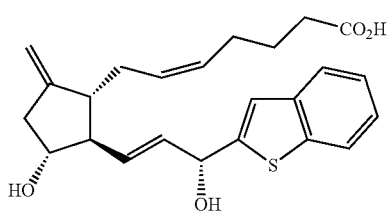

The title compound 22a is prepared from (Z)-7-((1R,2R,3R)-2-((R,E)-3-(benzo[b]thiophen-2-yl)-3-hydroxyprop-1-enyl)-5-methylene-3-(tetrahydro-2H-pyran-2-yloxy)cyclopentyl)hept-5-enoic acid, prepared in Step D, with a procedure to that which is described in Example 2, Step M.

Example 5

Preparation of (Z)-7-((1R,5R)-5-((R,E)-3-(Benzo[b]thiophen-2-yl)-3-hydroxyprop-1-enyl)-2-methyl-4-oxocyclopent-2-enyl)hept-5-enoic Acid (26a)

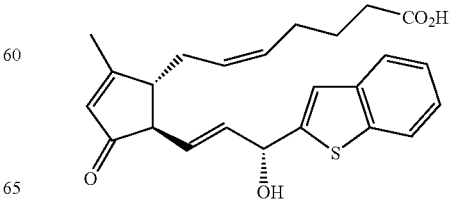

Step A: Preparation of (Z)-7-((1R,2R,3R)-2-((R,E)-3-(benzo[b]thiophen-2-yl)-3-(tert-butyldiphenylsilyloxy)prop-1-enyl)-3-hydroxy-5-methylenecyclopentyl)hept-5-enoic Acid (24a)

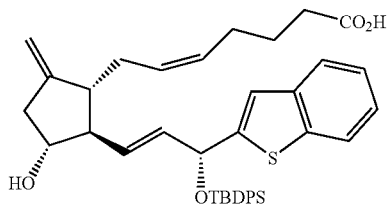

The title intermediate 24a is prepared from (Z)-7-((1R,2R,3R)-2-((R,E)-3-(benzo[b]thiophen-2-yl)-3-hydroxyprop-1-enyl)-3-hydroxy-5-methylenecyclopentyl)hept-5-enoic acid (22a) with a procedure similar to that which is described in Example 2, Step M.

Step B: Preparation of (Z)-7-((1R,5R)-5-((R,E)-3-(benzo[b]thiophen-2-yl)-3-(tert-butyldiphenylsilyloxy)prop-1-enyl)-2-methyl-4-oxocyclopent-2-enyl)hept-5-enoic Acid

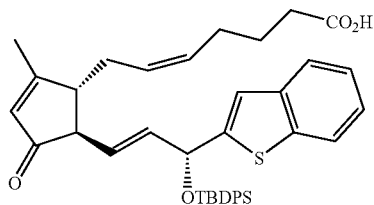

The title intermediate is prepared from (Z)-7-((1R,2R,3R)-2-((R,E)-3-(benzo[b]thiophen-2-yl)-3-(tert-butyldiphenylsilyloxy)prop-1-enyl)-3-hydroxy-5-methylenecyclopentyl)hept-5-enoic acid (24a) with a procedure similar to that which is described in Example 3, Step B.

Step C: Preparation of (Z)-7-((1R,5R)-5-((R,E)-3-(benzo[b]thiophen-2-yl)-3-hydroxyprop-1-enyl)-2-methyl-4-oxocyclopent-2-enyl)hept-5-enoic Acid (26a)

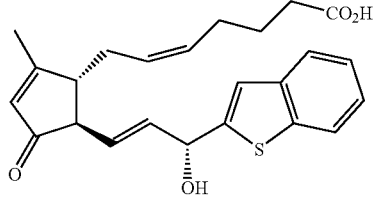

The title compound 26a is prepared from (Z)-7-((1R,5R)-5-((R,E)-3-(benzo[b]thiophen-2-yl)-3-(tert-butyldiphenylsilyloxy)prop-1-enyl)-2-methyl-4-oxocyclopent-2-enyl)hept-5-enoic acid, prepared in Step B, with a procedure similar to that which is described in Example 2, Step L.

Example 6

Preparation of (Z)-7-((1R,2R,5S)-2-((R,E)-3-(benzo[b]thiophen-2-yl)-3-hydroxyprop-1-enyl)-5-hydroxy-3-oxocyclopentyl)hept-5-enoic Acid (13a)

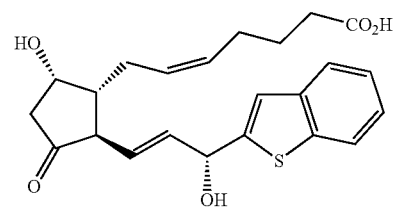

Step A: Preparation of (Z)-7-((1R,2R,5S)-2-((R,E)-3-(benzo[b]thiophen-2-yl)-3-(tert-butyldiphenylsilyloxy)prop-1-enyl)-5-hydroxy-3-oxocyclopentyl)hept-5-enoic Acid

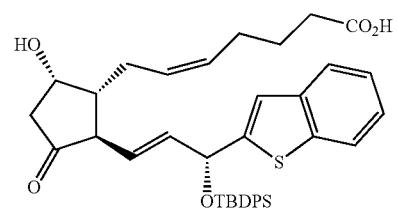

The title intermediate is prepared from (Z)-methyl 7-((1R,2R,5S)-2-((R,E)-3-(benzo[b]thiophen-2-yl)-3-(tert-butyldiphenylsilyloxy)prop-1-enyl)-5-hydroxy-3-oxocyclopentyl)hept-5-enoate (11a, prepared in Example 2, Step H) using a hydrolysis procedure described in Example 2, Step K.

Step B: Preparation of (Z)-7-((1R,2R,5S)-2-((R,E)-3-(benzo[b]thiophen-2-yl)-3-hydroxyprop-1-enyl)-5-hydroxy-3-oxocyclopentyl)hept-5-enoic Acid (13a)

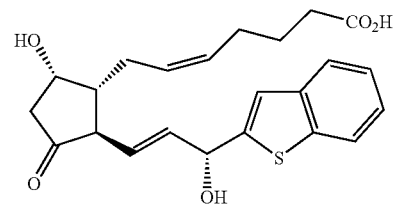

The title compound 13a is prepared from (Z)-7-((1R,2R,5S)-2-((R,E)-3-(benzo[b]thiophen-2-yl)-3-(tert-butyldiphenylsilyloxy)prop-1-enyl)-5-hydroxy-3-oxocyclopentyl)hept-5-enoic acid, prepared in Step A, with a procedure similar to that which is described in Example 2, Step L.

Example 7

Preparation of (Z)-7-((1R,2R,3R)-2-((R,E)-3-(benzo[b]thiophen-2-yl)-3-hydroxyprop-1-enyl)-3-hydroxy-5-oxocyclopentyl)hept-5-enoic Acid (14a)

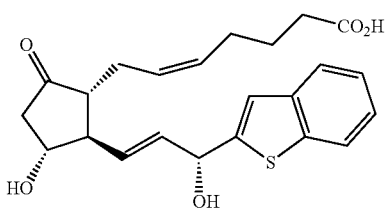

Step A: Preparation of (Z)-7-((1R,2R,3R)-2-((R,E)-3-(benzo[b]thiophen-2-yl)-3-(tert-butyldiphenylsilyloxy)prop-1-enyl)-3-hydroxy-5-oxocyclopentyl)hept-5-enoic Acid

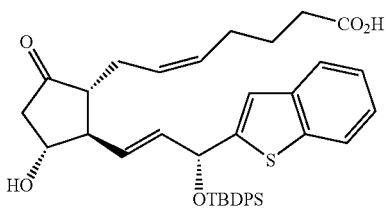

The title intermediate is prepared from (Z)-methyl 7-((1R,2R,3R)-2-((R,E)-3-(benzo[b]thiophen-2-yl)-3-(tert-butyldiphenylsilyloxy)prop-1-enyl)-3-hydroxy-5-oxocyclopentyl)hept-5-enoate (12a, prepared in Example 2, Step H) using a hydrolysis procedure described in Example 2, Step K.

Step B: Preparation of (Z)-7-((1R,2R,3R)-2-((R,E)-3-(benzo[b]thiophen-2-yl)-3-hydroxyprop-1-enyl)-3-hydroxy-5-oxocyclopentyl)hept-5-enoic Acid (14a)

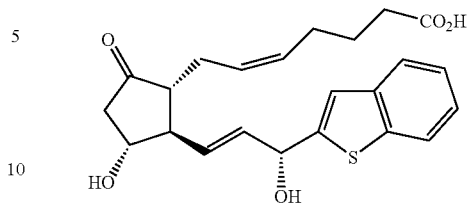

The title compound 14a is prepared from (Z)-7-((1R,2R,3R)-2-((R,E)-3-(benzo[b]thiophen-2-yl)-3-(tert-butyldiphenylsilyloxy)prop-1-enyl)-3-hydroxy-5-oxocyclopentyl)hept-5-enoic acid, prepared in Step A, with a procedure similar to that which is described in Example 2, Step L.

Functional Assay #1AGii (Cerep $EP_1$ Agonist Assay)
% Control Agonist response @ compound concentration (Mean of N=2)
144% @ 10 μM
88% @ 1 μM
80% @ 0.1 μM Functional Assay #2AGii (Cerep $EP_2$ Agonist Assay)
% Control Agonist response @ compound concentration (Mean of N=2)
5% @ 10 μM
−1% @ 1 μM
0% @ 0.1 μM Functional Assay #4AGii (Cerep $EP_4$ Agonist Assay)
% Control Agonist response @ compound concentration (Mean of N=2)
29% @ 10 μM
4% @ 1 μM
−1% @ 0.1 μM Scheme 2

An alternate route for the preparation of compound 14a is illustrated in Scheme 2 and described in the following example.

Scheme 2

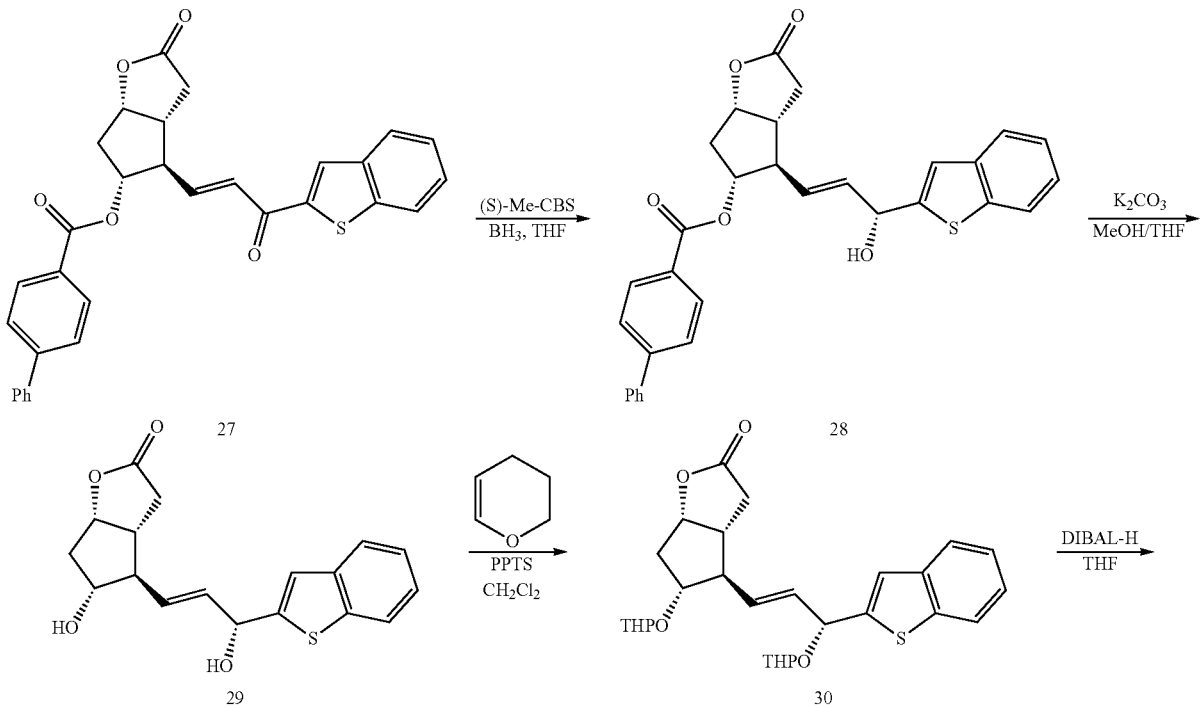

-continued

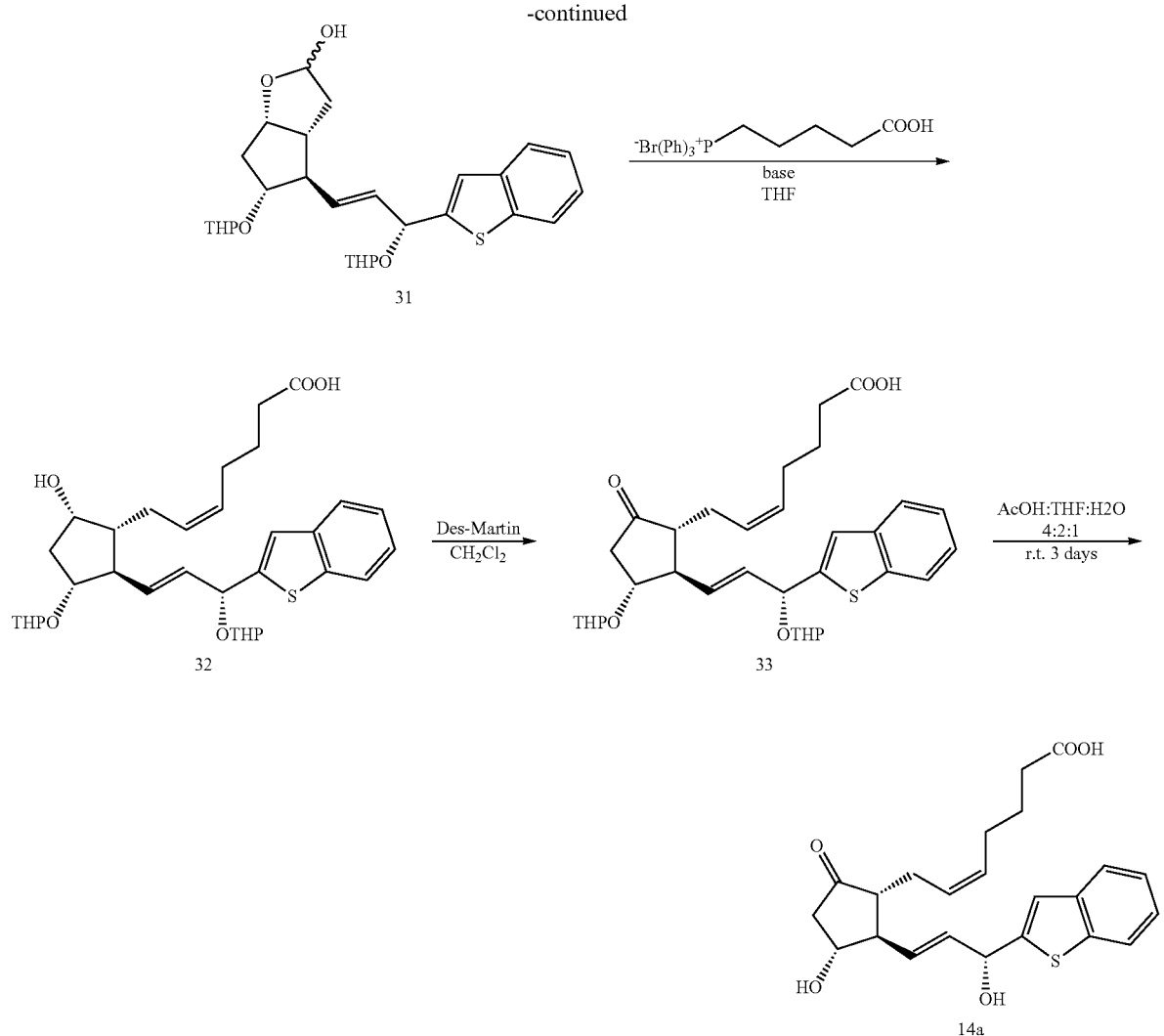

Alternate preparation of (Z)-7-((1R,2R,3R)-2-((R,E)-3-(benzo[b]thiophen-2-yl)-3-hydroxyprop-1-enyl)-3-hydroxy-5-oxocyclopentyl)hept-5-enoic Acid (14a)

Step A: Preparation of (3aR,4R,5R,6aS)-4-((E)-3-(benzo[b]thiophen-2-yl)-3-oxoprop-1-enyl)-2-oxo-hexahydro-2H-cyclopenta[b]furan-5-yl biphenyl-4-carboxylate (27)

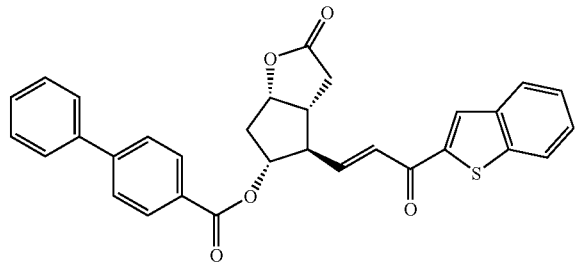

A reactor equipped with a mechanical stirrer, under nitrogen, was charged with a mixture consisting of (3aR,4R,5R,6aS)-4-formyl-2-oxohexahydro-2H-cyclopenta[b]furan-5-yl biphenyl-4-carboxylate in DCM and a mixture consisting of lithium chloride (1 molar equivalent) in THF. Diethyl 2-(2,7a-dihydrobenzo[b]thiophen-2-yl)-2-oxoethylphosphonate (1 molar equivalent) was added neat and rinsed with DCM. Some lithium chloride precipitated from solution when the THF and DCM mixtures were combined. The mixture was stirred under nitrogen and cooled to −20° C. After adding the phosphonate and further stirring and cooling, the lithium chloride dissolved. After stirring for 2.5 hours, triethylamine (1 molar equivalent) was added neat via addition funnel and the temperature was maintained at −5° C. for 19 hours. The temperature was adjusted to 0° C. and the reaction mixture was treated with 5% aqueous citric acid. The layers were separated and the organic layer was dried over magnesium sulfate and filtered. The crude product was purified on silica gel, eluted with ethyl acetate-hexanes (1:1) to afford the title intermediate 27; $^1$H NMR (CDCl$_3$) δ 8.10-8.15 (m, 2H), 8.05 (s, 1H), 7.89-7.95 (m, 2H), 7.60-7.75 (m, 4H), 7.38-7.60 (m, 5H), 6.98-7.17 (m, 2H), 5.45-5.55 (m, 1H), 5.18-5.25 (m, 1H), 2.93-3.15 (m, 3H), 2.55-2.77 (m, 2H), 2.38-2.47 (m, 1H).

Step B: Preparation of (3aR,4R,5R,6aS)-4-((R,E)-3-(benzo[b]thiophen-2-yl)-3-hydroxyprop-1-enyl)-2-oxohexahydro-2H-cyclopenta[b]furan-5-yl biphenyl-4-carboxylate (28)

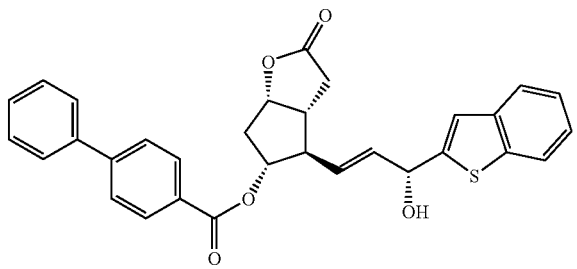

Procedure i:

A solution consisting of 1 M BH₃.THF in THF (0.46 g) was diluted with additional anhydrous THF (2 mL). The solution was cooled to −20° C. using an ethylene glycol/dry ice bath and a mixture consisting of (S)-2-methyl-CBS-oxazaborolidine in toluene (1 M, 1.07 mL, 0.20 eq.) was subsequently added. The reaction mixture was stirred for 30 minutes. A solution consisting of (3aR,4R,5R,6aS)-4-((E)-3-(benzo[b]thiophen-2-yl)-3-oxoprop-1-enyl)-2-oxohexahydro-2H-cyclopenta[b]furan-5-yl biphenyl-4-carboxylate (intermediate 27, 2.73 g, 5.37 mmol, 1.0 molar equivalent) in THF (1.05 mL) was added to the reaction mixture over the course of 30 minutes as the temperature rose to −48° C. The reaction mixture temperature decreased to −60° C. and was further stirred for 18 hours as it warmed to 20° C. The reaction mixture was diluted with ethyl acetate (300 mL) and subsequently washed with 1:1 saturated ammonium chloride-water (3×50 mL), followed by brine (100 mL). The organic layer was separated, dried over sodium sulfate, filtered, and the filtrate was subsequently evaporated to give a foamy solid (3.55 g). The crude material was dissolved in DCM and then purified on a 120-g Analogix flash silica cartridge eluted with DCM (100%, 1 L) to DCM-methanol ((300:1), 1 L) to DCM-methanol ((200:1), 2 L) to afford product (1.43 g). A second flash silica column was performed using the same conditions to afford the title intermediate 28 (1.30 g, 47%); ¹H NMR (d₆-DMSO) δ 7.89-8.05 (m, 2H), 7.59-7.88 (m, 6H), 7.38-7.58 (m, 3H), 7.15-7.36 (m, 3H), 5.99-6.05 (m, 1H), 5.75-3.05 (m, 2H), 5.34-5.42 (m, 1H), 5.22 (pent, 1H), 5.04-5.14 (m, 1H), 2.79-3.02 (m, 3H), 2.38-2.68 (m, 2H), 1.98-2.11 (m, 1H); MS (+cESI) m/z 533 (m+Na⁺).

Procedure ii:

To a stirring solution consisting of 0.1 M (3aR,4R,5R,6aS)-4-((E)-3-(benzo[b]thiophen-2-yl)-3-oxoprop-1-enyl)-2-oxohexahydro-2H-cyclopenta[b]furan-5-yl biphenyl-4-carboxylate (27) in THF-methanol (2:1) cooled to −40° C. was added CeCl₃ heptahydrate. The reaction mixture was subsequently cooled to −78° C. and sodium borohydride (2 molar equivalents) was added. The reaction mixture was stirred for 1.5 hours and was subsequently quenched by the addition of acetone at −60° C. followed by the addition of a saturated aqueous ammonium chloride solution as the reaction mixture slowly warmed to room temperature. The reaction mixture was diluted with brine and acidified with a small amount of 5% KHSO₄. The product was extracted with ethyl acetate twice and the combined organic layers were dried over sodium sulfate, filtered and evaporated. The crude product was purified by flash chromatography on regular silica gel eluted with hexanes-ethyl acetate to afford the title intermediate 28.

Step C: Preparation of (3aR,4R,5R,6aS)-4-((R,E)-3-(benzo[b]thiophen-2-yl)-3-hydroxyprop-1-enyl)-5-hydroxyhexahydro-2H-cyclopenta[b]furan-2-one (29)

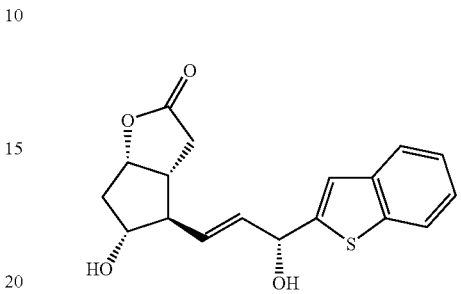

A mixture consisting of (3aR,4R,5R,6aS)-4-((R,E)-3-(benzo[b]thiophen-2-yl)-3-hydroxyprop-1-enyl)-2-oxohexahydro-2H-cyclopenta[b]furan-5-yl biphenyl-4-carboxylate (intermediate 28, 0.343 g, 0.672 mmol) and potassium carbonate (0.046 g, 0.336 mmol), and 1:1 methanol-THF (12 mL) was stirred at room temperature for 18 hours. The reaction mixture turned from colorless to red-orange. After complete consumption of starting material, as judged by TLC, the reaction mixture was diluted with ethyl acetate (300 mL), washed with 1:1 saturated ammonium chloride-water (2×50 mL) and brine (50 mL). The combined organic layers were dried over sodium sulfate, filtered and evaporated to give a yellow solid. The material was triturated in 10% ethyl acetate in hexanes (200 mL) for three days. The product was collected to give an off-white solid which was rinsed with hexanes and dried to afford the title intermediate 29 (189 mg, 85% triturated yield) as an off-white solid; MS (ESI⁺) m/z 313 (m+H—H₂O), (ESI⁻) m/z 389 (m+AcO⁻); ¹H NMR (d₆-DMSO) δ 7.83-7.93 (m, 1H), 7.72-7.83 (m, 1H), 7.24-7.38 (m, 2H), 7.19-7.24 (s, 1H), 5.94-6.01 (m, 1H), 5.65-5.82 (m, 2H), 5.31-5.38 (m, 1H), 4.94-5.01 (m, 1H), 4.84-4.93 (m, 1H), 3.80-3.91 (m, 1H), 2.74-2.88 (m, 1H), 2.56-2.69 (m, 1H), 2.22-2.37 (m, 3H), 1.64-1.80 (m, 1H).

Step D: Preparation of (3aR,4R,5R,6aS)-4-((3R,E)-3-(benzo[b]thiophen-2-yl)-3-(tetrahydro-2H-pyran-2-yloxy)prop-1-enyl)-5-(tetrahydro-2H-pyran-2-yloxy)hexahydro-2H-cyclopenta[b]furan-2-one (30)

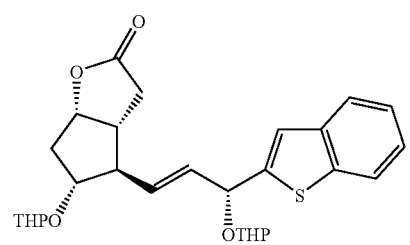

To a solution consisting of (3aR,4R,5R,6aS)-4-((R,E)-3-(benzo[b]thiophen-2-yl)-3-hydroxyprop-1-enyl)-5-hydroxyhexahydro-2H-cyclopenta[b]furan-2-one (intermediate 29, 300 mg, 0.908 mmol) in anhydrous DCM (12 mL) was added 3,4-dihydro-2H-pyran (0.33 mL, 0.31 g, 3.6 mmol, 4.0 molar equivalents), followed by a catalytic amount of pyridinium p-toluenesulfonate (23 mg, 0.09 mmol, 0.10 molar equivalent). The reaction mixture was stirred at room temperature for 18 hours. The reaction mixture was diluted with DCM (200 mL) and was subsequently washed with 50% brine in water (2×50 mL). The organic layer was separated, dried over sodium sulfate, filtered, and the filtrate was evaporated to give a crude product (626 mg) as a yellow oil. The crude product was purified on a 40-g Analogix flash silica cartridge. Elution with DCM-methanol ((200:1), 1 L) afforded the title intermediate 30 (394 mg, 87%); MS (+cAPCI) m/z 521 (m+Na$^+$); $^1$H NMR (d$_6$-DMSO) δ 7.89-7.97 (m, 1H), 7.76-7.85 (m, 1H), 7.26-7.41 (m, 2H), 5.65-5.91 (m, 2H), 4.81-4.98 (m, 2H), 4.61-4.70 (m, 2H), 3.64-4.09 (m, 2H), 3.29-3.56 (m, 2H), 2.16-2.94 (m, 5H), 1.17-1.91 (m, 14H).

Step E: Preparation of (3aR,4R,5R,6aS)-4-((3R,E)-3-(benzo[b]thiophen-2-yl)-3-(tetrahydro-2H-pyran-2-yloxy)prop-1-enyl)-5-(tetrahydro-2H-pyran-2-yloxy) hexahydro-2H-cyclopenta[b]furan-2-ol (31)

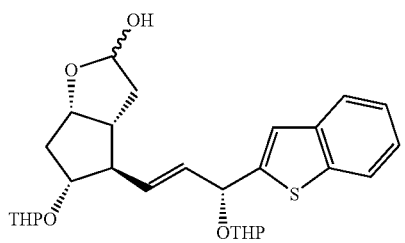

To a cold (−65 to −75° C.) solution consisting of (3aR,4R,5R,6aS)-4-((3R,E)-3-(benzo[b]thiophen-2-yl)-3-(tetrahydro-2H-pyran-2-yloxy)prop-1-enyl)-5-(tetrahydro-2H-pyran-2-yloxy)hexahydro-2H-cyclopenta[b]furan-2-one (intermediate 30, 0.369 mg, 0.740 mmol) in toluene (8 mL) was added a solution consisting of DIBAL-H in toluene (1 M, 1.11 mL) over the course of ten seconds. The reaction mixture was stirred for two hours and was complete as judged by TLC. The reaction mixture was warmed to 10° C. and was subsequently quenched with a 7:1 mixture of THF-water (8 mL). The reaction mixture was allowed to stir overnight (18 hours). After stirring overnight a white solid had formed. The reaction mixture was decanted away and the solid was washed with 50% brine in water (3×30 mL). The organic layer was separated, dried over sodium sulfate, filtered, and the filtrate was evaporated to afford the title intermediate 31 (413 mg, 112% crude) as a yellow-green oil; MS (+cAPCI) m/z 523 (m+Na$^+$); $^1$H NMR (CDCl$_3$), δ 7.70-8.00 (m, 2H), 7.20-7.40 (m, 3H), 5.40-5.50 (m, 3H), 4.55-4.95 (m, 5H), 1.20-2.60 (m, 20H).

Step F: Preparation of (Z)-7-((1R,2R,3R,5S)-2-((3R,E)-3-(benzo[b]thiophen-2-yl)-3-(tetrahydro-2H-pyran-2-yloxy)prop-1-enyl)-5-hydroxy-3-(tetrahydro-2H-pyran-2-yloxy)cyclopentyl)hept-5-enoic Acid (32)

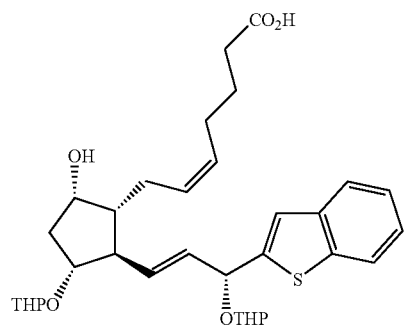

To a suspension consisting of 4-carboxybutyltriphenylphosphonium bromide (0.708 g, 1.60 mmol) in THF (5 mL) was added a mixture consisting of NaHMDS in THF (1 M, 4.30 mL). The reaction mixture was stirred at room temperature for 1.5 hours in which time a dark orange mixture had formed. The mixture was cooled to −10° C. (ice/NaCl bath) and a solution consisting of (3aR,4R,5R,6aS)-4-((3R,E)-3-(benzo[b]thiophen-2-yl)-3-(tetrahydro-2H-pyran-2-yloxy)prop-1-enyl)-5-(tetrahydro-2H-pyran-2-yloxy) hexahydro-2H-cyclopenta[b]furan-2-ol (intermediate 31, 0.400 g, 0.299 mmol) in THF (5 mL) was subsequently added to the orange colored suspension. The reaction mixture was stirred at −10° C. for 2 hours and the reaction mixture was then stirred in a refrigerator (+4° C.) for 3 days. The reaction mixture was stirred for 2 hours at room temperature and then quenched with 1:1 saturated ammonium chloride-water (15 mL). The reaction mixture was diluted with ethyl acetate (100 mL) and the layers were separated. The organic layer was washed with 1:1 saturated ammonium chloride-water (3×20 mL), dried over sodium sulfate, filtered, and evaporated. The crude material was dissolved in a minimal amount of DCM and purified on a 40-g Analogix flash silica cartridge. Elution with 150:1 DCM-methanol with 0.5% acetic acid (1 L) to 100:1 DCM-methanol with 0.5% acetic acid (600 mL) afforded the title intermediate 32 (201 mg, 46% over 2 steps) as a yellow oil; MS (cESI$^-$) m/z 589 (m−1); $^1$H NMR (CDCl$_3$), δ 7.75-8.00 (m, 2H), 7.10-7.40 (m, 3H), 5.30-5.90 (m, 4H), 4.95-5.05 (m, 1H), 4.55-4.70 (m, 2H), 3.35-4.20 (m, 5H), 1.40-2.65 (m, 26H).

Step G: Preparation of (Z)-7-((1R,2R,3R)-2-((3R,E)-3-(benzo[b]thiophen-2-yl)-3-(tetrahydro-2H-pyran-2-yloxy)prop-1-enyl)-5-oxo-3-(tetrahydro-2H-pyran-2-yloxy)cyclopentyl)hept-5-enoic Acid (33)

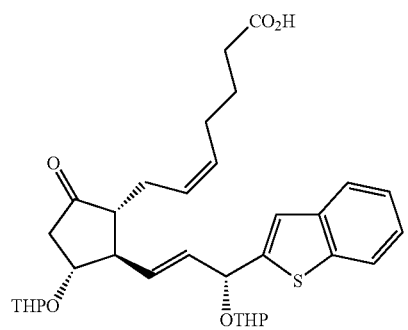

To a solution consisting of (Z)-7-((1R,2R,3R,5S)-2-((3R, E)-3-(benzo[b]thiophen-2-yl)-3-(tetrahydro-2H-pyran-2-yloxy)prop-1-enyl)-5-hydroxy-3-(tetrahydro-2H-pyran-2-yloxy)cyclopentyl)hept-5-enoic acid (intermediate 32, 0.191 g, 0.327 mmol) in anhydrous DCM (3 mL) was added Dess-Martin periodinane (0.153, 0.360 mmol). The reaction mixture was stirred at room temperature for 3 hours. The reaction mixture was concentrated under reduced pressure and purified on an 8-g Analogix flash silica cartridge. Elution with 200:1 DCM-methanol with 0.5% acetic acid (300 mL) afforded the title intermediate 33 (208 mg); MS (+cAPCI) m/z 605 (m+Na$^+$).

Step H: Preparation of (Z)-7-((1R,2R,3R)-2-((R,E)-3-(benzo[b]thiophen-2-yl)-3-hydroxyprop-1-enyl)-3-hydroxy-5-oxocyclopentyl)hept-5-enoic Acid (14a)

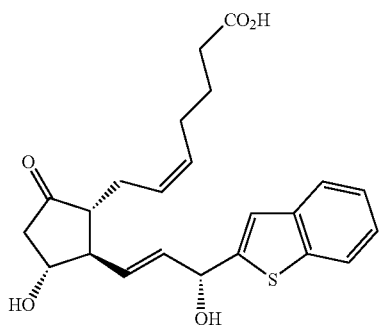

(Z)-7-((1R,2R,3R)-2-((3R,E)-3-(Benzo[b]thiophen-2-yl)-3-(tetrahydro-2H-pyran-2-yloxy)prop-1-enyl)-5-oxo-3-(tetrahydro-2H-pyran-2-yloxy)cyclopentyl)hept-5-enoic acid (33) was dissolved in a 4:2:1 solution of acetic acid-water-THF (0.5 M). The solution was stirred for several days at room temperature until the reaction was complete, as judged by TLC. The crude product was purified by flash chromatography on regular silica gel using ethyl acetate-hexane-0.5% acetic acid as eluent to afford the title compound 14a; TLC: R$_f$=0.20 (silica on 10 mm aluminum plates, eluent: 40:60:1 hexanes-ethyl acetate-acetic acid); MS (−cESI) m/z 413 (M−1); LC/MS: Sample prep-diluent, methanol. Sample prepared in 100 µL, unknown final concentration, analytical method: column: Phenomenex Synergi Hydro-RP 4p 250× 2.00 mm, flow rate 0.2 mL/min, detection UV (210 nm), column temperature 25° C., HPLC mobile phase: isocratic mobile phase consisting of 31.3% solvent A, 68.7% solvent B, Solvent A=10:90:0.1 methanol-water-acetic acid, Solvent B=90:10:0.1 methanol-water-acetic acid.

Example 8

Preparation of (Z)-7-((1R,2R,3R)-2-((R,E)-3-(benzo[d]thiazol-2-yl)-3-hydroxyprop-1-enyl)-3-hydroxy-5-oxocyclopentyl)hept-5-enoic Acid (14b)

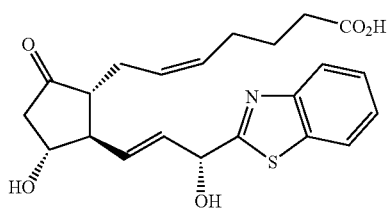

Steps A-H: Preparation of a mixture of (Z)-methyl-7-((1R,2R,5S)-2-((R,E)-3-(benzo[d]thiazol-2-yl)-3-(tert-butyldiphenylsilyloxy)prop-1-enyl)-5-hydroxy-3-oxocyclopentyl)hept-5-enoate (11b) and (Z)-methyl-7-((1R,2R,3R)-2-((R,E)-3-(benzo[d]thiazol-2-yl)-3-(tert-butyldiphenylsilyloxy)prop-1-enyl)-3-hydroxy-5-oxocyclopentyl)hept-5-enoate (12b)

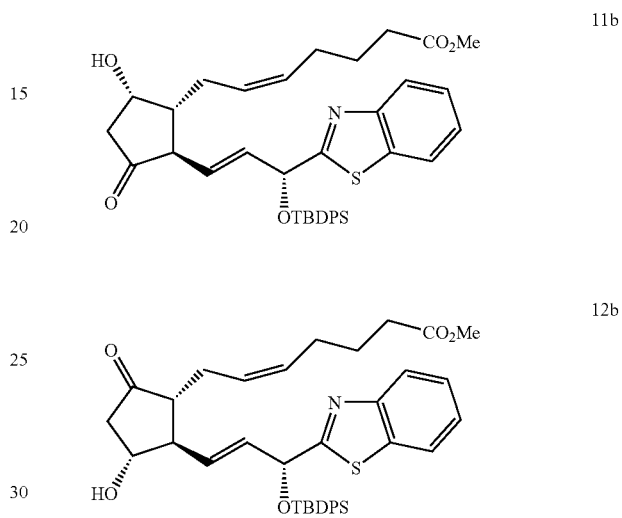

A mixture of the intermediates 11b and 12b are prepared from Corey lactone aldehyde benzoate, the mixture separated and each intermediate isolated using the series of procedures described for Example 2, Steps A-H, except that diethyl 2-(benzo[d]thiazol-2-yl)-2-oxoethylphosphonate (prepared from ethyl benzo[d]thiazole-2-carboxylate and diethyl methylphosphate according to a method described in the Journal of Organic Chemistry, 73(12), 2008, 4568-4574) is used instead of diethyl 2-(benzo[b]thiophen-2-yl)-2-oxoethylphosphonate in Step A.

Step I: Preparation of (Z)-7-((1R,2R,3R)-2-((R,E)-3-(benzo[d]thiazol-2-yl)-3-(tert-butyldiphenylsilyloxy)prop-1-enyl)-3-hydroxy-5-oxocyclopentyl)hept-5-enoic acid

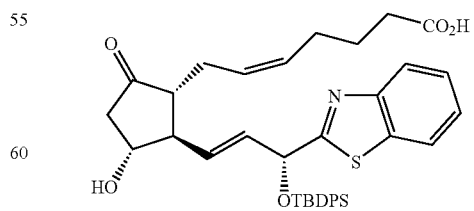

The title intermediate is prepared from intermediate 12b using a hydrolysis procedure described in Example 2, Step K.

Step J: Preparation of (Z)-7-((1R,2R,3R)-2-((R,E)-3-(benzo[d]thiazol-2-yl)-3-hydroxyprop-1-enyl)-3-hydroxy-5-oxocyclopentyl)hept-5-enoic Acid (14b)

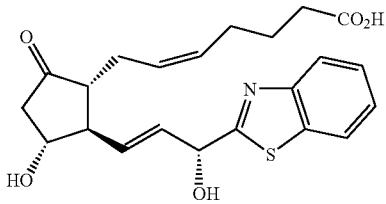

The title compound 14b is prepared from (Z)-7-((1R,2R,3R)-2-((R,E)-3-(benzo[d]thiazol-2-yl)-3-(tert-butyldiphenylsilyloxy)prop-1-enyl)-3-hydroxy-5-oxocyclopentyl)hept-5-enoic acid with a procedure similar to that which is described in Example 2, Step L.

Example 9

Preparation of (Z)-7-((1R,2R,5S)-2-((R,E)-3-(benzo[d]thiazol-2-yl)-3-hydroxyprop-1-enyl)-5-hydroxy-3-oxocyclopentyl)hept-5-enoic Acid (13b)

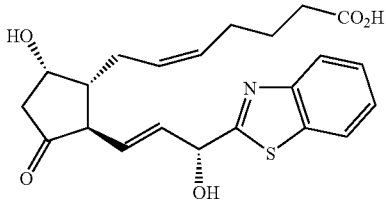

Step A: Preparation of (Z)-7-((1R,2R,5S)-2-((R,E)-3-(benzo[d]thiazol-2-yl)-3-(tert-butyldiphenylsilyloxy)prop-1-enyl)-5-hydroxy-3-oxocyclopentyl)hept-5-enoic Acid

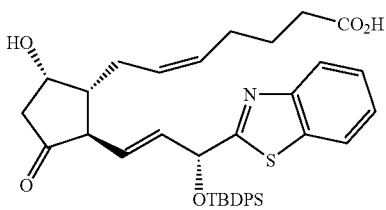

The title intermediate is prepared from intermediate 11b using a hydrolysis procedure described in Example 2, Step K).

Step B: Preparation of (Z)-7-((1R,2R,5S)-2-((R,E)-3-(benzo[d]thiazol-2-yl)-3-hydroxyprop-1-enyl)-5-hydroxy-3-oxocyclopentyl)hept-5-enoic Acid (13b)

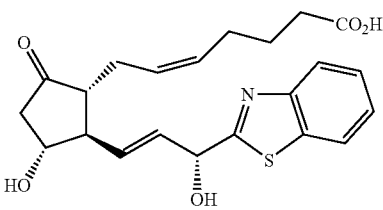

The title compound 13b is prepared from (Z)-7-((1R,2R,5S)-2-((R,E)-3-(benzo[d]thiazol-2-yl)-3-(tert-butyldiphenylsilyloxy)prop-1-enyl)-5-hydroxy-3-oxocyclopentyl)hept-5-enoic acid, prepared in Step A, with a procedure similar to that which is described in Example 2, Step L.

Examples 10-12

Reduced forms of compound 14a

Example 10

Preparation of 7-((1R,2R,3R)-2-((R,E)-3-(benzo[b]thiophen-2-yl)-3-hydroxyprop-1-enyl)-3-hydroxy-5-oxocyclopentyl)heptanoic Acid

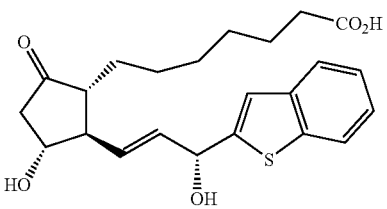

(Z)-7-((1R,2R,3R)-2-((R,E)-3-(Benzo[b]thiophen-2-yl)-3-hydroxyprop-1-enyl)-3-hydroxy-5-oxocyclopentyl)hept-5-enoic acid (Example 7, 1 molar equivalent) is dissolved in a 3:2 mixture of ethanol and benzene (0.01 M) under a nitrogen atmosphere. Wilkinson's catalyst (30% by weight relative to starting material) is added and hydrogen gas is introduced. The hydrogen uptake is monitored and upon theoretical consumption, the solvents are removed under reduced pressure and the residue is dissolved in a minimal amount of ethyl acetate containing 1% acetic acid. The crude product is purified using a filtration column on silica gel, eluted with 0.4% acetic acid in ethyl acetate. A second flash silica column eluted with an isopropanol-hexanes-acetic acid solvent system affords the title compound.

Example 11

Preparation of 7-((1R,2R,3R)-2-((R)-3-(benzo[b]thiophen-2-yl)-3-hydroxypropyl)-3-hydroxy-5-oxocyclopentyl)heptanoic acid

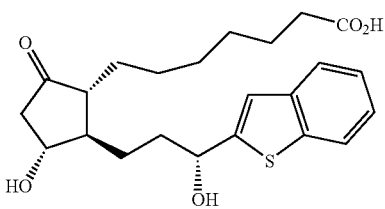

(Z)-7-((1R,2R,3R)-2-((R,E)-3-(Benzo[b]thiophen-2-yl)-3-hydroxyprop-1-enyl)-3-hydroxy-5-oxocyclopentyl)hept-5-enoic acid (Example 7, 1 molar equivalent) is dissolved in ethyl acetate (0.05 M) under a nitrogen atmosphere. 10% Pd/C (10 mol %) is added and hydrogen gas is introduced. After stirring for several hours at room temperature the reaction mixture is filtered over Celite. The crude product is purified by flash chromatography on regular silica gel eluted with ethyl acetate-hexanes (+0.4% acetic acid) to afford the title compound.

Example 12

Preparation of (Z)-7-((1R,2R,3R)-2-((R)-3-(benzo[b]thiophen-2-yl)-3-hydroxypropyl)-3-hydroxy-5-oxocyclopentyl)hept-5-enoic Acid

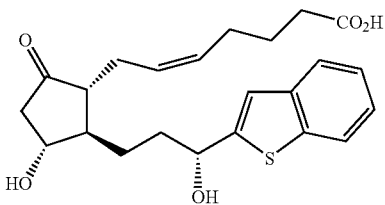

Step A: Preparation of (3aR,4R,5R,6aS)-4-((R)-3-(benzo[b]thiophen-2-yl)-3-(tert-butyldiphenylsilyloxy)propyl)hexahydro-2H-cyclopenta[b]furan-2,5-diol

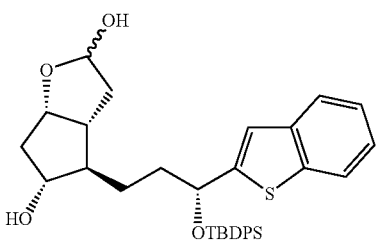

(3aR,4R,5R,6aS)-4-((R,E)-3-(Benzo[b]thiophen-2-yl)-3-(tert-butyldiphenylsilyloxy)prop-1-enyl)hexahydro-2H-cyclopenta[b]furan-2,5-diol (Example 2, Step E, 1 mol equivalent) is dissolved in ethyl acetate (0.05 M) under a nitrogen atmosphere. 10% Pd/C (10 mol %) is added and hydrogen gas is introduced. After stirring for several hours at room temperature the reaction mixture is filtered over Celite. The crude product is purified by flash chromatography on regular silica gel eluted with ethyl acetate-hexanes (+0.4% acetic acid) to afford the title intermediate.

Step B: Preparation of (Z)-7-((1R,2R,3R,5S)-2-((R)-3-(benzo[b]thiophen-2-yl)-3-(tert-butyldiphenylsilyloxy)propyl)-3,5-dihydroxycyclopentyl)hept-5-enoic Acid

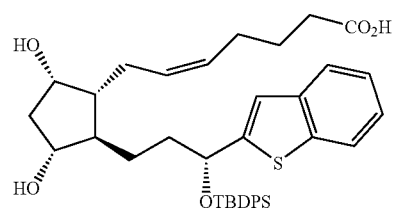

4-Carboxybutyltriphenylphosphonium bromide (3.5 molar equivalents) is suspended in anhydrous THF under a nitrogen atmosphere. Potassium tert-butoxide (1 M, 7 molar equivalents) in THF is added dropwise to the white suspension. The reaction mixture becomes bright red over the course of the addition and is subsequently stirred for 30 minutes at room temperature, then cooled to −15° C. in an ice/NaCl bath. The lactol (3aR,4R,5R,6aS)-4-((R)-3-(benzo[b]thiophen-2-yl)-3-(tert-butyldiphenylsilyloxy)propyl)hexahydro-2H-cyclopenta[b]furan-2,5-diol (1 molar equivalent) is dissolved in THF and added dropwise to the ylide. The reaction mixture becomes lighter orange in color and is further stirred for 2 hours at −15° C. and is then allowed to warm to room temperature and stir overnight. The reaction mixture becomes dark red. The reaction mixture is acidified with 5% aqueous KHSO$_4$, diluted with brine and extracted with ethyl acetate. The aqueous layer is extracted with another portion of ethyl acetate and the combined organic extracts are washed twice with brine, dried over sodium sulfate, and evaporated to yield crude product. The crude product is purified by flash chromatography on regular silica gel using ethyl acetate-hexane-acetic acid as eluent to afford the title intermediate.

Step C: Preparation, separation, and isolation of (Z)-7-((1R,2R,5S)-2-((R)-3-(benzo[b]thiophen-2-yl)-3-(tert-butyldiphenylsilyloxy)propyl)-5-hydroxy-3-oxocyclopentyl)hept-5-enoic acid and (Z)-7-((1R,2R,3R)-2-((R)-3-(benzo[b]thiophen-2-yl)-3-(tert-butyldiphenylsilyloxy)propyl)-3-hydroxy-5-oxocyclopentyl)hept-5-enoic acid

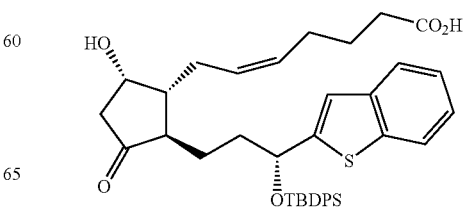

59

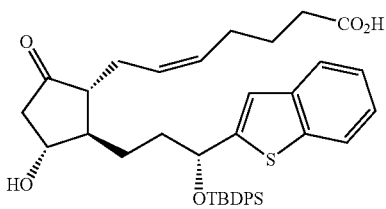

7-((1R,2R,3R,5S)-2-((R)-3-(Benzo[b]thiophen-2-yl)-3-(tert-butyldiphenylsilyloxy)propyl)-3,5-dihydroxycyclopentyl)heptanoic acid (1 molar equivalent) is dissolved in acetone (0.1 M) and cooled to −25° C. Jones reagent (1 molar equivalent) is added dropwise with stirring. Upon completion, as judged by TLC, the reaction is quenched with isopropyl alcohol and the crude reaction mixture is diluted with ethyl acetate, washed three times with brine, and dried over magnesium sulfate. After filtration and solvent evaporation, the product is purified by flash chromatography using ethyl acetate-hexane (with 0.4% acetic acid) as eluent to afford each of the title intermediates as separate products.

Step D: Preparation of (Z)-7-((1R,2R,3R)-2-((R)-3-(Benzo[b]thiophen-2-yl)-3-hydroxypropyl)-3-hydroxy-5-oxocyclopentyl)hept-5-enoic Acid

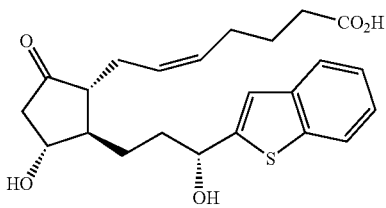

(Z)-7-((1R,2R,3R)-2-((R)-3-(Benzo[b]thiophen-2-yl)-3-(tert-butyldiphenylsilyloxy)propyl)-3-hydroxy-5-oxocyclopentyl)hept-5-enoic acid (1 molar equivalent) is dissolved in THF (0.3 M) under a nitrogen atmosphere. A solution consisting of TBAF in THF (1 M, 1.2 molar equivalents) is added and the reaction mixture is stirred at room temperature. Upon completion, as judged by TLC, water is added and most of the THF is removed under reduced pressure. The remaining aqueous solution is extracted with ethyl acetate and is washed with water and brine. The organic phase is dried over sodium sulfate, filtered, and the solvent is evaporated. The crude product is purified by flash chromatography on regular silica gel eluted with ethyl acetate-hexanes (+0.4% acetic acid) to afford the title compound.

60

Example 13

Preparation of (Z)-7-((1R,2R,3R)-2-((E)-3-(benzo[b]thiophen-2-yl)-3,3-difluoroprop-1-enyl)-3-hydroxy-5-oxocyclopentyl)hept-5-enoic Acid

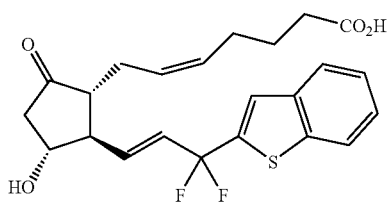

Step A: Preparation of (3aR,4R,5R,6aS)-4-((E)-3-(benzo[b]thiophen-2-yl)-3,3-difluoroprop-1-enyl)-2-oxohexahydro-2H-cyclopenta[b]furan-5-yl Benzoate

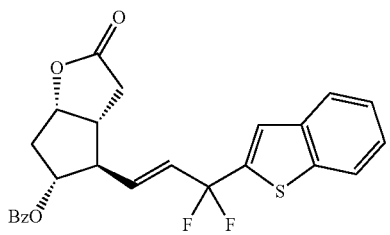

To a mixture consisting of (3aR,4R,5R,6aS)-4-((E)-3-(benzo[b]thiophen-2-yl)-3-oxoprop-1-enyl)-2-oxohexahydro-2H-cyclopenta[b]furan-5-yl benzoate (intermediate 4a prepared in Example 2, Step A) in anhydrous DCM (0.5 M) cooled to 0° C. under nitrogen atmosphere is added a catalytic amount of ethanol (25 mol %). To the stirring mixture is slowly added DAST (5 molar equivalents). The reaction mixture is allowed to slowly warm to room temperature overnight. Stirring is continued for several days until the reaction is complete as judged by TLC. Upon completion the reaction is cooled to 0° C. and quenched by the slow addition of a saturated aqueous solution of sodium bicarbonate. The layers are separated and the aqueous phase is extracted with ethyl acetate. The organic layers are combined and dried over magnesium sulfate. The solvents are evaporated and the crude material is purified on regular silica gel eluted with hexanes-ethyl acetate solvent system to afford the title intermediate.

Step B: Preparation of (3aR,4R,5R,6aS)-4-((E)-3-(benzo[b]thiophen-2-yl)-3,3-difluoroprop-1-enyl)-5-hydroxyhexahydro-2H-cyclopenta[b]furan-2-one

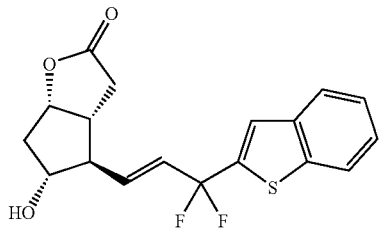

The title intermediate is prepared from (3aR,4R,5R,6aS)-4-((E)-3-(benzo[b]thiophen-2-yl)-3,3-difluoroprop-1-enyl)-2-oxohexahydro-2H-cyclopenta[b]furan-5-yl benzoate, prepared in Step A, with a procedure similar to that which is described in Example 1, Step D.

Step C: Preparation of (3aR,4R,5R,6aS)-4-((E)-3-(benzo[b]thiophen-2-yl)-3,3-difluoroprop-1-enyl)-5-(tetrahydro-2H-pyran-2-yloxy)hexahydro-2H-cyclopenta[b]furan-2-one

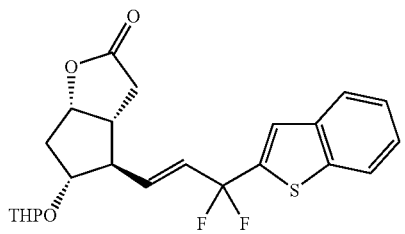

The title intermediate is prepared from (3aR,4R,5R,6aS)-4-((E)-3-(benzo[b]thiophen-2-yl)-3,3-difluoroprop-1-enyl)-5-hydroxyhexahydro-2H-cyclopenta[b]furan-2-one, prepared in Step B, with a procedure similar to that which is described in Example 1, Step E.

Step D: Preparation of (3aR,4R,5R,6aS)-4-((E)-3-(benzo[b]thiophen-2-yl)-3,3-difluoroprop-1-enyl)-5-(tetrahydro-2H-pyran-2-yloxy)hexahydro-2H-cyclopenta[b]furan-2-ol

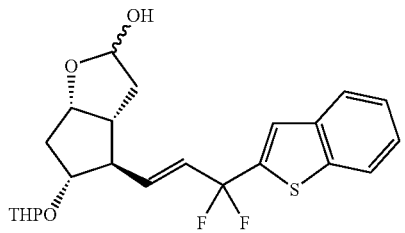

The title intermediate is prepared from (3aR,4R,5R,6aS)-4-((E)-3-(benzo[b]thiophen-2-yl)-3,3-difluoroprop-1-enyl)-5-(tetrahydro-2H-pyran-2-yloxy)hexahydro-2H-cyclopenta[b]furan-2-one, prepared in Step C, with a procedure similar to that which is described in Example 1, Step F.

Step E: Preparation of (Z)-7-((1R,2R,3R,5S)-2-((E)-3-(benzo[b]thiophen-2-yl)-3,3-difluoroprop-1-enyl)-5-hydroxy-3-(tetrahydro-2H-pyran-2-yloxy)cyclopentyl)hept-5-enoic acid

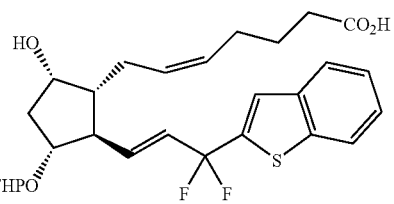

The title intermediate is prepared from (3aR,4R,5R,6aS)-4-((E)-3-(benzo[b]thiophen-2-yl)-3,3-difluoroprop-1-enyl)-5-(tetrahydro-2H-pyran-2-yloxy)hexahydro-2H-cyclopenta[b]furan-2-ol, prepared in Step D, with a procedure similar to that which is described in Example 1, Step G.

Step F: Preparation of (Z)-7-((1R,2R,3R)-2-((E)-3-(benzo[b]thiophen-2-yl)-3,3-difluoroprop-1-enyl)-5-oxo-3-(tetrahydro-2H-pyran-2-yloxy)cyclopentyl)hept-5-enoic acid

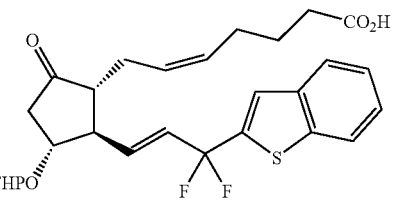

The title intermediate is prepared from (Z)-7-((1R,2R,3R,5S)-2-((E)-3-(benzo[b]thiophen-2-yl)-3,3-difluoroprop-1-enyl)-5-hydroxy-3-(tetrahydro-2H-pyran-2-yloxy)cyclopentyl)hept-5-enoic acid, prepared in Step E, with a procedure similar to that which is described in Example 1, Step H.

Step G: Preparation of (Z)-7-((1R,2R,3R)-2-((E)-3-(benzo[b]thiophen-2-yl)-3,3-difluoroprop-1-enyl)-3-hydroxy-5-oxocyclopentyl)hept-5-enoic Acid

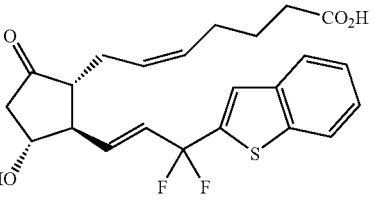

The title compound is prepared from (Z)-7-((1R,2R,3R)-2-((E)-3-(benzo[b]thiophen-2-yl)-3,3-difluoroprop-1-enyl)-5-oxo-3-(tetrahydro-2H-pyran-2-yloxy)cyclopentyl)hept-5-enoic acid, prepared in Step F, with a procedure similar to that which is described in Example 1, Step I.

Example 14

Preparation of (Z)-7-((1R,2R,3R)-2-((E)-3-(benzo[b]thiophen-2-yl)-3-hydroxybut-1-enyl)-3-hydroxy-5-oxocyclopentyl)hept-5-enoic Acid

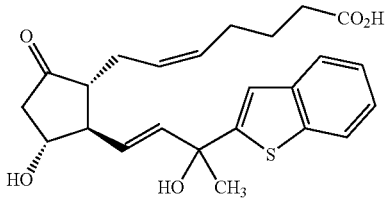

Step A: Preparation of (3aR,4R,5R,6aS)-4-((E)-3-(benzo[b]thiophen-2-yl)-3-hydroxybut-1-enyl)-2-oxohexahydro-2H-cyclopenta[b]furan-5-yl benzoate

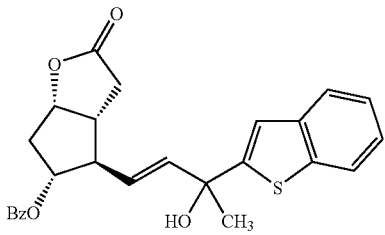

To a stirring solution consisting of (3aR,4R,5R,6aS)-4-((E)-3-(benzo[b]thiophen-2-yl)-3-oxoprop-1-enyl)-2-oxohexahydro-2H-cyclopenta[b]furan-5-yl benzoate (intermediate 4a prepared in Example 2, Step A) in THF (0.2 M) at −30° C. under a nitrogen atmosphere is slowly added a solution consisting of methylmagnesium bromide in diethyl ether (3 M, 1.5 molar equivalents). The reaction mixture is stirred at −30° C. until the reaction is complete as judged by TLC. Upon completion, the reaction mixture is warmed to 0° C. and is quenched with water and extracted into ethyl acetate. The layers are separated and the aqueous phase is extracted with a fresh portion of ethyl acetate. The organic layers are combined and dried over magnesium sulfate. The solvents are evaporated and the crude material is purified on regular silica gel eluted with an ethyl acetate-hexanes solvent system to afford the title intermediate.

Step B: Preparation of (3aR,4R,5R,6aS)-4-((E)-3-(benzo[b]thiophen-2-yl)-3-hydroxybut-1-enyl)-5-hydroxyhexahydro-2H-cyclopenta[b]furan-2-one

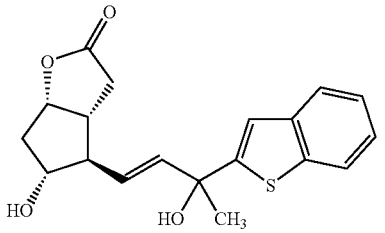

The title intermediate is prepared from (3aR,4R,5R,6aS)-4-((E)-3-(benzo[b]thiophen-2-yl)-3-hydroxybut-1-enyl)-2-oxohexahydro-2H-cyclopenta[b]furan-5-yl benzoate, prepared in Step A, with a procedure similar to that which is described in Example 1, Step D.

Step C: Preparation of (3aR,4R,5R,6aS)-4-((E)-3-(benzo[b]thiophen-2-yl)-3-(tetrahydro-2H-pyran-2-yloxy)but-1-enyl)-5-(tetrahydro-2H-pyran-2-yloxy)hexahydro-2H-cyclopenta[b]furan-2-one

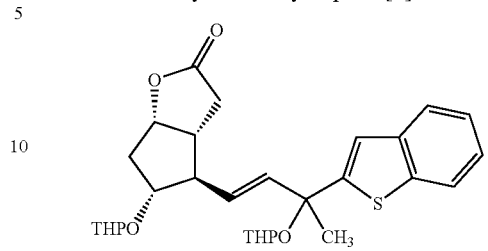

The title intermediate is prepared from (3aR,4R,5R,6aS)-4-((E)-3-(benzo[b]thiophen-2-yl)-3-hydroxybut-1-enyl)-5-hydroxyhexahydro-2H-cyclopenta[b]furan-2-one, prepared in Step B, with a procedure similar to that which is described in Example 13, Step D.

Step D: Preparation of (3aR,4R,5R,6aS)-4-((E)-3-(benzo[b]thiophen-2-yl)-3-(tetrahydro-2H-pyran-2-yloxy)but-1-enyl)-5-(tetrahydro-2H-pyran-2-yloxy)hexahydro-2H-cyclopenta[b]furan-2-ol

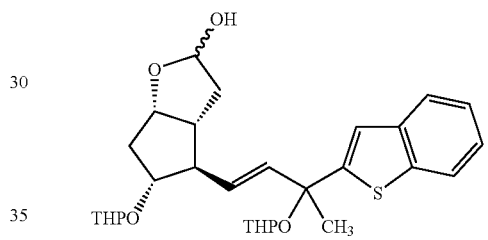

The title intermediate is prepared from (3aR,4R,5R,6aS)-4-((E)-3-(benzo[b]thiophen-2-yl)-3-(tetrahydro-2H-pyran-2-yloxy)but-1-enyl)-5-(tetrahydro-2H-pyran-2-yloxy)hexahydro-2H-cyclopenta[b]furan-2-one, prepared in Step C, with a procedure similar to that which is described in Example 1, Step F.

Step E: Preparation of (Z)-7-((1R,2R,3R,5S)-2-((E)-3-(benzo[b]thiophen-2-yl)-3-(tetrahydro-2H-pyran-2-yloxy)but-1-enyl)-5-hydroxy-3-(tetrahydro-2H-pyran-2-yloxy)cyclopentyl)hept-5-enoic acid

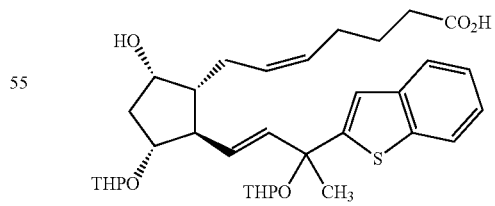

The title intermediate is prepared from (3aR,4R,5R,6aS)-4-((E)-3-(benzo[b]thiophen-2-yl)-3-(tetrahydro-2H-pyran-2-yloxy)but-1-enyl)-5-(tetrahydro-2H-pyran-2-yloxy)hexahydro-2H-cyclopenta[b]furan-2-ol, prepared in Step D, with a procedure similar to that which is described in Example 1, Step G.

Step F: Preparation of (Z)-7-((1R,2R,3R)-2-((E)-3-(benzo[b]thiophen-2-yl)-3-(tetrahydro-2H-pyran-2-yloxy)but-1-enyl)-5-oxo-3-(tetrahydro-2H-pyran-2-yloxy)cyclopentyl)hept-5-enoic acid

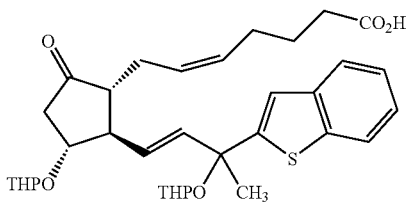

The title intermediate is prepared from (Z)-7-((1R,2R,3R,5S)-2-((E)-3-(benzo[b]thiophen-2-yl)-3-(tetrahydro-2H-pyran-2-yloxy)but-1-enyl)-5-hydroxy-3-(tetrahydro-2H-pyran-2-yloxy)cyclopentyl)hept-5-enoic acid, prepared in Step E, with a procedure similar to that which is described in Example 1, Step H.

Step G: Preparation of (Z)-7-((1R,2R,3R)-2-((E)-3-(benzo[b]thiophen-2-yl)-3-hydroxybut-1-enyl)-3-hydroxy-5-oxocyclopentyl)hept-5-enoic acid

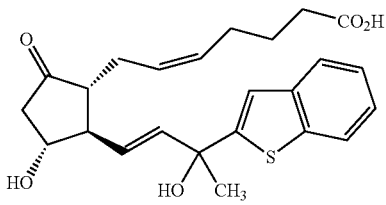

The title compound is prepared from (Z)-7-((1R,2R,3R)-2-((E)-3-(benzo[b]thiophen-2-yl)-3-(tetrahydro-2H-pyran-2-yloxy)but-1-enyl)-5-oxo-3-(tetrahydro-2H-pyran-2-yloxy)cyclopentyl)hept-5-enoic acid, prepared in Step F, in a manner similar to that as is described in Example 1, Step I.

Example 15

Preparation of (Z)-7-((1R,2R)-2-((R,E)-3-(benzo[b]thiophen-2-yl)-3-hydroxyprop-1-enyl)-3,3-difluoro-5-oxocyclopentyl)hept-5-enoic acid

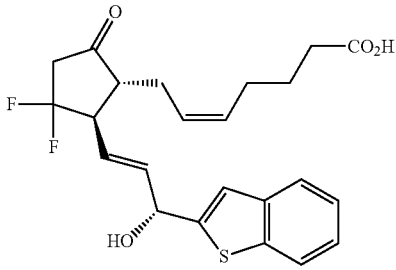

The title compound may be prepared from intermediate 15a with a series of five procedures comprising the following sequence: Example 2, Steps I, M, H, K, and L.

Example 16

Preparation of (Z)-7-((1R,5R)-5-((R,E)-3-(benzo[b]thiophen-2-yl)-3-hydroxyprop-1-enyl)-2,2-difluoro-4-oxocyclopentyl)hept-5-enoic acid

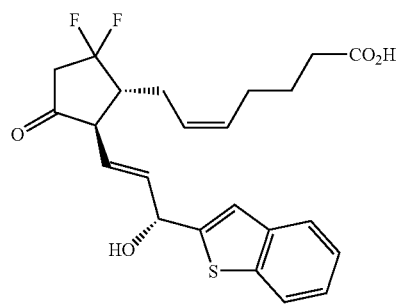

The title compound may be prepared from intermediate 16a with a series of five procedures comprising the following sequence: Example 2, Steps I, M, H, K, and L.

Example 17

Preparation of (Z)-7-((1R,2R,3S)-2-((S,E)-3-(2,3-dihydro-1H-inden-2-yl)-3-hydroxyprop-1-enyl)-3-fluoro-5-oxocyclopentyl)hept-5-enoic acid

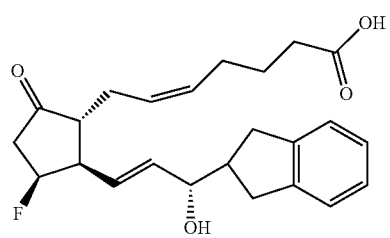

Step A: Preparation of (3aR,4S,5S,6aS)-4-((tert-butyldiphenylsilyloxy)methyl)-5-fluorohexahydro-2H-cyclopenta[b]furan-2-one

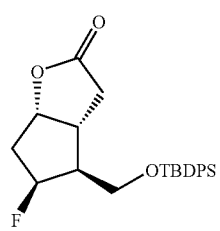

The DAST (1 molar equivalent) was placed in a 2-liter round bottom flask flushed with nitrogen and was dissolved in anhydrous $CH_2Cl_2$ (200 mL). This mixture was then cooled to −78° C. using an acetone/dry ice bath. After 20 minutes of cooling, a solution consisting of (3aR,4S,5R,6aS)-4-((tert-butyldiphenylsilyloxy)methyl)-5-hydroxyhexahydro-2H-cyclopenta[b]furan-2-one (prepared by appropriate silylation of the (−)-Corey lactone diol, 1 molar equivalent) in anhydrous $CH_2Cl_2$ (800 mL) was added slowly over a 30 minute period using an addition funnel. After the addition was complete, the −78° C. bath was removed and the reaction mixture was stirred overnight at room temperature. After this time the reaction mixture was brought to neutral pH with saturated $NaHCO_3$. The neutralized reaction mixture was transferred to a 6-liter separatory funnel, extracted with $CH_2Cl_2$ (2 L) and washed thrice with brine (3×2 L). The organic phase was dried over sodium sulfate and concentrated under reduced pressure. The crude product was purified on normal silica gel using 15% ethyl acetate in hexane as the eluent to afford the title intermediate (26.6 g, 48%).

Step B: Preparation of (3aR,4S,5S,6aS)-4-((tert-butyldiphenylsilyloxy)methyl)-5-fluorohexahydro-2H-cyclopenta[b]furan-2-ol

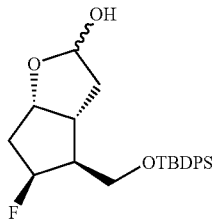

To a stirring solution consisting of (3aR,4S,5S,6aS)-4-((tert-butyldiphenylsilyloxy)methyl)-5-fluorohexahydro-2H-cyclopenta[b]furan-2-one (prepared in Step A, 26.6 g, 64.6 mmol) in anhydrous THF (1 L) cooled to −78° C. was added DIBAL-H (1 M solution in THF; 200 mL) dropwise. The reaction mixture was stirred at −78° C. and reaction progress was monitored by TLC. After 2 hours, the reaction mixture was quenched by the addition of 2:1 THF-water at −78° C. and the reaction mixture was allowed to warm to room temperature with stirring until precipitated aluminum salts settled out of solution. The aluminum salts were removed by filtration through a sintered glass fritted filter funnel and the filtrate was evaporated to dryness to afford the title intermediate (26 g) The crude intermediate was carried on with no further purification.

Step C: Preparation of (Z)-7-((1R,2S,3S,5S)-2-((tert-butyldiphenylsilyloxy)methyl)-3-fluoro-5-hydroxycyclopentyl)hept-5-enoic acid

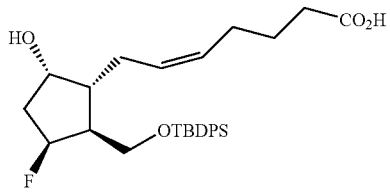

4-Carboxybutyltriphenylphosphonium bromide (55.81 g, 126.0 mmol) was suspended in anhydrous THF (1.5 L) and potassium t-butoxide (252 mL, 252 mmol) was added dropwise at room temperature. After the addition was complete, the orange ylide was cooled to 0° C. and (3aR,4S,5S,6aS)-4-((tert-butyldiphenylsilyloxy)methyl)-5-fluorohexahydro-2H-cyclopenta[b]furan-2-ol (prepared in Step B, 26 g, 63 mmol) as a solution in THF was added dropwise. The reaction mixture was allowed to slowly warm to room temperature overnight with stirring. The reaction was acidified with 5% $KHSO_4$, extracted with ethyl acetate, and washed twice with brine. The crude material was dried over sodium sulfate, filtered and evaporated to an oil. The crude product was purified on silica gel, eluted with hexanes-ethyl acetate (4:1 with 0.4% acetic acid) to afford the title intermediate (30.8 g, 97%).

Step D: Preparation of (Z)-isopropyl 7-((1R,2S,3S,5S)-2-((tert-butyldiphenylsilyloxy)methyl)-3-fluoro-5-hydroxycyclopentyl)hept-5-enoate

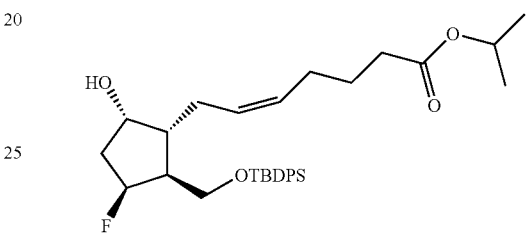

To a stirring solution consisting of (Z)-7-((1R,2S,3S,5S)-2-((tert-butyldiphenylsilyloxy)methyl)-3-fluoro-5-hydroxycyclopentyl)hept-5-enoic acid (prepared in Step C, 30.8 g, 61.6 mmol) in anhydrous DMF (1.2 L) was added cesium carbonate (30.0 g, 92.4 mmol) followed by iodopropane (22 g, 13 mL, 130 mmol). The reaction mixture was heated to 50° C. and stirred for 1.5 hours, monitoring by TLC. The reaction mixture was acidified with 5% $KHSO_4$, extracted with ethyl acetate, washed with brine, dried over sodium sulfate, filtered and evaporated. The crude product was purified on silica gel, eluted with hexanes-ethyl acetate (4:1) to afford the title intermediate (28.6 g, 86%).

Step E: Preparation of (Z)-isopropyl 7-((1R,2S,3S,5S)-2-((tert-butyldiphenylsilyloxy)methyl)-3-fluoro-5-(tetrahydro-2H-pyran-2-yloxy)cyclopentyl)hept-5-enoate

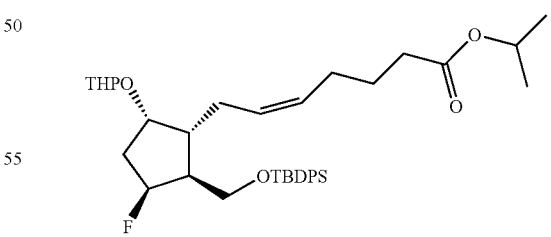

To a stirring solution consisting of (Z)-isopropyl 7-((1R,2S,3S,5S)-2-((tert-butyldiphenylsilyloxy)methyl)-3-fluoro-5-hydroxycyclopentyl)hept-5-enoate (prepared in Step D, 28.6 g, 52.8 mmol) in anhydrous DCM (500 mL) was added dihydropyran (6.69 g, 79.3 mmol). The reaction mixture was cooled to 0° C. and p-toluenesulfonic acid (25 mg) was subsequently added and the reaction was stirred for 2 hours at 0° C. The reaction mixture was then allowed to warm to room temperature and stirring was continued for another 2 hours. The crude reaction mixture was transferred to a separatory funnel, washed with saturated aqueous sodium bicarbonate solution and then with brine. The organic phase was dried over sodium sulfate, filtered, and the solvents were removed by evaporation to afford the crude title intermediate (32.7 g). The crude intermediate was carried on with no further purification.

Step F: Preparation of (Z)-isopropyl 7-((1R,2S,3S, 5S)-3-fluoro-2-(hydroxymethyl)-5-(tetrahydro-2H-pyran-2-yloxy)cyclopentyl)hept-5-enoate

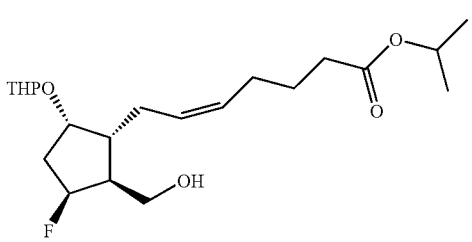

To a stirring solution consisting of (Z)-isopropyl 7-((1R, 2S,3S,5S)-2-((tert-butyldiphenylsilyloxy)methyl)-3-fluoro-5-(tetrahydro-2H-pyran-2-yloxy)cyclopentyl)hept-5-enoate (prepared in Step E, 2.7 g, 52 mmol) in anhydrous THF (500 mL) was slowly added a solution consisting of 1 M TBAF in THF (157 mL). The reaction mixture was stirred for 4 hours, monitoring by TLC. The reaction mixture was acidified with 5% KHSO$_4$, extracted into ethyl acetate, washed with brine, and dried over sodium sulfate, filtered, and concentrated under reduced pressure. The crude product was purified on silica gel, eluted with hexanes-ethyl acetate (3:1) to afford the title intermediate 12.94 g, 64%).

Step G: Preparation of (Z)-isopropyl 7-((1R,2S,3S, 5S)-3-fluoro-2-formyl-5-(tetrahydro-2H-pyran-2-yloxy)cyclopentyl)hept-5-enoate

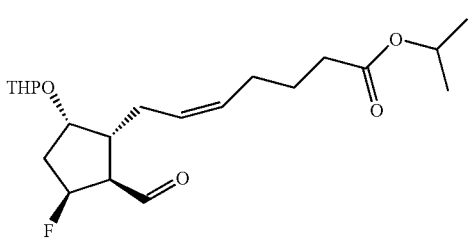

Oxalyl chloride (25 mL, 50 mmol) was dissolved in DCM (400 mL) and cooled to −78° C. under a nitrogen atmosphere, to which a solution consisting of DMSO (4.5 mL) in DCM (150 mL) was added. The reaction mixture was stirred for 15 minutes at −78° C. and a solution consisting of (Z)-isopropyl 7-((1R,2S,3S,5S)-3-fluoro-2-(hydroxymethyl)-5-(tetrahydro-2H-pyran-2-yloxy)cyclopentyl)hept-5-enoate (prepared in Step F, 12.94 g, 33.36 mmol) in DCM was subsequently added slowly. The reaction mixture was stirred for 40 minutes and triethylamine (28 mL) was subsequently added. Stirring was continued as the reaction mixture was allowed to warm to room temperature for 2 hours, monitoring by TLC. The reaction was acidified with 5% KHSO$_4$, extracted with DCM, and the organic layers were washed twice with brine. After drying over sodium sulfate, filtration, and solvent removal under reduced pressure, the crude product was purified on silica gel, eluted with hexanes-ethyl acetate (85:15) to afford the title intermediate (10.31 g, 80%).

Step H: Preparation of (Z)-isopropyl 7-((1R,2R,3S, 5S)-2-((E)-3-(2,3-dihydro-1H-inden-2-yl)-3-oxo-prop-1-enyl)-3-fluoro-5-(tetrahydro-2H-pyran-2-yloxy)cyclopentyl)hept-5-enoate

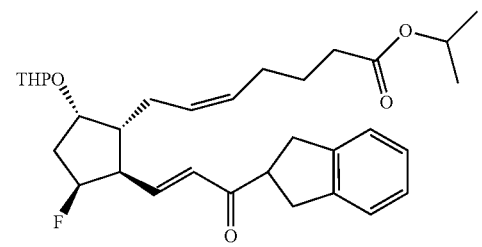

To a stirring mixture consisting of lithium chloride (3.75 g, 88.5 mmol) and triethylamine (4.86 mL) in THF (350 mL) cooled to 0° C. and stirred for 5 minutes at that temperature was added a solution consisting of dimethyl 2-(2,3-dihydro-1H-inden-2-yl)-2-oxoethylphosphonate (8.61 g) in THF (100 mL). The reaction mixture was stirred for 5 minutes and a solution consisting of (Z)-isopropyl 7-((1R,2S,3S,5S)-3-fluoro-2-formyl-5-(tetrahydro-2H-pyran-2-yloxy)cyclopentyl)hept-5-enoate (prepared in Step G, 10.31 g) in THF was added slowly. The reaction mixture was stirred as it was allowed to warm to room temperature overnight. The reaction mixture was subsequently acidified with 5% KHSO$_4$, extracted with DCM, and the organic layers were washed twice with brine. After drying over sodium sulfate, filtration, and solvent removal under reduced pressure, the crude product was purified on silica gel. Elution with hexanes-ethyl acetate (9:1) afforded the title intermediate (13.4 g, 94%).

Step I: Preparation of (Z)-isopropyl 7-((1R,2R,3S, 5S)-2-((S,E)-3-(2,3-dihydro-1H-inden-2-yl)-3-hydroxyprop-1-enyl)-3-fluoro-5-(tetrahydro-2H-pyran-2-yloxy)cyclopentyl)hept-5-enoate

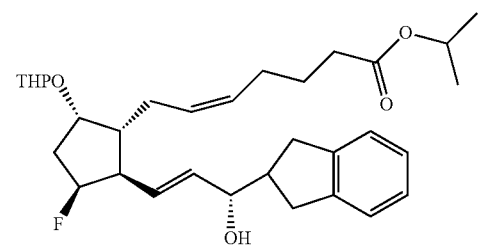

To a stirring mixture consisting of (Z)-isopropyl 7-((1R, 2R,3S,5S)-2-((E)-3-(benzo[b]thiophen-2-yl)-3-oxoprop-1-enyl)-3-fluoro-5-(tetrahydro-2H-pyran-2-yloxy)cyclopentyl)hept-5-enoate (prepared in Step H, 13.4 g) in methanol (325 mL) cooled to −40° C. was added CeCl$_3$ heptahydrate (9.46 g). The reaction mixture was further cooled to −78° C. and was stirred for an additional hour. Sodium borohydride (1.89 g) was added and the reaction mixture was stirred for one hour at −78° C. Upon completion (as visualized by TLC), the reaction was quenched by the addition of acetone and the mixture was warmed to room temperature. The mixture was subsequently acidified with 5% KHSO₄, extracted with DCM, and the organic layers were washed twice with brine. The organic phase was dried over sodium sulfate, filtered, and concentrated under reduced pressure to afford the crude title intermediate (15.2 g). The crude intermediate was carried on with no further purification.

Step J: Preparation of (Z)-isopropyl 7-((1R,2R,3S, 5S)-2-((S,E)-3-(2,3-dihydro-1H-inden-2-yl)-3-hydroxyprop-1-enyl)-3-fluoro-5-hydroxycyclopentyl) hept-5-enoate

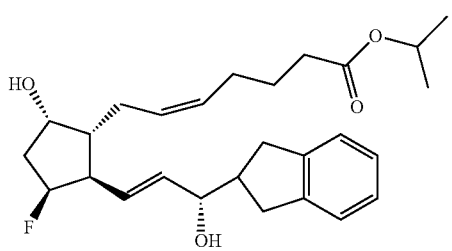

To a stirring mixture consisting of (Z)-isopropyl 7-((1R, 2R,3S,5S)-2-((S,E)-3-(2,3-dihydro-1H-inden-2-yl)-3-hydroxyprop-1-enyl)-3-fluoro-5-(tetrahydro-2H-pyran-2-yloxy)cyclopentyl)hept-5-enoate (prepared in Step I, 15.2 g) in a 10:1 isopropanol-water solution (300 mL) was added p-toluenesulfonic acid (1 g) and the reaction mixture was heated to 50° C. The reaction progress was monitored by TLC. Upon completion of reaction, the reaction mixture was evaporated to dryness and redissolved in ethyl acetate. The organic solution was washed twice with brine, dried over sodium sulfate, filtered, and concentrated under reduced pressure. The crude product was purified on silica gel. Elution with hexanes-ethyl acetate (9:1) afforded the title intermediate (2.2 g).

Step K: Preparation of (Z)-isopropyl 7-((1R,2R,3S, 5S)-2-((S,E)-3-(tert-butyldimethylsilyloxy)-3-(2,3-dihydro-1H-inden-2-yl)prop-1-enyl)-3-fluoro-5-hydroxycyclopentyl)hept-5-enoate

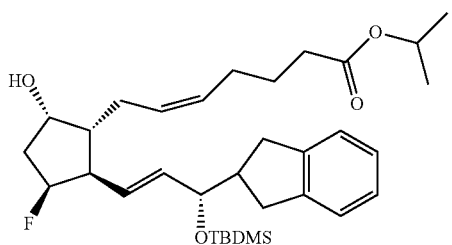

To a stirring mixture consisting of (Z)-isopropyl 7-((1R, 2R,3S,5S)-2-((S,E)-3-(2,3-dihydro-1H-inden-2-yl)-3-hydroxyprop-1-enyl)-3-fluoro-5-hydroxycyclopentyl)hept-5-enoate (prepared in Step J, 1.4 g) in DMF (30 mL) was added TBDMSCI (0.522 g) was added and the mixture was stirred at room temperature overnight. Upon completion, the mixture was diluted with ethyl acetate and washed two times with brine. After solvent removal, the crude product was purified on silica gel, eluted with hexanes-ethyl acetate (4:1) to afford the title intermediate (0.60 g, 8%).

Step L: Preparation of (Z)-isopropyl 7-((1R,2R,3S)-2-((S,E)-3-(tert-butyldimethylsilyloxy)-3-(2,3-dihydro-1H-inden-2-yl)prop-1-enyl)-3-fluoro-5-oxocyclopentyl)hept-5-enoate

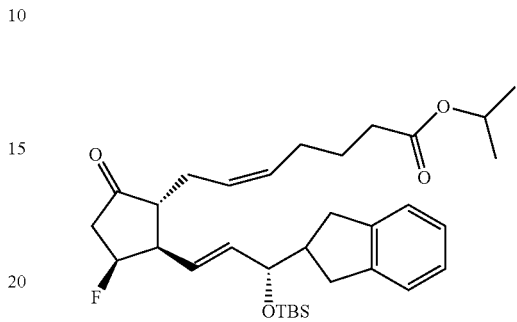

A mixture consisting of (Z)-isopropyl 7-((1R,2R,3S,5S)-2-((S,E)-3-(tert-butyldimethylsilyloxy)-3-(2,3-dihydro-1H-inden-2-yl)prop-1-enyl)-3-fluoro-5-hydroxycyclopentyl) hept-5-enoate (prepared in Step K, 0.600 g), methanol (5 mL), and 1 N sodium hydroxide (3 mL) was stirred overnight at 0° C. The reaction mixture was acidified with saturated ammonium chloride, extracted into ethyl acetate, washed with brine, and dried over sodium sulfate, filtered, and the solvents were evaporated under reduced pressure. The crude product was purified on silica gel. Elution with hexanes-ethyl acetate (4:1 with 0.4% acetic acid) afforded the title intermediate (0.58 g, 96%).

Step M: Preparation of (Z)-7-((1R,2R,3S)-2-((S,E)-3-(tert-butyldimethylsilyloxy)-3-(2,3-dihydro-1H-inden-2-yl)prop-1-enyl)-3-fluoro-5-oxocyclopentyl) hept-5-enoic acid

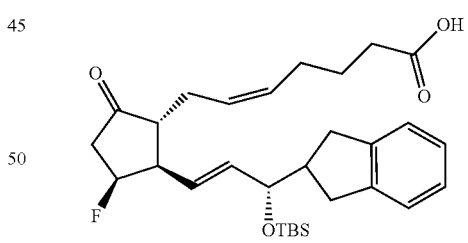

To a stirring mixture consisting of (Z)-isopropyl 7-((1R, 2R,3S)-2-((S,E)-3-(tert-butyldimethylsilyloxy)-3-(2,3-dihydro-1H-inden-2-yl)prop-1-enyl)-3-fluoro-5-oxocyclopentyl)hept-5-enoate (prepared in Step L, 580 mg) in DCM (30 mL) at room temperature was added Dess-Martin reagent (1.5 g) and the reaction mixture was stirred for 3 hours. The mixture was concentrated under reduced pressure and the residue was redissolved in diethyl ether. The insoluble materials were removed by filtration. The crude product in diethyl ether was applied to a silica gel column. Elution with hexanes-ethyl acetate (4:1 with 0.4% acetic acid) afforded the title intermediate (522 mg, 89%).

Step N: Preparation of (Z)-7-((1R,2R,3S)-2-((S,E)-3-(2,3-dihydro-1H-inden-2-yl)-3-hydroxyprop-1-enyl)-3-fluoro-5-oxocyclopentyl)hept-5-enoic acid

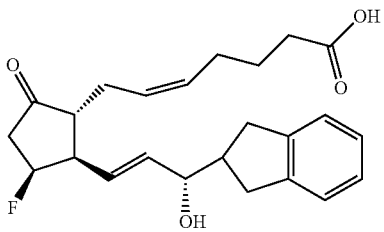

The title compound was prepared from (Z)-7-((1R,2R,3S)-2-((S,E)-3-(tert-butyldimethylsilyloxy)-3-(2,3-dihydro-1H-inden-2-yl)prop-1-enyl)-3-fluoro-5-oxocyclopentyl)hept-5-enoic acid (prepared in Step M) utilizing the conditions described in Example 2, Step L. The product was purified by semipreparative HPLC with conditions for purification as follows:

Purification

Column: 10 mm×250 mm, 4 μm, Synergi HydroRP C18

Mobile phase: 70:30:0.1 MeOH/H$_2$O/AcOH—premixed

Flow rate: 5 mL/min

UV monitored at 210 nm

Sample concentration: sample was dissolved at 100 mg/mL in 70:30 MeOH/H$_2$O Peaks were collected manually at 0° C. and purified batches were kept at −20° C. at the end of each day. Peak 2 (title compound, 14.6 minute retention time) degrades about 6% when left at 4° C. overnight in mobile phase and degrades minimally (<1%) when left at −20° C. overnight. Peak 1 (HF-eliminated by-product) possesses a retention time of 13 minutes. LCMS data of both products confirm masses consistent with the designations presented herein.

Purity of both peaks were >98% after purification and prior to concentration step.

Instrument used was a Gilson HPLC equipped with 321 binary pump, 215 liquid handler and 155 dual wavelength detector.

Example 18

Preparation of (Z)-7-((1R,2R)-2-((R,E)-3-(benzo[b]thiophen-2-yl)-3-hydroxyprop-1-enyl)-5-fluoro-3-oxocyclopentyl)hept-5-enoic acid

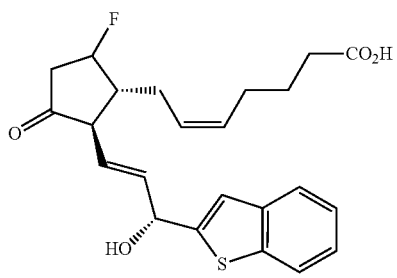

The title compound may be prepared from intermediate 11a (prepared in Example 2, Step H) by: (A) Protecting the keto group by preparing the intermediate (Z)-methyl 7-((6R,7R,8S)-6-((R,E)-3-(benzo[b]thiophen-2-yl)-3-(tert-butyldiphenylsilyloxy)prop-1-enyl)-8-hydroxy-1,4-dioxaspiro[4.4]nonan-7-yl)hept-5-enoate from 11a and ethane-1,2-diol using conditions known to those skilled in the art, (B) Treating the intermediate from (A) with DAST under conditions similar to those presented for Example 17, Step A, (C) Hydrolyzing the ester moiety of the intermediate prepared in Step (B) using conditions similar to those presented for Example 2, Step K, (D) Deprotecting the ketone on the intermediate prepared in Step (C) using methods known to those skilled in the art, and (E) Desilylation of the hydroxyl group on the intermediate prepared in Step (D) using conditions similar to those presented for Example 2, Step L.

Example 19 exemplifies a procedure that may generally be used to prepare compounds for which the terminal group of the α chain is the N-methanesulfonylamide functional group.

Example 19

Preparation of (Z)-7-((1R,2R,3R)-2-((R,E)-3-(benzo[b]thiophen-2-yl)-3-hydroxyprop-1-enyl)-3-hydroxy-5-oxocyclopentyl)-N-(methylsulfonyl)hept-5-enamide

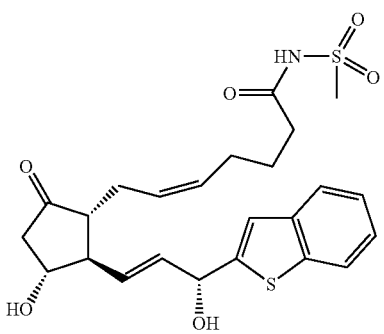

Step A: Preparation of 5-bromo-N-(methylsulfonyl)pentanamide

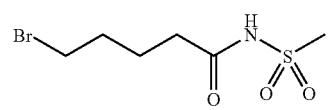

A mixture consisting of methanesulfonamide (4.76 g) and 5-bromovaleric acid chloride (10 g) was heated at 85-90° C. for one hour, was cooled to room temperature, and was diluted with ethyl acetate (75 mL). The solution was washed with water, brine, and dried over sodium sulfate. The solution was filtered and evaporated to 40 mL of solvent, then cooled to −15° C. A white precipitate formed, which was collected by filtration to afford the title intermediate (11.4 g, 88%) as a white solid; melting point 98-100° C.

Step B: Preparation of (5-(methylsulfonamido)-5-oxopentyl)triphenylphosphonium bromide

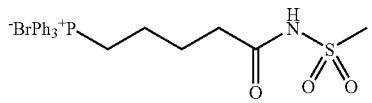

A stirring mixture consisting of triphenylphosphine (13.2 g, 24.4 mmol) and 5-bromo-N-(methylsulfonyl)pentanamide (prepared in Step A, 5.55 g, 21.5 mmol) in xylene (15 mL) was brought to reflux for 4 hours. Subsequently, ethyl acetate was added to the hot reaction mixture and stirring was continued for the next 15 minutes. The crude product was isolated from acetone-ethyl acetate to afford the title intermediate (8.68 g, 78%); melting point 189-190° C.

Step C: Preparation of (Z)-7-((1R,2R,3R,5S)-2-((3R,E)-3-(benzo[b]thiophen-2-yl)-3-(tetrahydro-2H-pyran-2-yloxy)prop-1-enyl)-5-hydroxy-3-(tetrahydro-2H-pyran-2-yloxy)cyclopentyl)-N-(methylsulfonyl)hept-5-enamide

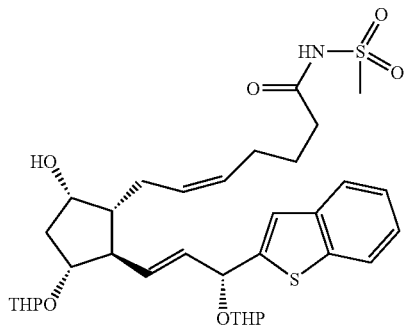

The title intermediate is prepared from (5-(methylsulfonamido)-5-oxopentyl)triphenylphosphonium bromide (prepared in Step B) and (3aR,4R,5R,6aS)-4-((3R,E)-3-(benzo[b]thiophen-2-yl)-3-(tetrahydro-2H-pyran-2-yloxy)prop-1-enyl)-5-(tetrahydro-2H-pyran-2-yloxy)hexahydro-2H-cyclopenta[b]furan-2-ol (intermediate 31 prepared in Example 13, Step E) in a manner similar to that as described in Example 1, Step G.

Step D: Preparation of (Z)-7-((1R,2R,3R)-2-((3R,E)-3-(benzo[b]thiophen-2-yl)-3-(tetrahydro-2H-pyran-2-yloxy)prop-1-enyl)-5-oxo-3-(tetrahydro-2H-pyran-2-yloxy)cyclopentyl)-N-(methylsulfonyl)hept-5-enamide

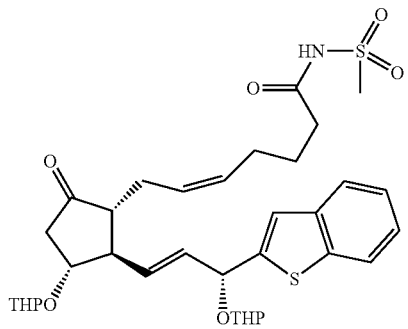

The title intermediate is prepared from (Z)-7-((1R,2R,3R,5S)-2-((3R,E)-3-(benzo[b]thiophen-2-yl)-3-(tetrahydro-2H-pyran-2-yloxy)prop-1-enyl)-5-hydroxy-3-(tetrahydro-2H-pyran-2-yloxy)cyclopentyl)-N-(methylsulfonyl)hept-5-enamide (prepared in Step C) in a manner similar to that described in Example 1, Step H.

Step E: Preparation of (Z)-7-((1R,2R,3R)-2-((R,E)-3-(benzo[b]thiophen-2-yl)-3-hydroxyprop-1-enyl)-3-hydroxy-5-oxocyclopentyl)-N-(methylsulfonyl)hept-5-enamide

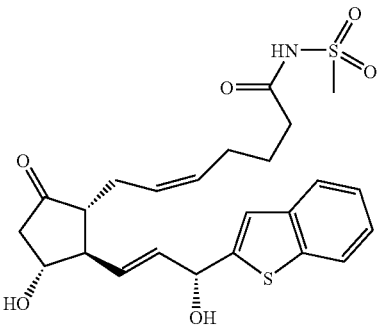

The title compound is prepared from (Z)-7-((1R,2R,3R)-2-((3R,E)-3-(benzo[b]thiophen-2-yl)-3-(tetrahydro-2H-pyran-2-yloxy)prop-1-enyl)-5-oxo-3-(tetrahydro-2H-pyran-2-yloxy)cyclopentyl)-N-(methylsulfonyl)hept-5-enamide (prepared in Step D) in a manner similar to that described in Example 1, Step I.

Example 20 exemplifies a procedure that may generally be used to convert carboxylic acid compounds to their respective carboxamides.

Example 20

Preparation of (Z)-7-((1R,2R,3R)-2-((R,E)-3-(benzo[b]thiophen-2-yl)-3-hydroxyprop-1-enyl)-3-hydroxy-5-oxocyclopentyl)-N-ethylhept-5-enamide

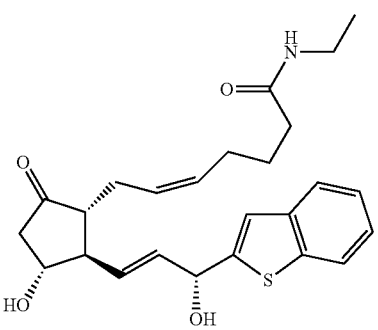

To a stirring mixture consisting of (Z)-7-((1R,2R,3R)-2-((R,E)-3-(benzo[b]thiophen-2-yl)-3-hydroxyprop-1-enyl)-3-hydroxy-5-oxocyclopentyl)hept-5-enoic acid (compound 14a, methods of preparation presented in Example 7, limiting reagent) in anhydrous DCM (0.1 M) under a nitrogen atmosphere is added N-hydroxysuccinimide (1.2 molar equivalents) and 1,3-dicyclohexylcarbodiimide (1.2 molar equivalents) and the reaction mixture is stirred overnight at room temperature. A white solid precipitates from the reaction mixture and is removed by filtration. The filtrate is evaporated to give the NHS-ester intermediate. The crude NHS-ester is dissolved in anhydrous DMF (0.2 M) under a nitrogen atmosphere. Ethylamine (1.5 molar equivalents) is added and the reaction mixture is stirred at room temperature overnight. The reaction mixture is diluted with brine and the product is extracted with ethyl acetate. The organic extracts are washed with brine, dried over sodium sulfate and evaporated. The product is purified by flash chromatography on regular silica gel. Elution with an ethyl acetate-hexanes solvent system affords the title compound.

EP Receptor Cloning and Expression

EP Receptor Cloning

Human prostaglandin $E_2$ receptor subtypes $EP_1$, $EP_2$, $EP_3$ and $EP_4$ are PCR amplified from commercially available full length human cDNAs (Open Biosystems, Origene). The MCS region of a mammalian expression vector pcDNA6/V5-HisA (Invitrogen) has been modified in-house to include a sequence cassette compatible with the USER Friendly PCR cloning system (New England Biolabs), and renamed pcDNA6/V5-HisA-USER. The PCR fragments of human $EP_1$, $EP_2$, $EP_3$ and $EP_4$ receptor subtypes with fragment ends compatible to the USER cassette are cloned into pcDNA6/V5-HisA-USER. All four EP receptor clones are sequence-confirmed prior to mammalian expression studies.

Mammalian Expression of Human EP Receptors

Mammalian expression is performed in HEK-293 cells using FuGENE® 6 Transfection Reagent (Roche) following the manufacturer's standard protocol. Cells expressing each of the EP receptor subtypes are selected using blasticidin. Foci of cells surviving blasticidin treatment are picked and expanded to allow the development of clonal EP-overexpressing stable cell lines. Highly expressing cell lines is identified by western blot analysis using antibodies selective for each of the four isotypes of the EP receptor (available in-house) and/or by assessing binding of $[^3H]$-$PGE_2$, as described below.

EP Receptor Binding and Agonism

The ability of compounds to bind the EP receptors and their selectivity for each receptor can be demonstrated in radioligand competition displacement binding experiments using the cell lines described above which stably overexpress the human EP receptors. The ability of compounds to activate the receptors can be demonstrated in second messenger functional assays, measuring changes in intracellular calcium for $EP_1$ and changes in cAMP formation for $EP_2$, $EP_3$ and $EP_4$.

Test Details

Binding Ability to Human EP Receptors

Membranes are prepared from cells stably transfected with human EP receptor DNA. In brief, cells are cultured to confluence, scraped from culture flasks and centrifuged to pellet (800×g, 5 minutes, 4° C.). Cells are washed twice with ice-cold homogenization buffer containing 10 mM Tris-HCl, 1 mM EDTA, 250 mM sucrose, 1 mM PMSF, 300 µM indomethacin, pH 7.4, homogenized by sonication and centrifuged as before. The supernatant is stored on ice; the pellets are rehomogenized and respun. Supernatants are pooled and centrifuged at 100,000×g for 10 minutes at 4° C. The resultant membrane pellet is stored at −80° C. until use.

For assays, membranes from cells expressing human $EP_1$, $EP_2$, $EP_3$ or $EP_4$ receptors are added to assay buffer (10 mM MES, pH 6.0, 10 mM $MgCl_2$, 1 mM EDTA, 3 µM indomethacin) containing 5 nM $[^3H]$-$PGE_2$ (GE Healthcare) and 0.1 to 10,000 nM concentrations of compounds to be tested. Incubations are performed at suitable temperatures and times to allow equilibration to be reached. Non-specific binding is determined in the presence of 10 µM $PGE_2$. Reactions are terminated by the addition of ice-cold buffer followed by rapid filtration through Whatman GF/B filters. The filters are dried after washing, and membrane-bound radioactivity is quantified by scintillation counting.

The affinity or $pK_i$ of each compound for each receptor is calculated from the concentration causing 50% radioligand displacement ($IC_{50}$) using the Cheng-Prosoff equation:

$$K_i = IC_{50}/[1+(\text{radioligand concentration/radioligand } K_d)]$$

Functional Assays Effect of Compounds on Second Messenger Generation

The following sections describe in vitro assays to determine the effect of compounds on calcium mobilization, and on the induction or inhibition of cAMP generation, that is, to determine the functional efficacy of compounds at the $EP_1$ (calcium mobilization), $EP_2$ (induction of cAMP), $EP_3$ (inhibition of forskolin-induced cAMP) or $EP_4$ (induction of cAMP) receptor.

$EP_1$ Receptor Agonism Assay (Intracellular Calcium Assay)

Functional Assay #1AGi

To test the ability of compounds to activate the $EP_1$ receptor, calcium mobilization experiments are performed. Cells expressing the $EP_1$ receptor are plated in clear-bottom black 96-well plates in normal growth medium and grown to confluence. When the cells have reached confluence, the culture medium is replaced with 50 µl of Fluo-4 NW dye mix (Invitrogen) that is dissolved in Hank's balanced salt solution containing 20 mM HEPES, pH 7.4 and 2.5 mM probenecid. Experiments are initiated by the addition of 50 µl/well of vehicle or compound to be tested diluted in this same buffer. Plates are incubated for 30 minutes at 37° C. and then at room temperature for an additional 30 minutes. Calcium fluorescence is measured using an Analyst AD (Molecular Devices) with an excitation wavelength of 485 nm, emission wavelength of 560 nm, and emission cutoff of 505 nm. Responses are quantified as peak fluorescence intensity minus basal fluorescence intensity.

Alternative $EP_1$ Receptor Agonism Assay

Functional Assay #1AGii (Cerep, Catalog reference 722-55a; UNGRIN, M. D., SINGH L. M. R., STOCCO, R., SAS, D. E. and ABRAMOVITZ, M. (1999), An automated aequorin luminescence-based functional calcium assay for G-Protein-Coupled Receptors. *Analytical Biochem.*, 272, 34.)

Evaluation of the agonist activity of compounds at the human $EP_1$ receptor in transfected HEK-293 cells, determined by measuring their effect on cytosolic $Ca^{2+}$ ion mobilization using a fluorimetric detection method.

The cells are suspended in DMEM buffer (Invitrogen), then distributed in microplates at a density of $3.10^4$ cells/well. The fluorescent probe (Fluo4 NR, Invitrogen) mixed with probenecid in HBSS buffer (Invitrogen) complemented with 20 mM Hepes (Invitrogen) (pH 7.4) is then added into each well and equilibrated with the cells for 30 minutes at 37° C. then 30 minutes at 22° C. Thereafter, the assay plates are positioned in a microplate reader (CellLux, PerkinElmer) which is used for the addition of the test compound, reference agonist or HBSS buffer (basal control), and the measurements of changes in fluorescence intensity which varies proportionally to the free cytosolic $Ca^{2+}$ ion concentration. For stimulated control measurements, $PGE_2$ at 100 nM is added in separate assay wells.

The results are expressed as a percent of the control response to 100 nM PGE2. The standard reference agonist is PGE2, which is tested in each experiment at several concentrations to generate a concentration-response curve from which its EC50 value is calculated.

EP$_1$ Receptor Antagonism Assay

Functional Assay #1ANT (Cerep, Catalog reference 722-55b; UNGRIN, M. D., et al., ibid.)

Evaluation of the antagonist activity of compounds at the human EP$_1$ receptor in transfected HEK-293 cells, determined by measuring their effect on agonist-induced cytosolic Ca$^{2+}$ ion mobilization using a fluorimetric detection method.

The cells are suspended in DMEM buffer (Invitrogen), then distributed in microplates at a density of $3.10^4$ cells/well. The fluorescent probe (Fluo4 NR, Invitrogen) mixed with probenicid in HBSS buffer (Invitrogen) complemented with 20 mM Hepes (Invitrogen) (pH 7.4) is then added into each well and equilibrated with the cells for 30 minutes at 37° C. then 30 minutes at 22° C. Thereafter, the assay plates are positioned in a microplate reader (CellLux, PerkinElmer) which is used for the addition of the test compound, reference antagonist or HBSS buffer (basal control), then 5 minutes later 3 nM PGE$_2$, and the measurements of changes in fluorescence intensity which varies proportionally to the free cytosolic Ca$^{2+}$ ion concentration. The results are expressed as a percent inhibition of the control response to 3 nM PGE$_2$. The standard reference antagonist is SC 51322, which is tested in each experiment at several concentrations to generate a concentration-response curve from which its IC$_{50}$ value is calculated.

EP$_2$ and EP$_4$ Receptor Agonism Assay (Cyclic AMP Induction Assay)

Functional Assay #2AGi and Functional Assay #4AGi, respectively

To test the ability of compounds to activate the EP$_2$ and EP$_4$ receptors, accumulation of cAMP following treatment with these compounds is measured. Cells expressing the EP$_2$ or EP$_4$ receptor are plated in 24-well plates in normal growth medium and grown to confluence. When the cells have reached confluence, the medium is replaced with 450 ml of serum-free medium containing 0.25 mM IBMX and 20 µM indomethacin. Cells are incubated in this medium for one hour. Fifty microliters of this same buffer containing various concentrations of PGE$_2$ or compounds to be tested is subsequently added to the cells and the cells are incubated for fifteen to thirty minutes to allow the accumulation of cAMP. Reactions are terminated by the addition of 500 µl of 10% TCA. cAMP measurements of the cell lysates are performed using Cayman Chemical's commercially available cAMP EIA Kit following the instructions provided in the kit booklet.

Alternative EP$_2$ Receptor Agonism Assay

Functional Assay #2AGii (Cerep, Catalog reference 758-54a; WILSON, R. J., RHODES, S. A., WOOD, R. L., SHIELD, V. J., NOEL, L. S., GRAY, D. W. and GILES H. (2004), Functional pharmacology of human prostanoid EP$_2$ and EP$_4$ receptors, *Eur. J. Pharmacol.*, 501, 49.)

Evaluation of the agonist activity of compounds at the human EP$_2$ receptor in transfected CHO cells, determined by measuring their effects on cAMP production using the HTRF detection method.

The cells are suspended in HBSS buffer (Invitrogen) complemented with HEPES 20 mM (pH 7.4) and 500 µM IBMX, then distributed in microplates at a density of $10^4$ cells/well and incubated for 30 minutes at 37° C. in the absence (control) or presence of the test compound or the reference agonist. For stimulated control measurements, separate assay wells contain 10 µM PGE$_2$. Following incubation, the cells are lysed and the fluorescence acceptor (D2-labeled cAMP) and fluorescence donor (anti-cAMP antibody labeled with europium cryptate) are added. After 60 minutes at room temperature, the fluorescence transfer is measured at $\lambda$ex=337 nm and $\lambda$em=620 and 665 nm using a microplate reader (Rubystar, BMG). The cAMP concentration is determined by dividing the signal measured at 665 nm by that measured at 620 nm (ratio). The results are expressed as a percent of the control response to 10 µM PGE$_2$. The standard reference agonist is PGE$_2$, which is tested in each experiment at several concentrations to generate a concentration-response curve from which its EC$_{50}$ value is calculated.

EP$_2$ Receptor Antagonism Assay

Functional Assay #2ANT (Cerep, Catalog reference 758-54b; WILSON, R. J., et al., ibid.)

Evaluation of the antagonist activity of compounds at the human EP$_2$ receptor in transfected CHO cells, determined by measuring their effects on agonist-induced cAMP production using the HTRF detection method.

The cells are suspended in HBSS buffer (Invitrogen) complemented with HEPES 20 mM (pH 7.4) and 500 µM IBMX, then distributed in microplates at a density of $10^4$ cells/well and preincubated for 5 minutes at room temperature in the absence (control) or presence of the test compound or the reference antagonist. Thereafter, the reference agonist PGE$_2$ is added at a final concentration of 300 nM. For basal control measurements, separate assay wells do not contain PGE$_2$. Following 30 minutes incubation at 37° C., the cells are lysed and the fluorescence acceptor (D2-labeled cAMP) and fluorescence donor (anti-cAMP antibody labeled with europium cryptate) are added. After 60 minutes at room temperature, the fluorescence transfer is measured at $\lambda$ex=337 nm and $\lambda$em=620 and 665 nm using a microplate reader (Rubystar, BMG). The cAMP concentration is determined by dividing the signal measured at 665 nm by that measured at 620 nm (ratio). The results are expressed as a percent inhibition of the control response to 300 nM PGE$_2$. The standard reference antagonist is AH 6809, which is tested in each experiment at several concentrations to generate a concentration-response curve from which its IC$_{50}$ value is calculated.

EP$_3$ Receptor Agonism Assay (Inhibition of Forskolin-Induced cAMP Generation Assay)

Functional Assay #3AG

To test the ability of compounds to activate the EP$_3$ receptor, the decrease in cAMP accumulation induced by forskolin following treatment with compounds is measured. Cells expressing the EP$_3$ receptor are plated in 24-well plates in normal growth medium and allowed to come to confluence. When the cells have come to confluence, the medium is replaced with 450 µl of serum-free medium containing 0.25 mM IBMX and 20 µM indomethacin. Cells are incubated in this medium for one hour. Fifty microliters of this same buffer containing 3 µM forskolin and various concentrations of PGE$_2$ or compounds to be tested are subsequently added to the cells. After incubation at 37° C. for 10 minutes, reactions are terminated by the addition of 500 µl of 10% TCA. cAMP measurements of the cell lysates are performed using Cayman Chemical's cAMP EIA Kit following the instructions provided in the kit booklet.

Alternative EP$_4$ Receptor Agonism Assay

Functional Assay #4AGii (Cerep, Catalog Reference 758-49a; Wilson, R. J., et al., Ibid.)

Evaluation of the agonist activity of compounds at the human EP$_4$ receptor in transfected CHO cells, determined by measuring their effects on cAMP production using the HTRF detection method.

The cells are suspended in HBSS buffer (Invitrogen) complemented with HEPES 20 mM (pH 7.4) and 500 µM IBMX, then distributed in microplates at a density of 2.10⁴ cells/well and incubated for 10 minutes at room temperature in the absence (control) or presence of the test compound or the reference agonist. For stimulated control measurements, separate assay wells contain 1 μM $PGE_2$. Following incubation, the cells are lysed and the fluorescence acceptor (D2-labeled cAMP) and fluorescence donor (anti-cAMP antibody labeled with europium cryptate) are added. After 60 minutes at room temperature, the fluorescence transfer is measured at λex=337 nm and λem=620 and 665 nm using a microplate reader (Rubystar, BMG). The cAMP concentration is determined by dividing the signal measured at 665 nm by that measured at 620 nm (ratio). The results are expressed as a percent of the control response to 1 μM $PGE_2$. The standard reference agonist is $PGE_2$, which is tested in each experiment at several concentrations to generate a concentration-response curve from which its $EC_{50}$ value is calculated.

$EP_4$ Receptor Antagonism Assay

Functional Assay #4ANT (Cerep, Catalog reference 758-49b; WILSON, R. J., et al., ibid.)

Evaluation of the antagonist activity of compounds at the human $EP_4$ receptor in transfected CHO cells, determined by measuring their effects on agonist-induced cAMP production using the HTRF detection method.

The cells are suspended in HBSS buffer (Invitrogen) complemented with HEPES 20 mM (pH 7.4) and 500 μM IBMX, then distributed in microplates at a density of 2.10⁴ cells/well and preincubated for 5 minutes at room temperature in the absence (control) or presence of the test compound or the reference antagonist. Thereafter, the reference agonist $PGE_2$ is added at a final concentration of 10 nM. For basal control measurements, separate assay wells do not contain $PGE_2$. Following 10 minutes incubation at room temperature, the cells are lysed and the fluorescence acceptor (D2-labeled cAMP) and fluorescence donor (anti-cAMP antibody labeled with europium cryptate) are added. After 60 minutes at room temperature, the fluorescence transfer is measured at λex=337 nm and λem=620 and 665 nm using a microplate reader (Rubystar, BMG). The cAMP concentration is determined by dividing the signal measured at 665 nm by that measured at 620 nm (ratio). The results are expressed as a percent inhibition of the control response to 10 nM $PGE_2$. There is no standard reference antagonist for this assay.

The above description of embodiments of the invention is merely exemplary in nature and, thus, variations thereof are not to be regarded as a departure from the spirit and scope of the invention.

What is claimed is:

1. A compound of the general formula (I):

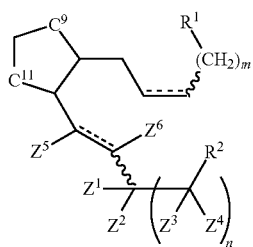

I wherein dashed bonds may each independently represent a second carbon-carbon bond in order to give a carbon-carbon double bond with either (E) or (Z) geometry or may be ignored in order to give a carbon-carbon single bond;

wherein $C^9$ and $C^{11}$ each is independently C=$CH_2$, C=O, $CF_2$, CHF (any stereoisomer), or C(H)OH (any stereoisomer) with the proviso that $C^9$ does not equal $C^{11}$ and also with the proviso that when one of either $C^9$ or $C^{11}$ is CHF, the other is not C(H)OH;

wherein $R^1$ is $CO_2R^3$, $CH_2OR^3$, $CONR^4R^5$, $COCH_2OH$, $CONR^4SO_2R^5$, $P(O)(OR^4)_2$, or

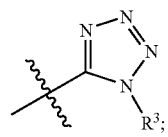

wherein $R^3$ is hydrogen or $(C_1-C_6)$-alkyl;

wherein $R^4$ and $R^5$ each is independently hydrogen or $(C_i-C_o)$-alkyl;

wherein m is 0, 1, 2, or 3;

wherein $Z^1$ and $Z^2$ each is independently hydrogen, fluorine, hydroxy, or methyl, or together are an oxygen atom that form a carbonyl group with the adjoining carbon atom of the ω chain;

wherein $Z^3$ and $Z^4$ each is independently hydrogen, fluorine, hydroxy, or methyl;

wherein n is 0 or 1, with the further proviso that when n is 1 and $Z^3$ is hydrogen, then $Z^4$ is not hydrogen; and with the further proviso that when n is 1 and $Z^4$ is hydrogen, then $Z^3$ is not hydrogen;

wherein $Z^5$ and $Z^6$ each is independently hydrogen, fluorine, hydroxy, or methyl;

wherein $R^2$ is

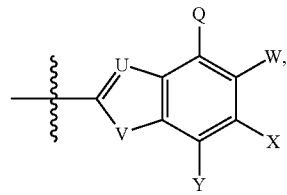

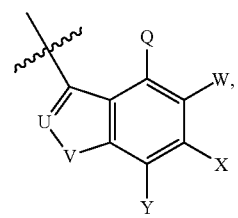

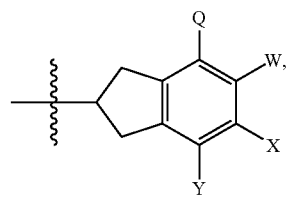

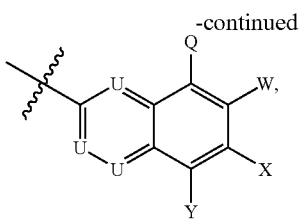

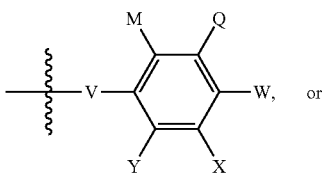

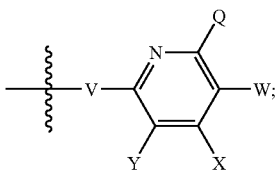

wherein V, if present, is O, S, or NR$^6$;

wherein any U is CH or N;

wherein M, Q, W, X, and Y are independently hydrogen, fluorine, chlorine, bromine, iodine, hydroxy, methoxy, trifluoromethoxy, cyano, trifluoromethyl, $(C_3-C_6)$-cycloalkyl, $(C_2-C_6)$-alkenyl, or $(C_2-C_6)$-alkynyl, wherein any alkyl, cycloalkyl, alkenyl, or alkynyl is optionally substituted with one or more fluorine atoms; and wherein R$^6$ is hydrogen, $(C_1-C_6)$-alkyl, $(C_3-C_6)$-cycloalkyl, $(C_2-C_6)$-alkenyl, $(C_2-C_6)$-alkynyl, phenyl, benzyl, three- to six-membered heterocycle, or five- to six-membered heteroaryl;

or any stereoisomer of the compound of the general formula (I), or any geometric isomer of the compound of the general formula (I), or an equivalent of the compound of the general formula (I), or a pharmaceutically acceptable salt of the compound of the general formula (I).

2. The compound of claim 1, wherein C$^9$ and C$^{11}$ each is independently C=O or C(H)OH (any stereoisomer) or C=CH$_2$ with the proviso that C$^9$ does not equal C$^{11}$.

3. The compound of claim 1, wherein C$^9$ and C$^{11}$ each is independently C=O or C(H)OH (any stereoisomer) with the proviso that C$^9$ does not equal C$^{11}$.

4. The compound of claim 1, wherein C$^9$ and C$^{11}$ each is independently C=O or C(H)OH (any stereoisomer) or CF$_2$ with the proviso that C$^9$ does not equal C$^{11}$.

5. The compound of claim 1, wherein C$^9$ and C$^{11}$ each is independently C=O or CHF (any stereoisomer) with the proviso that C$^9$ does not equal C$^{11}$.

6. The compound of claim 1, wherein the compound of the general formula (I) comprises the compound of general formula (II):

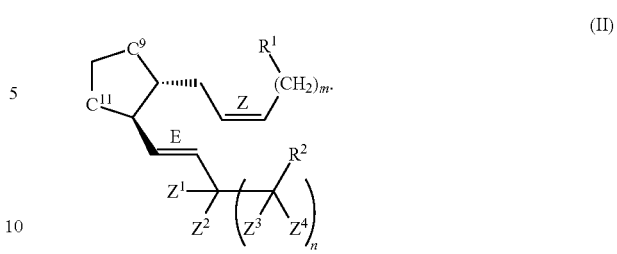

7. The compound of claim 1, wherein the compound of the general formula (I) comprises the compound of general formula (III):

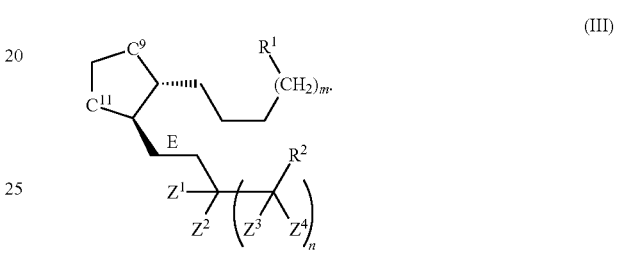

8. The compound of claim 1, wherein the compound of the general formula (I) comprises the compound of general formula (IV):

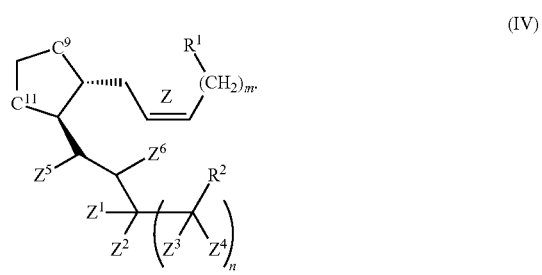

9. The compound of claim 1, wherein the compound of the general formula (I) comprises the compound of general formula (V):

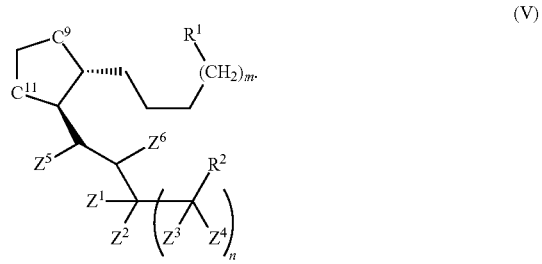

10. The compound of claim 1, wherein the compound of the general formula (I) comprises (Z)-7-((1R,2R,3R)-2-((R,E)-3-(benzo[b]thiophen-2-yl)-3-hydroxyprop-1-enyl)-3-hydroxy-5-oxocyclopentyl)hept-5-enoic acid.

11. A pharmaceutical composition comprising a pharmaceutically effective amount of a compound of claim 1 in admixture with a pharmaceutically acceptable carrier.

12. A method of expanding hematopoietic stem cell populations in a culture or patient in need thereof comprising administering to the culture or the patient a compound according to claim 1.

13. A method for treating EP receptor-mediated conditions in a subject, comprising the step of administering to the subject a compound according to claim 1.

14. The method of claim 13, wherein said compound further comprises a pharmaceutically acceptable carrier.

* * * * *

UNITED STATES PATENT AND TRADEMARK OFFICE
CERTIFICATE OF CORRECTION

PATENT NO.      : 8,063,240 B2
APPLICATION NO. : 12/271764
DATED           : November 22, 2011
INVENTOR(S)     : Nancy S. Barta et al.

It is certified that error appears in the above-identified patent and that said Letters Patent is hereby corrected as shown below:

On the Title Page, in Item (75) Inventors; delete "Andriy" and insert --Andrei--.

In the Claims

Column 83, line 30, after "present, is" delete "0," and insert --O,--.

Column 83, line 36, after "trifluoromethyl," insert --($C_1$-$C_6$)-alkyl--.

Column 84, line 20, formula (III), add double bond directly under "E" in claim 7.

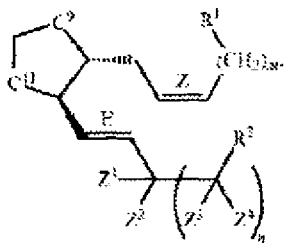

Column 84, line 66, after "3-(benzo" delete "[b]" and insert --[*b*]--.

Signed and Sealed this
Twenty-fourth Day of September, 2013

Teresa Stanek Rea
*Deputy Director of the United States Patent and Trademark Office*